United States Patent
Alig et al.

(10) Patent No.: US 9,512,128 B2
(45) Date of Patent: Dec. 6, 2016

(54) ARYL SULFIDE DERIVATIVES AND ARYL SULFOXIDE DERIVATIVES AS ACARICIDES AND INSECTICIDES

(71) Applicant: BAYER CROPSCIENCE AG, Monheim (DE)

(72) Inventors: Bernd Alig, Koenigswinter (DE); Silvia Cerezo-Galvez, Langenfeld (DE); Reiner Fischer, Monheim (DE); Adeline Koehler, Langenfeld (DE); Julia Johanna Hahn, Duesseldorf (DE); Angela Becker, Duesseldorf (DE); Kerstin Ilg, Cologne (DE); Arnd Voerste, Cologne (DE); Ulrich Goergens, Ratingen (DE); Daniela Portz, Vettweiss (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/653,515

(22) PCT Filed: Dec. 18, 2013

(86) PCT No.: PCT/EP2013/077061
§ 371 (c)(1),
(2) Date: Jun. 18, 2015

(87) PCT Pub. No.: WO2014/095979
PCT Pub. Date: Jun. 26, 2014

(65) Prior Publication Data
US 2015/0344499 A1    Dec. 3, 2015

(30) Foreign Application Priority Data

Dec. 20, 2012  (EP) .................... 12198486

(51) Int. Cl.
| | |
|---|---|
| *C07D 487/04* | (2006.01) |
| *C07D 495/04* | (2006.01) |
| *C07D 513/04* | (2006.01) |
| *A01N 43/80* | (2006.01) |
| *A01N 43/58* | (2006.01) |
| *A01N 43/90* | (2006.01) |
| *A01N 25/00* | (2006.01) |

(52) U.S. Cl.
CPC ............. *C07D 487/04* (2013.01); *A01N 25/00* (2013.01); *A01N 43/90* (2013.01); *C07D 495/04* (2013.01); *C07D 513/04* (2013.01)

(58) Field of Classification Search
CPC ... C07D 487/04; C07D 491/04; C07D 495/04; C07D 497/04; C07D 498/04; C07D 513/04; A61K 31/519
USPC ...... 544/254, 255, 256, 278, 280; 514/258.1, 514/261.1, 262.1, 265.1
See application file for complete search history.

(56) References Cited

U.S. PATENT DOCUMENTS

| | | | |
|---|---|---|---|
| 8,765,774 | B2 | 7/2014 | Gross et al. |
| 2010/0190747 | A1 | 7/2010 | Suzuki et al. |

FOREIGN PATENT DOCUMENTS

| | | |
|---|---|---|
| JP | 2011042611 | 3/2011 |
| WO | 9733890 A1 | 9/1997 |
| WO | 2007131680 A1 | 11/2007 |
| WO | 2010100189 A1 | 9/2010 |

OTHER PUBLICATIONS

International Search Report from corresponding PCT/EP2013/077061, mailed Feb. 5, 2014.

*Primary Examiner* — Venkataraman Balasubramanian
(74) *Attorney, Agent, or Firm* — McBee Moore Woodward Vanik, IP LLC

(57) ABSTRACT

The present invention relates to aryl sulphide and aryl sulphoxide derivatives, to their use as acaricides and insecticides for controlling animal pests and to processes and intermediates for their preparation. The aryl sulphide and aryl sulphoxide derivatives have the general structure (I)

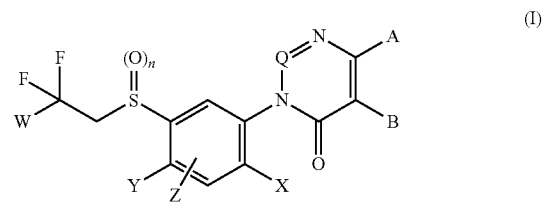

in which the respective radicals have the meanings given in the description.

24 Claims, No Drawings

ARYL SULFIDE DERIVATIVES AND ARYL SULFOXIDE DERIVATIVES AS ACARICIDES AND INSECTICIDES

CROSS REFERENCE TO RELATED APPLICATIONS

This application is a §371 National Stage Application of PCT/EP2013/077061, filed 18 Dec. 2013, which claims priority to EP 12198486.8, filed 20 Dec. 2012.

BACKGROUND

Field of the Invention

The present invention relates to aryl sulphide and aryl sulphoxide derivatives, to their use as acaricides and insecticides for controlling animal pests and to processes and intermediates for their preparation.

Description of Related Art

Various aryl sulphides and aryl sulphoxides and their insecticidal and acaricidal action are already known from WO 2007/131680 A, WO 2010/100189 A and JP 2011/42611.

On application, the active compounds already known from the publications mentioned above have disadvantages, for example in that they may have no or else only insufficient insecticidal and/or acaricidal activity against animal pests, in particular at low application rates.

SUMMARY

Accordingly, it is an object of the present invention to provide aryl sulphide and aryl sulphoxide derivatives which can be employed as insecticides and/or acaricides with satisfactory insecticidal and/or acaricidal activity against animal pests, in particular at low application rates, with high selectivity and improved compatibility in crops of useful plants.

The present invention now provides novel compounds of the formula (I)

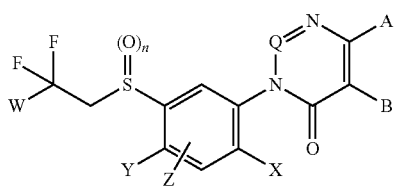

in which

A and B together with the carbon atoms to which they are attached represent an optionally substituted five-membered ring which may be interrupted by at least one or more heteroatoms;

W represents hydrogen or halogen;

Q represents C—V or nitrogen;

V represents hydrogen, hydroxy, halogen, cyano, alkyl, cycloalkyl, haloalkyl, alkoxy, haloalkoxy, alkylthio, haloalkylthio, alkylsulphinyl, haloalkylsulphinyl, alkylsulphonyl, haloalkylsulphonyl, amino, monoalkylamino or dialkylamino;

X, Y and Z independently of one another represent hydrogen, halogen, hydroxy, amino, cyano, nitro, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represent optionally substituted phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl;

or represent optionally substituted saturated or unsaturated cycloalkyl, cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl, cycloalkylalkylsulphonyl or cycloalkenyl;

or represent $NR^4R^5$, where $R^4$ and $R^5$ independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or $R^4$ and $R^5$ together with the nitrogen atom to which they are attached may form an optionally substituted saturated or unsaturated five- to eight-membered ring which is optionally interrupted by heteroatoms from the group consisting of O, S and N;

or represent a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulphinyl, alkylsulphonyl, alkylsulphonyloxy, haloalkylthio, haloalkylsulphinyl, haloalkylsulphonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulphonylamino, aminosulphonyl, alkylaminosulphonyl and dialkylaminosulphonyl, or by optionally substituted cycloalkyl, cycloalkoxy, cycloalkylalkyl or cycloalkylalkoxy which are optionally interrupted by heteroatoms from the group consisting of O, S and N;

or X and Y or Y and Z form, together with the carbon atoms to which they are attached, a 5- or 6-membered ring which is optionally substituted and optionally interrupted by heteroatoms from the group consisting of O, S, N and CO;

and n represents the number 0, 1 or 2.

DETAILED DESCRIPTION OF A PREFERRED EMBODIMENT

If appropriate, the compounds of the formula (I) may be present in various polymorphic forms or as mixtures of different polymorphic forms. Both the pure polymorphs and the polymorph mixtures are provided by the invention and can be used in accordance with the invention.

Depending on the substitution pattern, the compounds of the formula (I) have one or more centres of chirality, so that they may be present as mixtures of the enantiomers or diastereomers. If appropriate, the compounds of the formula (I) comprise pure enantiomers or diastereomers and mixtures thereof and the use of the pure enantiomers or diastereomers or mixtures thereof.

The formula (I) provides a general definition of the compounds according to the invention and also comprises all possible rotamers, tautomers and stereoisomers (cis/trans isomers) and mixtures thereof. Mention may be made, for example, of the tautomers of the general formula (I) where Q represents C—V and V represents hydroxy, thiol, amino or alkylamino.

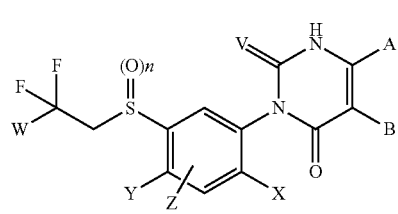

(I)

In a preferred embodiment of the present invention, the compounds have a structure of the general formula (I) in which A and B together with the carbon atoms to which they are attached represent a substructure selected from the group consisting of

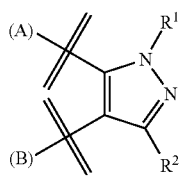

I-1

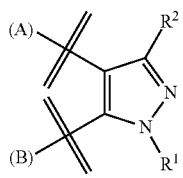

I-2

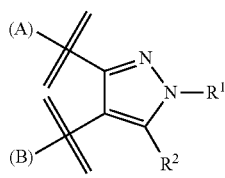

I-3

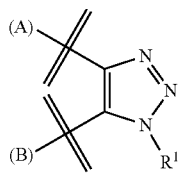

I-4

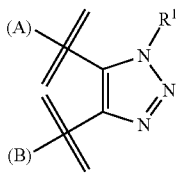

I-5

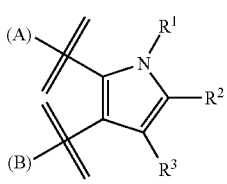

I-6

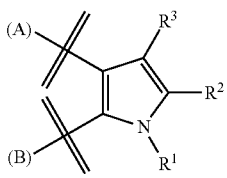

I-7

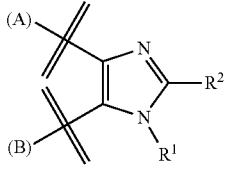

I-8

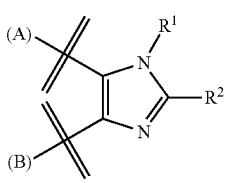

I-9

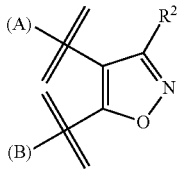

I-10

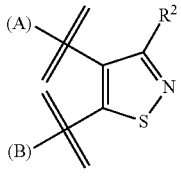

I-11

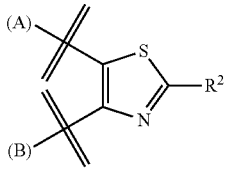

I-12

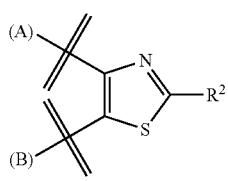 I-13

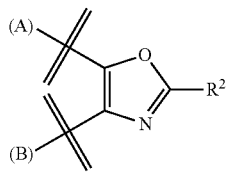 I-14

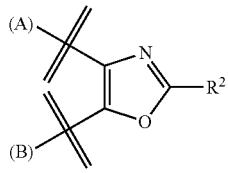 I-15

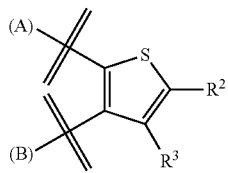 I-16

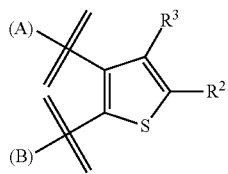 I-17

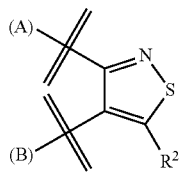 I-18

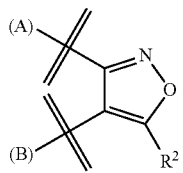 I-19

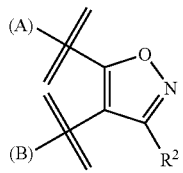 I-20

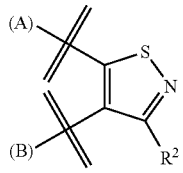 I-21

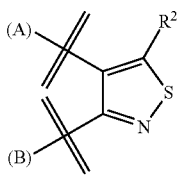 I-22

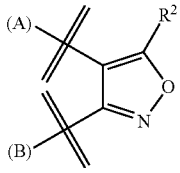 I-23 in which the labels (A) and (B) define the respective points of attachment of the radicals A and B of the general formula (I) and $R^1$, $R^2$ and $R^3$ have the following meanings:

$R^1$ represents hydrogen, optionally substituted alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkylcarbonyl, alkoxycarbonyl, haloalkoxycarbonyl, haloalkylcarbonyl, alkoxycarbonylalkyl, alkylthioalkyl, haloalkylthioalkyl, alkoxyalkylthioalkyl, alkylsulphinylalkyl, haloalkylsulphinylalkyl, alkoxyalkylsulphinylalkyl, alkylsulphonylalkyl, haloalkylsulphonylalkyl, alkoxyalkylsulphonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represents optionally substituted phenyl, phenylalkyl, phenoxyalkyl, phenylthioalkyl, hetaryl or hetarylalkyl;

or represents optionally substituted saturated or unsaturated cycloalkyl which may optionally be interrupted by one or more heteroatoms, or represents cycloalkylalkyl;

$R^2$ and $R^3$ independently of one another represent hydrogen, halogen, hydroxy, amino, cyano, nitro, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represent optionally substituted phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl;

or represent optionally substituted saturated or unsaturated cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl or cycloalkylalkylsulphonyl;

W represents hydrogen or halogen;

Q represents C—V or nitrogen;

V represents hydrogen, hydroxy, halogen, cyano, $(C_1-C_6)$-alkyl, $(C_3-C_8)$-cycloalkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphinyl, $(C_1-C_6)$-haloalkylsulphinyl, $(C_1-C_6)$-alkylsulphonyl, $(C_1-C_6)$-haloalkylsulphonyl, amino, $(C_1-C_6)$-alkylamino or $(C_1-C_6)$-dialkylamino;

X, Y and Z independently of one another represent hydrogen, halogen, hydroxy, amino, cyano, nitro, OCN, SCN, $SF_5$, tri-$(C_1-C_6)$-alkylsilyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_4)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, hydroxycarbonyl-$(C_1-C_4)$-alkoxy, $(C_1-C_7)$-alkoxycarbonyl-$(C_1-C_6)$-alkoxy, $(C_1-C_6)$-alkoxy-$(C_1-C_6)$-alkoxy, $(C_1-C_7)$-alkylhydroxyimino, $(C_1-C_7)$-alkoxyimino, $(C_1-C_6)$-alkyl-$(C_1-C_7)$-alkoxyimino, halo-$(C_1-C_6)$-alkyl-$(C_1-C_7)$-alkoxyimino, $(C_1-C_6)$-alkylthio, halo-$(C_1-C_6)$-alkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulphinyl, $(C_1-C_6)$-haloalkylsulphinyl, $(C_1-C_6)$-alkoxy-$(C_1-C_6)$-alkylsulphinyl, $(C_1-C_6)$-alkylsulphinyl-$(C_1-C_6)$-alkyl, $(C_1-C_6)$-alkylsulphonyl, $(C_1-C_6)$-haloalkylsulphonyl, $(C_1-C_6)$-alkoxy-$(C_1-C_6)$-alkylsulphonyl, $(C_1-C_6)$-alkylsulphonyl-$(C_1-C_6)$-alkyl, $(C_1-C_6)$-alkylsulphonyloxy, $(C_1-C_7)$-alkylcarbonyl, $(C_1-C_7)$-haloalkylcarbonyl, carboxyl, $(C_1-C_7)$-alkylcarbonyloxy, $(C_1-C_7)$-alkoxycarbonyl, $(C_1-C_7)$-haloalkoxycarbonyl, $(C_1-C_7)$-alkoxycarbonyl-$(C_1-C_6)$-alkyl, aminocarbonyl, $(C_1-C_7)$-alkylaminocarbonyl, di-$(C_1-C_7)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, $(C_1-C_6)$-alkylsulphoximino, aminothiocarbonyl, $(C_1-C_6)$-alkylaminothiocarbonyl or di-$(C_1-C_6)$-alkylaminothiocarbonyl;

or represent phenyl-$(C_1-C_6)$-alkyl, phenoxy, phenyl-$(C_1-C_4)$-alkyloxy, phenoxy-$(C_1-C_4)$-alkyl, phenylthio, phenylthio-$(C_1-C_4)$-alkyl, phenylsulphinyl, phenylsulphonyl, hetaryl-$(C_1-C_6)$-alkyl, hetaryloxy, hetaryl-$(C_1-C_4)$-alkyloxy, hetarylthio, hetarylsulphinyl, hetarylsulphonyl, optionally saturated or unsaturated $(C_3-C_8)$-cycloalkyl-$(C_1-C_6)$-alkyl, $(C_3-C_8)$-cycloalkyloxy, $(C_3-C_8)$-cycloalkyl-$(C_1-C_6)$-alkoxy, $(C_3-C_8)$-cycloalkylthio, $(C_3-C_8)$-cycloalkyl-$(C_1-C_6)$-alkylthio, $(C_3-C_8)$-cycloalkylsulphinyl, $(C_3-C_8)$-cycloalkyl-$(C_1-C_6)$-alkylsulphinyl, $(C_3-C_8)$-cycloalkylsulphonyl or $(C_3-C_8)$-cycloalkyl-$(C_1-C_6)$-alkylsulphonyl, substituted by optionally saturated or unsaturated $(C_3-C_8)$-cycloalkyl, $(C_3-C_8)$-cycloalkoxy, $(C_3-C_8)$-cycloalkyl-$(C_1-C_6)$-alkyl or $(C_3-C_8)$-cycloalkyl-$(C_1-C_6)$-alkoxy optionally substituted by identical or different substituents from the group consisting of halogen, cyano, nitro, hydroxy, amino, carboxy, $(C_1-C_6)$-alkyl, $(C_1-C_6)$-haloalkyl, $(C_2-C_7)$-alkenyl, $(C_2-C_7)$-haloalkenyl, $(C_2-C_6)$-alkynyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphonyloxy, $(C_1-C_6)$-haloalkylthio, $(C_1-C_6)$-haloalkylsulphinyl, $(C_1-C_6)$-haloalkylsulphonyl, $(C_1-C_6)$-alkylamino, di-$(C_1-C_6)$-alkylamino, $(C_1-C_7)$-alkylcarbonylamino, $(C_1-C_7)$-alkoxycarbonyl, $(C_1-C_7)$-alkylcarbonyl, $(C_1-C_7)$-alkylcarbonyloxy, aminocarbonyl, $(C_1-C_6)$-alkylaminocarbonyl, di-$(C_1-C_6)$-alkylaminocarbonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylsulphonylamino, aminosulphonyl, $(C_1-C_6)$-alkylaminosulphonyl and di-$(C_1-C_6)$-alkylaminosulphonyl and optionally interrupted by one or two heteroatoms from the group consisting of O, S and N;

or represent $NR^4R^5$ where $R^4$ and $R^5$ independently of one another represent hydrogen, cyano, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkyl-$(C_1-C_6)$-thioalkyl, $(C_2-C_7)$-alkenyl, $(C_2-C_7)$-haloalkenyl, $(C_2-C_7)$-cyanoalkenyl, $(C_2-C_6)$-alkynyl, $(C_2-C_6)$-haloalkynyl, $(C_2-C_6)$-cyanoalkynyl, acyl, $(C_1-C_7)$-alkoxycarbonyl or $R^4$ and $R^5$ together with the nitrogen atom to which they are attached may form a saturated or unsaturated five- to seven-membered ring which is optionally substituted by identical or different substituents from the group consisting of halogen, cyano, hydroxy, amino, $(C_1-C_6)$-alkyl, $(C_1-C_6)$-haloalkyl, $(C_1-C_6)$-alkoxy, $(C_1-C_6)$-haloalkoxy or by $(C_3-C_8)$-cycloalkyl or $(C_3-C_8)$-cycloalkyl-$(C_1-C_6)$-alkyl optionally substituted by identical or different substituents from the group consisting of halogen, cyano, $(C_1-C_6)$-alkyl, $(C_1-C_6)$-alkoxy, $(C_1-C_6)$-haloalkyl and optionally interrupted by heteroatoms from the group consisting of O, S and N and is optionally interrupted by heteroatoms from the group consisting of O, S and N;

or represent $(C_3-C_8)$-cycloalkyl, $(C_3-C_8)$-cycloalkoxy, $(C_3-C_8)$-cycloalkyl-$(C_1-C_4)$-alkyl, $(C_3-C_8)$-cycloalkyl-$(C_1-C_6)$-alkoxy, $(C_3-C_8)$-cycloalkylthio, $(C_3-C_8)$-cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl which is optionally mono- or polysubstituted by identical or different substituents from the group consisting of halogen, cyano, nitro, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphonyloxy, $(C_1-C_6)$-haloalkylthio, $(C_1-C_6)$-haloalkylsulphinyl, $(C_1-C_6)$-haloalkylsulphonyl, or by $(C_3-C_8)$-cycloalkyl, $(C_3-C_8)$-cycloalkoxy, $(C_3-C_8)$-cycloalkyl-$(C_1-C_4)$-alkyl, $(C_3-C_8)$-cycloalkyl-$(C_1-C_6)$-alkoxy, $(C_3-C_8)$-cycloalkylthio and $(C_3-C_8)$-cycloalkenyl, optionally substituted by halogen, cyano, $(C_1-C_6)$-alkyl, $(C_1-C_6)$-alkoxy, $(C_1-C_6)$-haloalkyl and optionally interrupted by heteroatoms from the group consisting of O, S and N;

or X and Z or Y and Z may form the following 5- or 6-membered rings which are optionally substituted by identical or different substituents from the group consisting of halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy and $(C_1-C_6)$-haloalkoxy

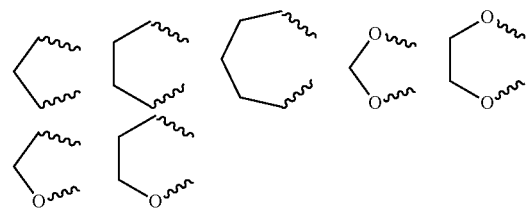

or X and Z or Y and Z may form the following fused rings which are optionally mono- or polysubstituted by identical or different substituents, where the substituents independently of one another may be selected from the group consisting of hydrogen, halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy, $(C_1-C_6)$-haloalkoxy, $(C_1-C_6)$-alkoxy-$(C_1-C_6)$-alkyl, $(C_1-C_6)$-alkylthio, $(C_1-C_6)$-alkylsulphonyl, amino, $(C_1-C_6)$-alkylamino, di-$(C_1-C_6)$-alkylamino and $(C_3-C_8)$-cycloalkylamino,

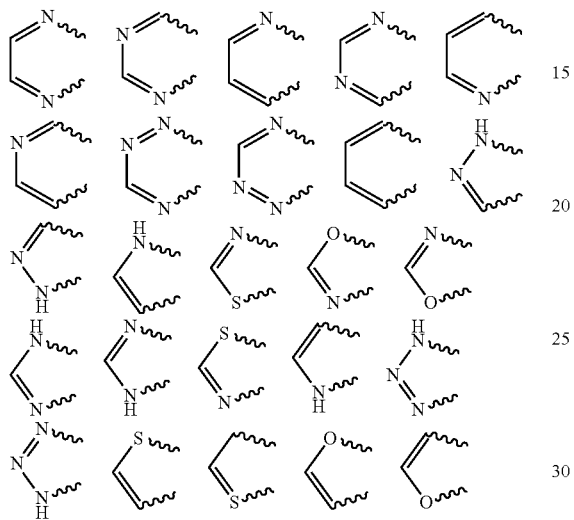

and n represents the number 0, 1 or 2.

In a further preferred embodiment of the present invention, the compounds have a structure of the general formula (I) in which A and B together with the carbon atoms to which they are attached represent a substructure selected from the group consisting of

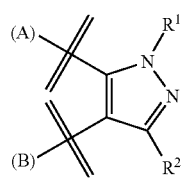

I-1

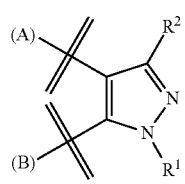

I-2

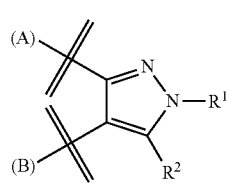

I-3

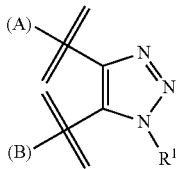

I-4

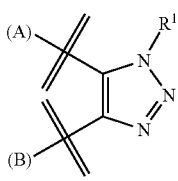

I-5

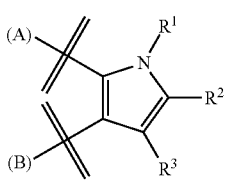

I-6

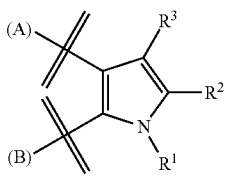

I-7

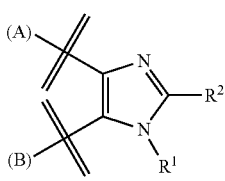

I-8

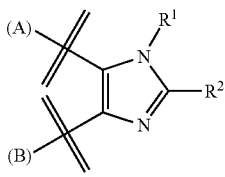

I-9

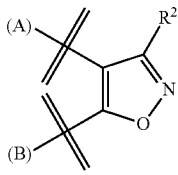

I-10

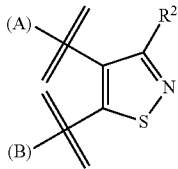

I-11

-continued

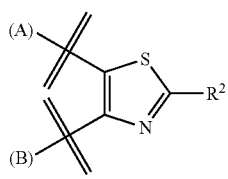
I-12

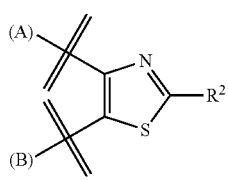
I-13

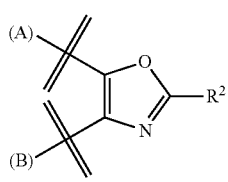
I-14

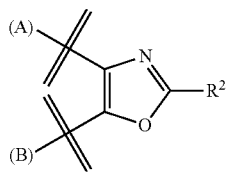
I-15

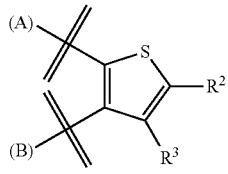
I-16

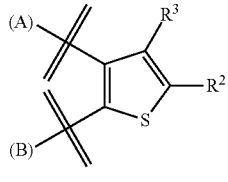
I-17

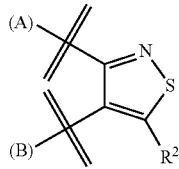
I-18

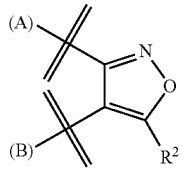
I-19

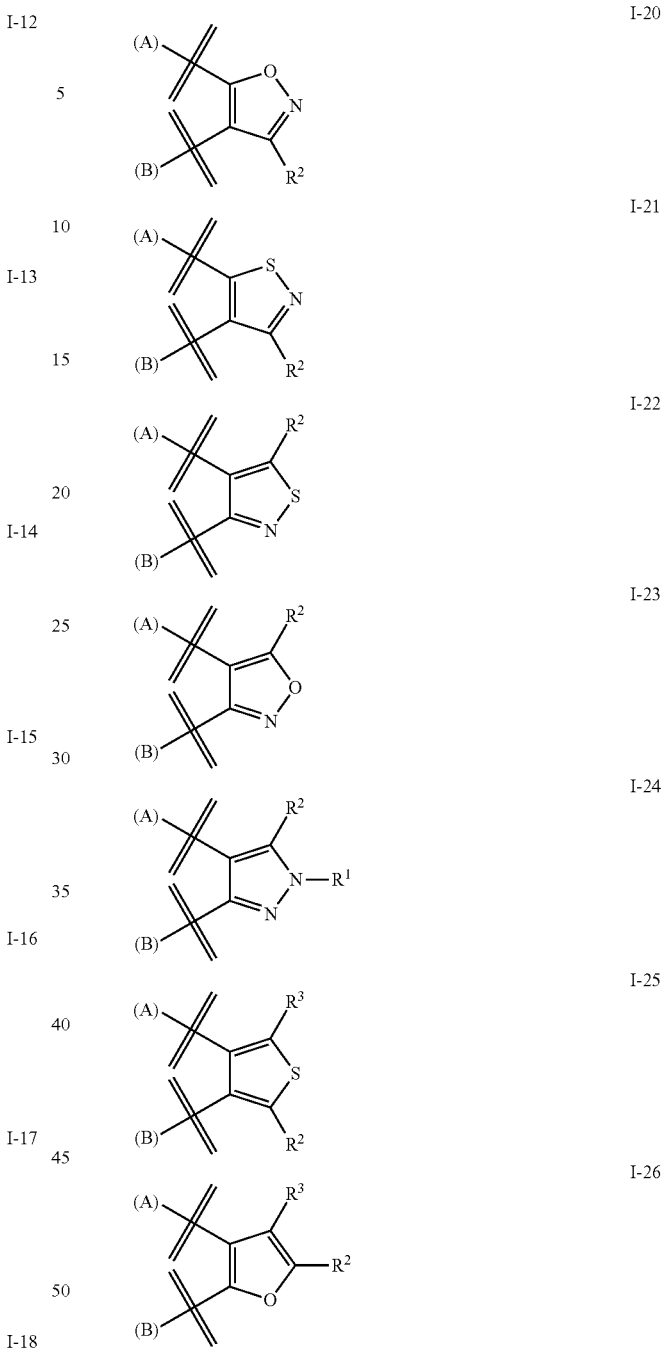

in which the labels (A) and (B) define the respective points of attachment of the radicals A and B of the general formula (I) and $R^1$, $R^2$ and $R^3$ have the following meanings:

$R^1$ represents hydrogen, optionally substituted alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkylcarbonyl, alkoxycarbonyl, haloalkoxycarbonyl, haloalkylcarbonyl, alkoxycarbonylalkyl, alkylthioalkyl, haloalkylthioalkyl, alkoxyalkylthioalkyl, alkylsulphinylalkyl, haloalkylsulphinylalkyl, alkoxyalkylsulphinylalkyl, alkylsulphonylalkyl, haloalkylsulphonylalkyl, alkoxyalkylsulphonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represents optionally substituted phenyl, phenylalkyl, phenoxyalkyl, phenylthioalkyl, hetaryl or hetarylalkyl;

or represents optionally substituted saturated or unsaturated cycloalkyl which may optionally be interrupted by one or more heteroatoms, or represents cycloalkylalkyl;

$R^2$ and $R^3$ independently of one another represent hydrogen, halogen, hydroxy, amino, cyano, nitro, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represent optionally substituted phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl;

or represent optionally substituted saturated or unsaturated cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl or cycloalkylalkylsulphonyl;

W represents hydrogen or halogen;

Q represents C—V or nitrogen;

V represents hydrogen, hydroxy, halogen, cyano, $(C_1-C_6)$-alkyl, $(C_3-C_8)$-cycloalkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphinyl, $(C_1-C_6)$-haloalkylsulphinyl, $(C_1-C_6)$-alkylsulphonyl, $(C_1-C_6)$-haloalkylsulphonyl, amino, $(C_1-C_6)$-alkylamino or $(C_1-C_6)$-dialkylamino;

X, Y and Z independently of one another represent hydrogen, halogen, hydroxy, amino, cyano, nitro, OCN, SCN, $SF_5$, tri-$(C_1-C_6)$-alkylsilyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_4)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, hydroxycarbonyl-$(C_1-C_4)$-alkoxy, $(C_1-C_7)$-alkoxycarbonyl-$(C_1-C_6)$-alkoxy, $(C_1-C_6)$-alkoxy-$(C_1-C_6)$-alkoxy, $(C_1-C_7)$-alkylhydroxyimino, $(C_1-C_7)$-alkoxyimino, $(C_1-C_6)$-alkyl-$(C_1-C_7)$-alkoxyimino, halo-$(C_1-C_6)$-alkyl-$(C_1-C_7)$-alkoxyimino, $(C_1-C_6)$-alkylthio, halo-$(C_1-C_6)$-alkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulphinyl, $(C_1-C_6)$-haloalkylsulphinyl, $(C_1-C_6)$-alkoxy-$(C_1-C_6)$-alkylsulphinyl, $(C_1-C_6)$-alkylsulphinyl-$(C_1-C_6)$-alkyl, $(C_1-C_6)$-alkylsulphonyl, $(C_1-C_6)$-haloalkylsulphonyl, $(C_1-C_6)$-alkoxy-$(C_1-C_6)$-alkylsulphonyl, $(C_1-C_6)$-alkylsulphonyl-$(C_1-C_6)$-alkyl, $(C_1-C_6)$-alkylsulphonyloxy, $(C_1-C_7)$-alkylcarbonyl, $(C_1-C_7)$-haloalkylcarbonyl, carboxyl, $(C_1-C_7)$-alkylcarbonyloxy, $(C_1-C_7)$-alkoxycarbonyl, $(C_1-C_7)$-haloalkoxycarbonyl, $(C_1-C_7)$-alkoxycarbonyl-$(C_1-C_6)$-alkyl, aminocarbonyl, $(C_1-C_7)$-alkylaminocarbonyl, di-$(C_1-C_7)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, $(C_1-C_6)$-alkylsulphoximino, aminothiocarbonyl, $(C_1-C_6)$-alkylaminothiocarbonyl or di-$(C_1-C_6)$-alkylaminothiocarbonyl;

or represent phenyl-$(C_1-C_6)$-alkyl, phenoxy, phenyl-$(C_1-C_4)$-alkyloxy, phenoxy-$(C_1-C_4)$-alkyl, phenylthio, phenylthio-$(C_1-C_4)$-alkyl, phenylsulphinyl, phenylsulphonyl, hetaryl-$(C_1-C_6)$-alkyl, hetaryloxy, hetaryl-$(C_1-C_4)$-alkyloxy, hetarylthio, hetarylsulphinyl, hetarylsulphonyl, optionally saturated or unsaturated $(C_3-C_8)$-cycloalkyl-$(C_1-C_6)$-alkyl, $(C_3-C_8)$-cycloalkyloxy, $(C_3-C_8)$-cycloalkyl-$(C_1-C_6)$-alkoxy, $(C_3-C_8)$-cycloalkylthio, $(C_3-C_8)$-cycloalkyl-$(C_1-C_6)$-alkylthio, $(C_3-C_8)$-cycloalkylsulphinyl, $(C_3-C_8)$-cycloalkyl-$(C_1-C_6)$-alkylsulphinyl, $(C_3-C_8)$-cycloalkylsulphonyl or $(C_3-C_8)$-cycloalkyl-$(C_1-C_6)$-alkylsulphonyl, substituted by optionally saturated or unsaturated $(C_3-C_8)$-cycloalkyl, $(C_3-C_8)$-cycloalkoxy, $(C_3-C_8)$-cycloalkyl-$(C_1-C_6)$-alkyl or $(C_3-C_8)$-cycloalkyl-$(C_1-C_6)$-alkoxy optionally substituted by identical or different substituents from the group consisting of halogen, cyano, nitro, hydroxy, amino, carboxy, $(C_1-C_6)$-alkyl, $(C_1-C_6)$-haloalkyl, $(C_2-C_7)$-alkenyl, $(C_2-C_7)$-haloalkenyl, $(C_2-C_6)$-alkynyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphonyloxy, $(C_1-C_6)$-haloalkylthio, $(C_1-C_6)$-haloalkylsulphinyl, $(C_1-C_6)$-haloalkylsulphonyl, $(C_1-C_6)$-alkylamino, di-$(C_1-C_6)$-alkylamino, $(C_1-C_7)$-alkylcarbonylamino, $(C_1-C_7)$-alkoxycarbonyl, $(C_1-C_7)$-alkylcarbonyl, $(C_1-C_7)$-alkylcarbonyloxy, aminocarbonyl, $(C_1-C_6)$-alkylaminocarbonyl, di-$(C_1-C_6)$-alkylaminocarbonyl, aminothiocarbonyl, $(C_1-C_6)$-alkylaminothiocarbonyl, di-$(C_1-C_6)$-alkylaminothiocarbonyl, $(C_3-C_8)$-cycloalkylamino, $(C_1-C_6)$-alkylsulphonylamino, aminosulphonyl, $(C_1-C_6)$-alkylaminosulphonyl and di-$(C_1-C_6)$-alkylaminosulphonyl and optionally interrupted by one or two heteroatoms from the group consisting of O, S and N;

or represent $NR^4R^5$ where $R^4$ and $R^5$ independently of one another represent hydrogen, cyano, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxy-$(C_1-C_6)$-alkyl, $(C_1-C_6)$-alkyl-$(C_1-C_6)$-thioalkyl, $(C_2-C_7)$-alkenyl, $(C_2-C_7)$-haloalkenyl, $(C_2-C_7)$-cyanoalkenyl, $(C_2-C_6)$-alkynyl, $(C_2-C_6)$-haloalkynyl, $(C_2-C_6)$-cyanoalkynyl, acyl, $(C_1-C_7)$-alkoxycarbonyl or $R^4$ and $R^5$ together with the nitrogen atom to which they are attached may form a saturated or unsaturated five- to seven-membered ring which is optionally substituted by identical or different substituents from the group consisting of halogen, cyano, hydroxy, amino, $(C_1-C_6)$-alkyl, $(C_1-C_6)$-haloalkyl, $(C_1-C_6)$-alkoxy, $(C_1-C_6)$-haloalkoxy or by $(C_3-C_8)$-cycloalkyl or $(C_3-C_8)$-cycloalkyl-$(C_1-C_6)$-alkyl optionally substituted by identical or different substituents from the group consisting of halogen, cyano, $(C_1-C_6)$-alkyl, $(C_1-C_6)$-alkoxy, $(C_1-C_6)$-haloalkyl and optionally interrupted by heteroatoms from the group consisting of O, S and N and is optionally interrupted by heteroatoms from the group consisting of O, S and N;

or represent $(C_3-C_8)$-cycloalkyl, $(C_3-C_8)$-cycloalkoxy, $(C_3-C_8)$-cycloalkyl-$(C_1-C_4)$-alkyl, $(C_3-C_8)$-cycloalkyl-$(C_1-C_6)$-alkoxy, $(C_3-C_8)$-cycloalkylthio, $(C_3-C_8)$-cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl which is optionally mono- or polysubstituted by identical or different substituents from the group consisting of halogen, cyano, nitro, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulphinyl, $(C_1-C_6)$-alkylsulphonyl, $(C_1-C_6)$-alkylsulphonyloxy, $(C_1-C_6)$-haloalkylthio, $(C_1-C_6)$-haloalkylsulphinyl, $(C_1-C_6)$-haloalkylsulphonyl, or by $(C_3-C_8)$-cycloalkyl, $(C_3-C_8)$-cycloalkoxy, $(C_3-C_8)$-cycloalkyl-$(C_1-C_4)$-alkyl, $(C_3-C_8)$-cycloalkyl-$(C_1-C_6)$-alkoxy, $(C_3-C_8)$-cycloalkylthio and $(C_3-C_8)$-cycloalkenyl, optionally substituted by halogen, cyano, $(C_1-C_6)$-alkyl, $(C_1-C_6)$-alkoxy, $(C_1-C_6)$-haloalkyl and optionally interrupted by heteroatoms from the group consisting of O, S and N;

or X and Z or Y and Z may form the following 5- or 6-membered rings which are optionally substituted by identical or different substituents from the group consisting of halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy and $(C_1-C_6)$-haloalkoxy

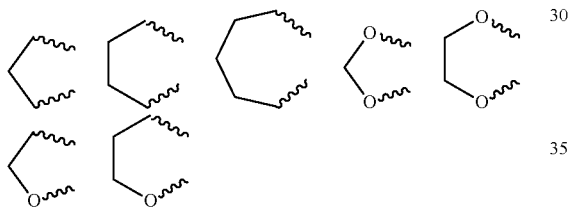

or X and Z or Y and Z may form the following fused rings which are optionally mono- or polysubstituted by identical or different substituents, where the substituents independently of one another may be selected from the group consisting of hydrogen, halogen, cyano, $(C_1-C_6)$-alkyl, $(C_3-C_8)$-cycloalkyl, $(C_1-C_6)$-haloalkyl, $(C_3-C_8)$-halocycloalkyl, $(C_1-C_6)$-alkoxy, $(C_1-C_6)$-haloalkoxy, $(C_1-C_6)$-alkoxy-$(C_1-C_6)$-alkyl, $(C_1-C_6)$-alkylthio, $(C_1-C_6)$-alkylsulphonyl, amino, $(C_1-C_6)$-alkylamino, di-$(C_1-C_6)$-alkylamino and $(C_3-C_8)$-cycloalkylamino,

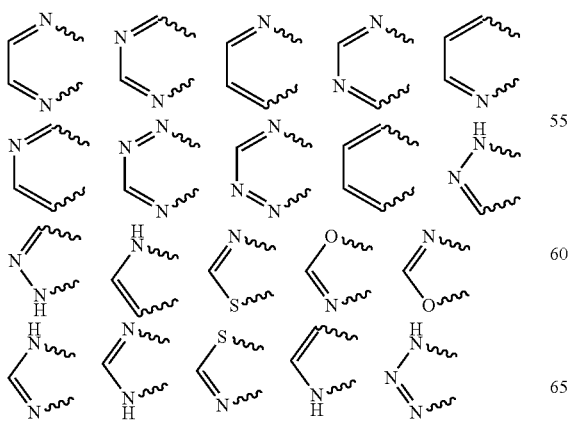

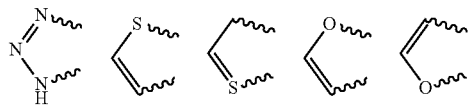

and n represents the number 0, 1 or 2.

In a particularly preferred embodiment of the present invention, the compounds according to the invention have a structure of the general formula (I) in which A and B together with the carbon atoms to which they are attached represent a substructure selected from the group consisting of

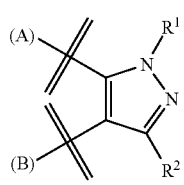

I-1

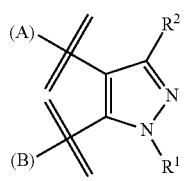

I-2

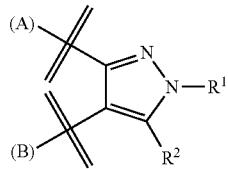

I-3

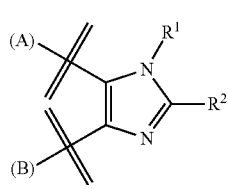

I-9

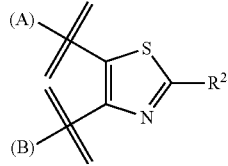

I-12

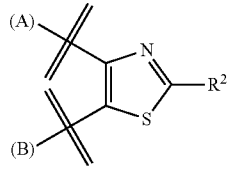

I-13

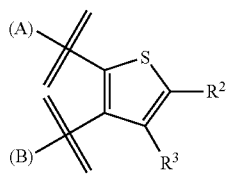

I-16

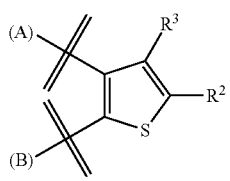

I-17

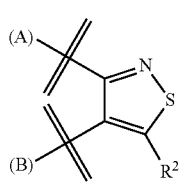

I-18 in which the labels (A) and (B) define the respective points of attachment of the radicals A and B of the general formula (I) and $R^1$, $R^2$ and $R^3$ have the following meanings:

$R^1$ represents hydrogen, $(C_1-C_6)$-alkyl, $(C_1-C_6)$-haloalkyl, cyano-$(C_1-C_6)$-alkyl, hydroxy-$(C_1-C_6)$-alkyl, $(C_1-C_6)$-alkoxycarbonyl-$(C_1-C_6)$-alkyl, $(C_1-C_6)$-alkoxy-$(C_1-C_6)$-alkyl, $(C_2-C_7)$-alkenyl, halo-$(C_2-C_7)$-alkenyl, cyano-$(C_2-C_7)$-alkenyl, $(C_2-C_6)$-alkynyl, halo-$(C_2-C_6)$-alkynyl, cyano-$(C_2-C_6)$-alkynyl, $(C_1-C_6)$-alkylcarbonyl, $(C_1-C_6)$-alkoxycarbonyl, halo-$(C_1-C_6)$-alkoxycarbonyl, halo-$(C_1-C_6)$-alkylcarbonyl, $(C_1-C_6)$-alkoxycarbonyl-$(C_1-C_6)$-alkyl, $(C_1-C_6)$-alkylthio-$(C_1-C_6)$-alkyl, halo-$(C_1-C_6)$-alkylthio-$(C_1-C_6)$-alkyl, $(C_1-C_6)$-alkoxy-$(C_1-C_6)$-alkylthio-$(C_1-C_6)$-alkyl, $(C_1-C_6)$-alkylsulphinyl-$(C_1-C_6)$-alkyl, halo-$(C_1-C_6)$-alkylsulphinyl-$(C_1-C_6)$-alkyl, $(C_1-C_6)$-alkoxy-$(C_1-C_6)$-alkylsulphinyl-$(C_1-C_6)$-alkyl, $(C_1-C_6)$-alkylsulphonyl-$(C_1-C_6)$-alkyl, halo-$(C_1-C_6)$-alkylsulphonyl-$(C_1-C_6)$-alkyl, $(C_1-C_6)$-alkoxy-$(C_1-C_6)$-alkylsulphonyl-$(C_1-C_6)$-alkyl, aminocarbonyl, $(C_1-C_6)$-alkylaminocarbonyl, di-$(C_1-C_6)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, aminothiocarbonyl, $(C_1-C_6)$-alkylaminothiocarbonyl or di-$(C_1-C_6)$-alkylaminothiocarbonyl;

or represents phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represents $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl;

$R^2$ and $R^3$ independently of one another represent hydrogen, halogen, hydroxy, amino, cyano, nitro, OCN, SCN, $SF_5$, trialkylsilyl, $(C_1-C_6)$-alkyl, $(C_1-C_6)$-haloalkyl, cyano-$(C_1-C_6)$-alkyl, hydroxy-$(C_1-C_6)$-alkyl, $(C_1-C_6)$-alkoxycarbonyl-$(C_1-C_6)$-alkyl, $(C_1-C_6)$-alkoxy-$(C_1-C_6)$-alkyl, $(C_2-C_7)$-alkenyl, halo-$(C_2-C_7)$-alkenyl, cyano-$(C_2-C_7)$-alkenyl, $(C_2-C_6)$-alkynyl, halo-$(C_2-C_6)$-alkynyl, cyano-$(C_2-C_6)$-alkynyl, $(C_1-C_6)$-alkylcarbonyl, $(C_1-C_6)$-alkoxycarbonyl, halo-$(C_1-C_6)$-alkoxycarbonyl, halo-$(C_1-C_6)$-alkylcarbonyl, $(C_1-C_6)$-alkoxycarbonyl-$(C_1-C_6)$-alkyl, $(C_1-C_6)$-alkylthio-$(C_1-C_6)$-alkyl, halo-$(C_1-C_6)$-alkylthio-$(C_1-C_6)$-alkyl, $(C_1-C_6)$-alkoxy-$(C_1-C_6)$-alkylthio-$(C_1-C_6)$-alkyl, $(C_1-C_6)$-alkylsulphinyl-$(C_1-C_6)$-alkyl, halo-$(C_1-C_6)$-alkylsulphinyl-$(C_1-C_6)$-alkyl, $(C_1-C_6)$-alkoxy-$(C_1-C_6)$-alkylsulphinyl-$(C_1-C_6)$-alkyl, $(C_1-C_6)$-alkylsulphonyl-$(C_1-C_6)$-alkyl, halo-$(C_1-C_6)$-alkylsulphonyl-$(C_1-C_6)$-alkyl, $(C_1-C_6)$-alkoxy-$(C_1-C_6)$-alkylsulphonyl-$(C_1-C_6)$-alkyl, aminocarbonyl, $(C_1-C_6)$-alkylaminocarbonyl, di-$(C_1-C_6)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, $(C_1-C_6)$-alkylsulphoximino, aminothiocarbonyl, $(C_1-C_6)$-alkylaminothiocarbonyl or di-$(C_1-C_6)$-alkylaminothiocarbonyl;

or represent phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represent $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or $(C_3-C_6)$-cycloalkyl;

Q represents C—V or nitrogen; where

V represents hydrogen, halogen, $(C_1-C_4)$-alkyl or $(C_1-C_4)$-haloalkyl;

W represents hydrogen or fluorine;

X, Y and Z independently of one another represent hydrogen, fluorine, chlorine, bromine, cyano, nitro, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy or aminothiocarbonyl;

or represent phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represent (C$_3$-C$_6$)-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, (C$_1$-C$_4$)-alkyl, (C$_1$-C$_4$)-haloalkyl, (C$_1$-C$_4$)-alkoxy, (C$_1$-C$_4$)-haloalkoxy or (C$_3$-C$_6$)-cycloalkyl;

n represents the number 0 or 1.

In a further particularly preferred embodiment of the present invention, the compounds according to the invention have a structure of the general formula (I) in which A and B together with the carbon atoms to which they are attached represent a substructure selected

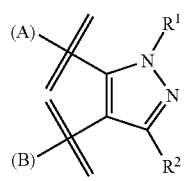
I-1

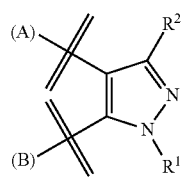
I-2

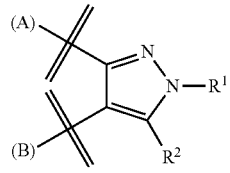
I-3

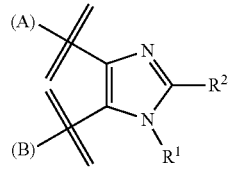
I-8

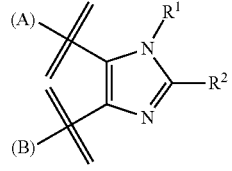
I-9

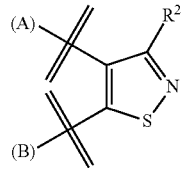
I-11

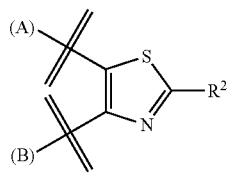
I-12

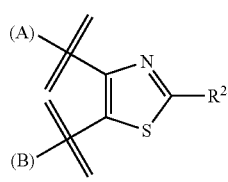
I-13

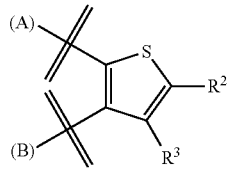
I-16

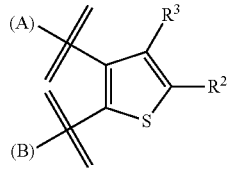
I-17

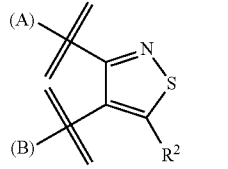
I-18

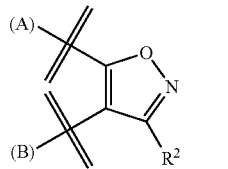
I-20

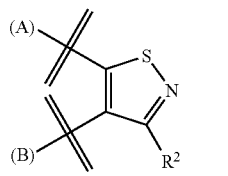
I-21

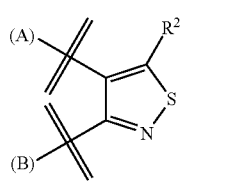
I-22

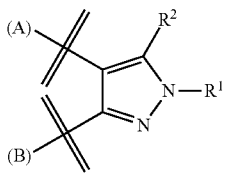

I-24

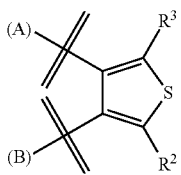

I-25

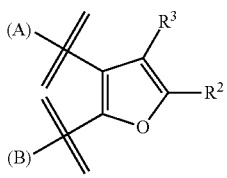

I-26 in which the labels (A) and (B) define the respective points of attachment of the radicals A and B of the general formula (I) and $R^1$, $R^2$ and $R^3$ have the following meanings:

$R^1$ represents hydrogen, $(C_1-C_6)$-alkyl, $(C_1-C_6)$-haloalkyl, cyano-$(C_1-C_6)$-alkyl, hydroxy-$(C_1-C_6)$-alkyl, $(C_1-C_6)$-alkoxycarbonyl-$(C_1-C_6)$-alkyl, $(C_1-C_6)$-alkoxy-$(C_1-C_6)$-alkyl, $(C_3-C_6)$-cycloalkyl-$(C_1-C_3)$-alkyl, $(C_2-C_7)$-alkenyl, halo-$(C_2-C_7)$-alkenyl, cyano-$(C_2-C_7)$-alkenyl, $(C_2-C_6)$-alkynyl, halo-$(C_2-C_6)$-alkynyl, cyano-$(C_2-C_6)$-alkynyl, $(C_1-C_6)$-alkylcarbonyl, $(C_1-C_6)$-alkoxycarbonyl, halo-$(C_1-C_6)$-alkoxycarbonyl, halo-$(C_1-C_6)$-alkylcarbonyl, $(C_1-C_6)$-alkoxycarbonyl-$(C_1-C_6)$-alkyl, $(C_1-C_6)$-alkylthio-$(C_1-C_6)$-alkyl, halo-$(C_1-C_6)$-alkylthio-$(C_1-C_6)$-alkyl, $(C_1-C_6)$-alkoxy-$(C_1-C_6)$-alkylthio-$(C_1-C_6)$-alkyl, $(C_1-C_6)$-alkylsulphinyl-$(C_1-C_6)$-alkyl, halo-$(C_1-C_6)$-alkylsulphinyl-$(C_1-C_6)$-alkyl, $(C_1-C_6)$-alkoxy-$(C_1-C_6)$-alkylsulphinyl-$(C_1-C_6)$-alkyl, $(C_1-C_6)$-alkylsulphonyl-$(C_1-C_6)$-alkyl, halo-$(C_1-C_6)$-alkylsulphonyl-$(C_1-C_6)$-alkyl, $(C_1-C_6)$-alkoxy-$(C_1-C_6)$-alkylsulphonyl-$(C_1-C_6)$-alkyl, aminocarbonyl, $(C_1-C_6)$-alkylaminocarbonyl, di-$(C_1-C_6)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, aminothiocarbonyl, $(C_1-C_6)$-alkylaminothiocarbonyl or di-$(C_1-C_6)$-alkylaminothiocarbonyl;

or represents phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represents $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy, $(C_3-C_6)$-cycloalkyl;

$R^2$ and $R^3$ independently of one another represent hydrogen, halogen, hydroxy, amino, cyano, nitro, OCN, SCN, $SF_5$, trialkylsilyl, $(C_1-C_6)$-alkyl, $(C_1-C_6)$-haloalkyl, cyano-$(C_1-C_6)$-alkyl, hydroxy-$(C_1-C_6)$-alkyl, $(C_1-C_6)$-alkoxycarbonyl-$(C_1-C_6)$-alkyl, $(C_1-C_6)$-alkoxy-$(C_1-C_6)$-alkyl, $(C_3-C_6)$-cycloalkyl-$(C_1-C_3)$-alkyl, $(C_2-C_7)$-alkenyl, halo-$(C_2-C_7)$-alkenyl, cyano-$(C_2-C_7)$-alkenyl, $(C_2-C_6)$-alkynyl, halo-$(C_2-C_6)$-alkynyl, cyano-$(C_2-C_6)$-alkynyl, $(C_1-C_6)$-alkylcarbonyl, $(C_1-C_6)$-alkoxycarbonyl, halo-$(C_1-C_6)$-alkoxycarbonyl, halo-$(C_1-C_6)$-alkylcarbonyl, $(C_1-C_6)$-alkoxycarbonyl-$(C_1-C_6)$-alkyl, $(C_1-C_6)$-alkylthio-$(C_1-C_6)$-alkyl, halo-$(C_1-C_6)$-alkylthio-$(C_1-C_6)$-alkyl, $(C_1-C_6)$-alkoxy-$(C_1-C_6)$-alkylthio-$(C_1-C_6)$-alkyl, $(C_1-C_6)$-alkylsulphinyl-$(C_1-C_6)$-alkyl, halo-$(C_1-C_6)$-alkylsulphinyl-$(C_1-C_6)$-alkyl, $(C_1-C_6)$-alkoxy-$(C_1-C_6)$-alkylsulphinyl-$(C_1-C_6)$-alkyl, $(C_1-C_6)$-alkylsulphonyl-$(C_1-C_6)$-alkyl, halo-$(C_1-C_6)$-alkylsulphonyl-$(C_1-C_6)$-alkyl, $(C_1-C_6)$-alkoxy-$(C_1-C_6)$-alkylsulphonyl-$(C_1-C_6)$-alkyl, aminocarbonyl, $(C_1-C_6)$-alkylaminocarbonyl, di-$(C_1-C_6)$-alkylaminocarbonyl, $(C_2-C_7)$-alkenylaminocarbonyl, di-$(C_2-C_7)$-alkenylaminocarbonyl, $(C_3-C_8)$-cycloalkylaminocarbonyl, $(C_1-C_6)$-alkylsulphonylamino, aminosulphonyl, $(C_1-C_6)$-alkylaminosulphonyl, di-$(C_1-C_6)$-alkylaminosulphonyl, $(C_1-C_6)$-alkylsulphoximino, aminothiocarbonyl, $(C_1-C_6)$-alkylaminothiocarbonyl or di-$(C_1-C_6)$-alkylaminothiocarbonyl;

or represent phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represent $(C_3-C_6)$-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or $(C_3-C_6)$-cycloalkyl;

Q represents C—V or nitrogen; where

V represents hydrogen, halogen, $(C_1-C_4)$-alkyl, hydroxy or $(C_1-C_4)$-haloalkyl;

W represents hydrogen or fluorine;

X, Y and Z independently of one another represent hydrogen, fluorine, chlorine, bromine, cyano, nitro, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy or aminothiocarbonyl;

or represent phenyl-$(C_1-C_4)$-alkyl, phenoxy, hetaryl-$(C_1-C_4)$-alkyl, hetaryloxy, optionally saturated or unsaturated $(C_3-C_6)$-cycloalkyl-$(C_1-C_4)$-alkyl, $(C_3-C_6)$-cycloalkyloxy or $(C_3-C_6)$-cycloalkyl-$(C_1-C_4)$-alkoxy, optionally mono- or disubstituted by identical or different substituents from the group consisting of fluorine, chlorine, bromine, cyano, nitro, $(C_1-C_4)$-alkyl, $(C_1-C_4)$-haloalkyl, $(C_1-C_4)$-alkoxy, $(C_1-C_4)$-haloalkoxy or by optionally saturated or unsaturated $(C_3-C_6)$-cycloalkyl which is optionally interrupted by a heteroatom from the group consisting of O, S and N;

or represent ($C_3$-$C_6$)-cycloalkyl, phenyl, pyridyl, pyrimidyl, pyridazinyl, pyrazinyl, triazinyl, thiazolyl, thiadiazolyl, oxazolyl, oxadiazolyl, pyrazolyl, triazolyl or tetrazolyl which is optionally mono- or disubstituted by identical or different substituents from the group consisting of fluorine, chlorine, bromine, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy or ($C_3$-$C_6$)-cycloalkyl;

n represents the number 0 or 1.

In a very particularly preferred embodiment of the present invention, the compounds according to the invention have a structure of the general formula (I) in which A and B together with the carbon atoms to which they are attached represent a substructure selected from the group consisting of I-1
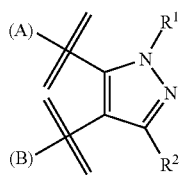

I-2
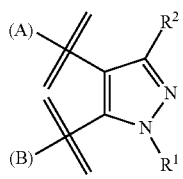

I-3
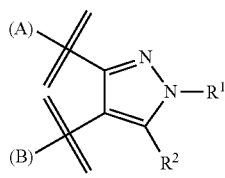

I-9
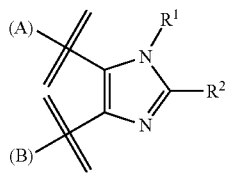

I-12
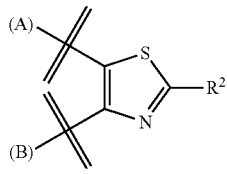

I-13
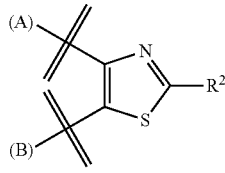

-continued

I-16
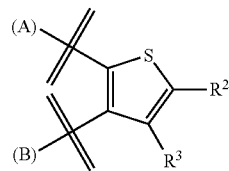

I-17
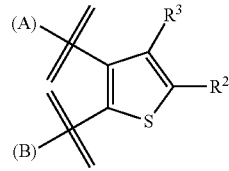

I-18
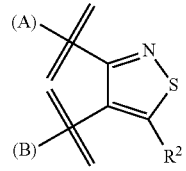

in which the labels (A) and (B) define the respective points of attachment of the radicals A and B of the general formula (I) and $R^1$, $R^2$ and $R^3$ have the following meanings:

$R^1$ represents hydrogen, methyl, ethyl, propyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represents cyclopropyl, cyclobutyl, cyclopentyl or cyclohexyl which are mono- or polysubstituted by identical or different substituents from the group consisting of fluorine, chlorine, bromine, cyano, nitro, methyl, ethyl and trifluoromethyl;

or represents cyclopropylmethyl or cyclobutylmethyl which are mono- or polysubstituted by identical or different substituents from the group consisting of fluorine, chlorine, bromine, cyano, nitro, methyl, ethyl and trifluoromethyl;

$R^2$ and $R^3$ independently of one another represent hydrogen, fluorine, chlorine, bromine, iodine, hydroxy, amino, cyano, nitro, OCN, SCN, $SF_5$, trimethylsilyl, methyl, ethyl, propyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represent cyclopropyl, cyclobutyl, cyclopentyl or cyclohexyl which are mono- or polysubstituted by identical or different substituents from the group consisting of fluorine, chlorine, bromine, cyano, nitro, methyl, ethyl and trifluoromethyl;

or represent cyclopropylmethyl or cyclobutylmethyl which are mono- or polysubstituted by identical or different substituents from the group consisting of fluorine, chlorine, bromine, cyano, nitro, methyl, ethyl and trifluoromethyl;

Q represents C—V or nitrogen; where

V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl, (2,2)-difluoroethyl;

W represents hydrogen or fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

In a further very particularly preferred embodiment of the present invention, the compounds according to the invention have a structure of the general formula (I) in which A and B together with the carbon atoms to which they are attached represent a substructure selected from the group consisting of

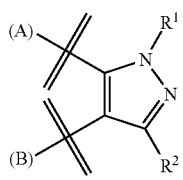
I-1

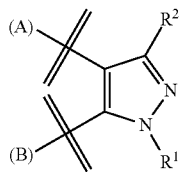
I-2

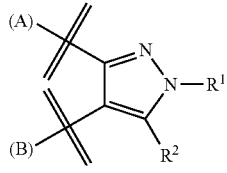
I-3

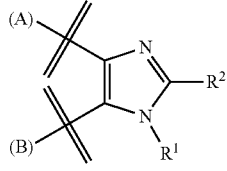
I-8

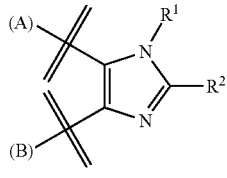
I-9

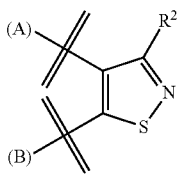
I-11

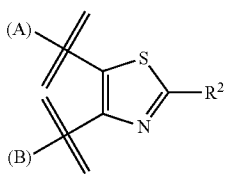
I-12

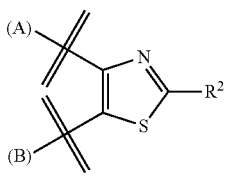
I-13

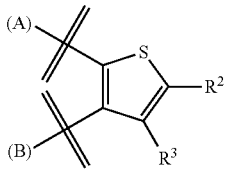
I-16

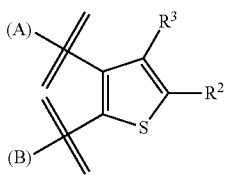
I-17

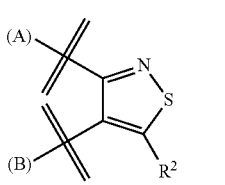
I-18

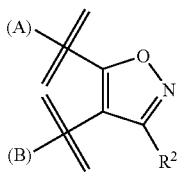
I-20

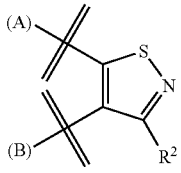
I-21

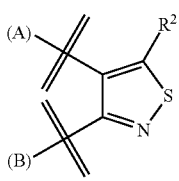 I-22

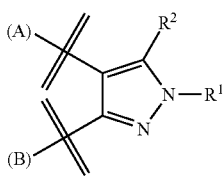 I-24

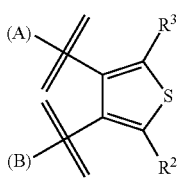 I-25

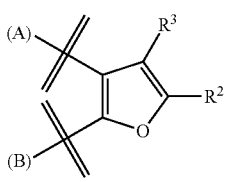 I-26 in which the labels (A) and (B) define the respective points of attachment of the radicals A and B of the general formula (I) and $R^1$, $R^2$ and $R^3$ have the following meanings:

$R^1$ represents hydrogen, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represents cyclopropyl, cyclobutyl, cyclopentyl or cyclohexyl which are mono- or polysubstituted by identical or different substituents from the group consisting of fluorine, chlorine, bromine, cyano, nitro, methyl, ethyl, methoxy, ethoxy, trifluoromethyl and cyclopropyl;

or represents cyclopropylmethyl or cyclobutylmethyl which are mono- or polysubstituted by identical or different substituents from the group consisting of fluorine, chlorine, bromine, cyano, nitro, methyl, ethyl, methoxy, ethoxy, trifluoromethyl and cyclopropyl;

$R^2$ and $R^3$ independently of one another represent hydrogen, fluorine, chlorine, bromine, iodine, hydroxy, amino, cyano, nitro, OCN, SCN, $SF_5$, trimethylsilyl, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methylcarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represent cyclopropyl, cyclobutyl, cyclopentyl or cyclohexyl which are mono- or polysubstituted by identical or different substituents from the group consisting of fluorine, chlorine, bromine, cyano, nitro, methyl, ethyl, methoxy, ethoxy, trifluoromethyl and cyclopropyl;

or represent cyclopropylmethyl or cyclobutylmethyl which are mono- or polysubstituted by identical or different substituents from the group consisting of fluorine, chlorine, bromine, cyano, nitro, methyl, ethyl, methoxy, ethoxy, trifluoromethyl and cyclopropyl;

Q represents C—V or nitrogen; where

V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl;

W represents hydrogen or fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

In a first aspect of the very particularly preferred embodiments of the present invention, the compounds according to the invention have a structure of the general formula (I) in which A and B together with the carbon atoms to which they are attached represent the radical

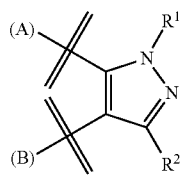 I-1 in which $R^1$ and $R^2$ have the meanings above, in particular hydrogen, methyl, ethyl, cyclopropyl or (2,2,2)-trifluoroethyl;

Q represents C—V or nitrogen; where

V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl or (2,2)-difluoroethyl;

W represents hydrogen or fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

In an alternative first aspect of the very particularly preferred embodiment of the present invention, the compounds according to the invention have a structure of the general formula (I) in which A and B together with the carbon atoms to which they are attached represent the radical

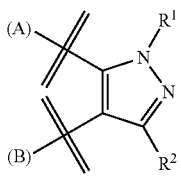

I-1 in which $R^1$ has the meaning above, in particular hydrogen, methyl, ethyl, isopropyl, tert-butyl, cyclopropyl, cyclopropylmethyl, trifluoromethyl or (2,2,2)-trifluoroethyl;

$R^2$ has the meaning above, in particular hydrogen, methyl, ethyl, isopropyl, tert-butyl, cyclopropyl, cyclopropylmethyl, trifluoromethyl or (2,2,2)-trifluoroethyl;

Q represents C—V or nitrogen; where
  V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl or (2,2)-difluoroethyl;
W represents hydrogen or fluorine, in particular fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.

In the context of these aspects, it is most preferred if
A and B together with the carbon atoms to which they are attached represent the radical (I-1),
$R^1$ represents methyl, ethyl or (2,2,2)-trifluoroethyl;
$R^2$ represents hydrogen or methyl;
Q represents C—V or nitrogen; where
  V represents hydrogen, methyl or trifluoromethyl;
W represents fluorine;
X represents hydrogen, fluorine, chlorine or methyl;
Y represents chlorine, methyl, trifluoromethyl or cyano;
  where X and Y represent in particular the following combinations (Y,X): (Me,F), (Me,Me), (Me,H), (Cl,Fl), (Cl,Cl), (Cl,H), (CF$_3$,H), (CN,H);
Z represents hydrogen;
n represents the number 0 or 1.

In a second aspect of the very particularly preferred embodiment of the present invention, the compounds according to the invention have a structure of the general formula (I) in which
A and B together with the carbon atoms to which they are attached represent the radical

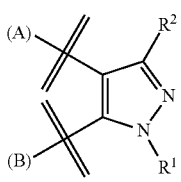

I-2 in which $R^1$ and $R^2$ have the meanings above, in particular hydrogen, methyl, ethyl, cyclopropyl or (2,2,2)-trifluoroethyl;

Q represents C—V or nitrogen; where
  V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl, (2,2)-difluoroethyl;
W represents hydrogen or fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative second aspect of the very particularly preferred embodiment of the present invention, the compounds according to the invention have a structure of the general formula (I) in which
A and B together with the carbon atoms to which they are attached represent the radical

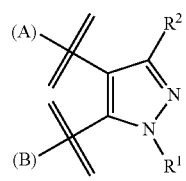

I-2 in which $R^1$ has the meaning above, in particular hydrogen, methyl, ethyl, isopropyl, tert-butyl, cyclopropyl, cyclopropylmethyl, trifluoromethyl or (2,2,2)-trifluoroethyl;

$R^2$ has the meaning above, in particular hydrogen, methyl, ethyl, isopropyl, tert-butyl, cyclopropyl, cyclopropylmethyl, trifluoromethyl or (2,2,2)-trifluoroethyl;

Q represents C—V or nitrogen; where
  V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl or (2,2)-difluoroethyl;
W represents hydrogen or fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.

In the context of these aspects, it is most preferred if
A and B together with the carbon atoms to which they are attached represent the radical (I-2);
$R^1$ represents methyl, ethyl, isopropyl or cyclopropylmethyl;
$R^2$ represents hydrogen or methyl;
Q represents C—V or nitrogen; where
  V represents hydrogen, methyl or ethyl;
W represents fluorine;
X represents hydrogen, fluorine, chlorine or methyl;
Y represents chlorine or methyl;

where X and Y represent in particular the following combinations (Y,X): (Me,F), (Me,Cl), (Me,Me), (Me,H), (Cl,Fl), (Cl,Cl);
Z represents hydrogen;
n represents the number 0 or 1.

In a third aspect of the very particularly preferred embodiment of the present invention, the compounds according to the invention have a structure of the general formula (I) in which
A and B together with the carbon atoms to which they are attached represent the radical

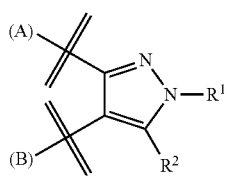

I-3 in which $R^1$ and $R^2$ have the meanings above, in particular hydrogen, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative third aspect of the very particularly preferred embodiment of the present invention, the compounds according to the invention have a structure of the general formula (I) in which
A and B together with the carbon atoms to which they are attached represent the radical

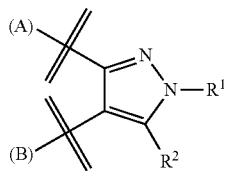

I-3 in which $R^1$ has the meaning above, in particular hydrogen, methyl, ethyl, isopropyl, tert-butyl, cyclopropyl, cyclopropylmethyl, trifluoromethyl or (2,2,2)-trifluoroethyl;
$R^2$ has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.

In the context of these aspects, it is most preferred if
A and B together with the carbon atoms to which they are attached represent the radical (I-3);
$R^1$ represents methyl;
$R^2$ represents hydrogen or methyl;
Q represents C—V; where
V represents hydrogen or trifluoromethyl;
W represents fluorine;
X represents hydrogen or fluorine;
Y represents chlorine, methyl, trifluoromethyl or cyano;
where X and Y represent in particular the following combinations (Y,X): (Me,F), (Me,H), (Cl,H), (CN,H), (CF$_3$,H);
Z represents hydrogen;
n represents the number 0 or 1.

In a fourth aspect of the very particularly preferred embodiment of the present invention, the compounds according to the invention have a structure of the general formula (I) in which
A and B together with the carbon atoms to which they are attached represent the radical

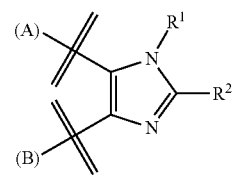

I-9 in which $R^1$ and $R^2$ have the meanings above, in particular hydrogen, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative fourth aspect of the very particularly preferred embodiment of the present invention, the compounds according to the invention have a structure of the general formula (I) in which
A and B together with the carbon atoms to which they are attached represent the radical

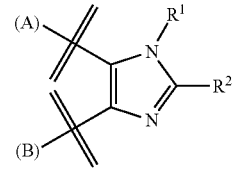

I-9 in which R¹ has the meaning above, in particular hydrogen, methyl, ethyl, isopropyl, tert-butyl, cyclopropyl, cyclopropylmethyl, trifluoromethyl or (2,2,2)-trifluoroethyl;

R² has the meaning above, in particular hydrogen, methyl, ethyl, isopropyl, tert-butyl, cyclopropyl, cyclopropylmethyl, trifluoromethyl or (2,2,2)-trifluoroethyl;

Q represents C—V or nitrogen; where
 V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
 where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF₃,F), (CF₃,H), (CN,F), (CN, H);
Z represents hydrogen;
n represents the number 0 or 1.

In the context of these aspects, it is most preferred if
A and B together with the carbon atoms to which they are attached represent the radical (I-9);
R¹ represents methyl or ethyl;
R² represents hydrogen;
Q represents C—V; where
 V represents hydrogen or methyl;
W represents fluorine;
X represents fluorine or methyl;
Y represents chlorine or methyl;
 where X and Y represent in particular the following combinations (Y,X): (Me,F), (Me,Me), (Cl,F);
Z represents hydrogen;
n represents the number 0 or 1.

In a fifth aspect of the very particularly preferred embodiment of the present invention, the compounds according to the invention have a structure of the general formula (I) in which
A and B together with the carbon atoms to which they are attached represent the radical

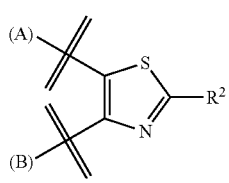

I-12 in which R² has the meaning above, in particular hydrogen, methyl, ethyl, cyclopropyl or (2,2,2)-trifluoroethyl;
Q represents C—V or nitrogen; where
 V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative fifth aspect of the very particularly preferred embodiment of the present invention, the compounds according to the invention have a structure of the general formula (I) in which A and B together with the carbon atoms to which they are attached represent the radical

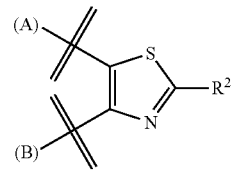

I-12 in which R² has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
 V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
 where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF₃,F), (CF₃,H), (CN,F), (CN, H);
Z represents hydrogen;
n represents the number 0 or 1.

In the context of these aspects, it is most preferred if
A and B together with the carbon atoms to which they are attached represent the radical (I-12);
R² represents hydrogen or methyl;
Q represents C—V; where
 V represents hydrogen, methyl or trifluoromethyl;
W represents fluorine;
X represents fluorine, chlorine or methyl;
Y represents chlorine or methyl;
 where X and Y represent in particular the following combinations (Y,X): (Me,F), (Me,Me), (Cl,Cl);
Z represents hydrogen;
n represents the number 0 or 1.

In a sixth aspect of the very particularly preferred embodiment of the present invention, the compounds according to the invention have a structure of the general formula (I) in which
A and B together with the carbon atoms to which they are attached represent the radical

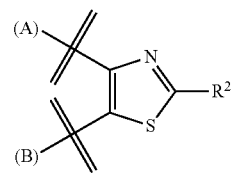

I-13 in which R² has the meaning above, in particular hydrogen, methyl, ethyl, cyclopropyl or (2,2,2)-trifluoroethyl;
Q represents C—V or nitrogen; where
 V represents hydrogen, methyl, ethyl, trifluoromethyl;
W represents fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

In an alternative sixth aspect of the very particularly preferred embodiment of the present invention, the compounds according to the invention have a structure of the general formula (I) in which A and B together with the carbon atoms to which they are attached represent the radical

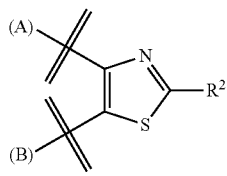
I-13 in which $R^2$ has the meaning above, in particular hydrogen, methyl, ethyl, isopropyl, tert-butyl, cyclopropyl, cyclopropylmethyl, trifluoromethyl or (2,2,2)-trifluoroethyl;

Q represents C—V or nitrogen; where
V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);

Z represents hydrogen;

n represents the number 0 or 1.

In the context of these aspects, it is most preferred if

A and B together with the carbon atoms to which they are attached represent the radical (I-13);

$R^2$ represents hydrogen or methyl;

Q represents C—V; where
V represents hydrogen or methyl;

W represents fluorine;

X represents fluorine, chlorine or methyl;

Y represents chlorine or methyl;

where X and Y represent in particular the following combinations (Y,X): (Me,F), (Me,Me), (Cl,Cl);

Z represents hydrogen;

n represents the number 0 or 1.

In a seventh aspect of the very particularly preferred embodiment of the present invention, the compounds according to the invention have a structure of the general formula (I) in which A and B together with the carbon atoms to which they are attached represent the radical

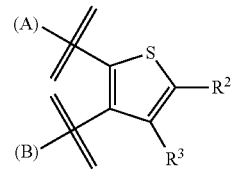
I-16 in which $R^2$ and $R^3$ have the meanings above, in particular hydrogen, methyl, ethyl, cyclopropyl or (2,2,2)-trifluoroethyl;

Q represents C—V or nitrogen; where
V represents hydrogen, methyl, ethyl, trifluoromethyl;

W represents fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

In an alternative seventh aspect of the very particularly preferred embodiment of the present invention, the compounds according to the invention have a structure of the general formula (I) in which A and B together with the carbon atoms to which they are attached represent the radical

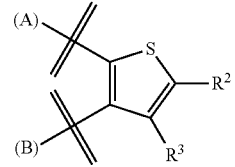
I-16 in which $R^2$ and $R^3$ have the meanings above, in particular hydrogen, methyl, ethyl, cyclopropyl, isopropyl, tert-butyl, trifluoromethyl or (2,2,2)-trifluoroethyl;

Q represents C—V or nitrogen; where
V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);

Z represents hydrogen;

n represents the number 0 or 1.

In the context of these aspects, it is most preferred if

A and B together with the carbon atoms to which they are attached represent the radical (I-16);

$R^2$ represents hydrogen;

$R^3$ represents hydrogen;

Q represents C—V; where
V represents hydrogen;

W represents fluorine;

X represents hydrogen, fluorine, chlorine or methyl;

Y represents chlorine, methyl, methoxy, trifluoromethyl or cyano;

where X and Y represent in particular the following combinations (Y,X): (Me,F), (Me,Me), (Me,H), (Cl,Cl), (Cl,H), (MeO,H), (CF$_3$,H), (CN,F), (CN,H);
Z represents hydrogen;
n represents the number 0 or 1.

In an eighth aspect of the very particularly preferred embodiment of the present invention, the compounds according to the invention have a structure of the general formula (I) in which
A and B together with the carbon atoms to which they are attached represent the radical

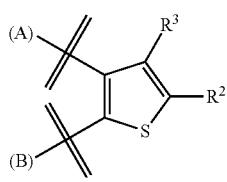

I-17 in which R$^2$ and R$^3$ have the meanings above, in particular hydrogen, fluorine, chlorine, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative eighth aspect of the very particularly preferred embodiment of the present invention, the compounds according to the invention have a structure of the general formula (I) in which
A and B together with the carbon atoms to which they are attached represent the radical

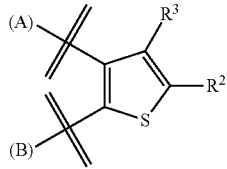

I-17 in which R$^2$ and R$^3$ have the meanings above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
V represents hydrogen, methyl, ethyl or trifluoromethyl;
W represents fluorine;
X and Y independently of one another represent hydrogen, fluorine, chlorine, bromine, methyl, ethyl, nitro;
where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF$_3$,F), (CF$_3$,H), (CN,F), (CN,H);
Z represents hydrogen;
n represents the number 0 or 1.

In the context of these aspects, it is most preferred if
A and B together with the carbon atoms to which they are attached represent the radical (I-17);
R$^2$ represents hydrogen or chlorine;
R$^3$ represents hydrogen or chlorine;
Q represents C—V; where
V represents hydrogen;
W represents fluorine;
X represents hydrogen or fluorine;
Y represents chlorine, methyl, trifluoromethyl or cyano;
where X and Y represent in particular the following combinations (Y,X): (Me,F), (Me,H), (Cl,H), (CF$_3$,H), (CN,H);
Z represents hydrogen;
n represents the number 0 or 1.

In a ninth aspect of the very particularly preferred embodiment of the present invention, the compounds according to the invention have a structure of the general formula (I) in which
A and B together with the carbon atoms to which they are attached represent the radical

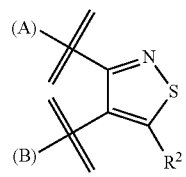

I-18 in which R$^2$ has the meaning above, in particular hydrogen, methyl, ethyl, cyclopropyl, tert-butyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

In an alternative ninth aspect of the very particularly preferred embodiment of the present invention, the compounds according to the invention have a structure of the general formula (I) in which
A and B together with the carbon atoms to which they are attached represent the radical

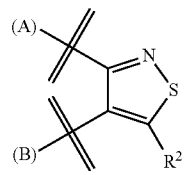

I-18 in which R$^2$ has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
V represents hydrogen, methyl, ethyl or trifluoromethyl;

W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF$_3$,F), (CF$_3$,H), (CN,F), (CN,H);
Z represents hydrogen;
n represents the number 0 or 1.

In the context of these aspects, it is most preferred if
A and B together with the carbon atoms to which they are attached represent the radical (I-18);
R$^2$ represents tert-butyl;
Q represents C—V; where
V represents hydrogen;
W represents fluorine;
X represents hydrogen or fluorine;
Y represents chlorine or methyl;
where X and Y represent in particular the following combinations (Y,X): (Me,F), (Me,H), (Cl,H);
Z represents hydrogen;
n represents the number 0 or 1.

In a tenth aspect of the very particularly preferred embodiment of the present invention, the compounds according to the invention have a structure of the general formula (I) in which
A and B together with the carbon atoms to which they are attached represent the radical

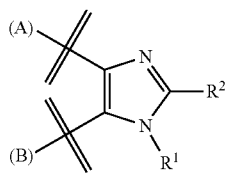

I-8 in which R$^1$ has the meaning above, in particular hydrogen, methyl, ethyl, isopropyl, tert-butyl, cyclopropyl, cyclopropylmethyl, trifluoromethyl or (2,2,2)-trifluoroethyl;
R$^2$ has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF$_3$,F), (CF$_3$,H), (CN,F), (CN,H);
Z represents hydrogen;
n represents the number 0 or 1.

In the context of this aspect, it is most preferred if
A and B together with the carbon atoms to which they are attached represent the radical (I-8);
R$^1$ represents methyl;
R$^2$ represents hydrogen;
Q represents C—V; where
V represents hydrogen;
W represents fluorine;
X represents fluorine;
Y represents methyl;
Z represents hydrogen;
n represents the number 0 or 1.

In an eleventh aspect of the very particularly preferred embodiment of the present invention, the compounds according to the invention have a structure of the general formula (I) in which
A and B together with the carbon atoms to which they are attached represent the radical

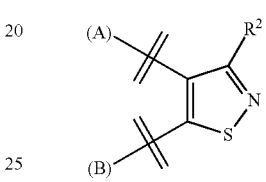

I-11 in which R$^2$ has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF$_3$,F), (CF$_3$,H), (CN,F), (CN,H);
Z represents hydrogen;
n represents the number 0 or 1.

In the context of this aspect, it is most preferred if
A and B together with the carbon atoms to which they are attached represent the radical (I-11);
R$^2$ represents methyl;
Q represents C—V or nitrogen; where
V represents hydrogen;
W represents fluorine;
X represents fluorine;
Y represents methyl;
Z represents hydrogen;
n represents the number 0 or 1.

In a twelfth aspect of the very particularly preferred embodiment of the present invention, the compounds according to the invention have a structure of the general formula (I) in which
A and B together with the carbon atoms to which they are attached represent the radical

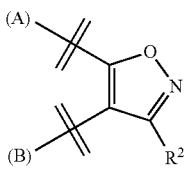

I-20 in which R² has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF₃,F), (CF₃,H), (CN,F), (CN,H);
Z represents hydrogen;
n represents the number 0 or 1.
In the context of this aspect, it is most preferred if
A and B together with the carbon atoms to which they are attached represent the radical (I-20);
R² represents methyl, ethyl, isopropyl or trifluoromethyl;
Q represents C—V; where
  V represents hydrogen;
W represents fluorine;
X represents fluorine;
Y represents methyl;
Z represents hydrogen;
n represents the number 0 or 1.

In a thirteenth aspect of the very particularly preferred embodiment of the present invention, the compounds according to the invention have a structure of the general formula (I) in which
A and B together with the carbon atoms to which they are attached represent the radical

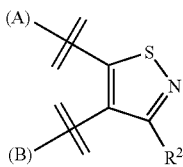

I-21 in which R² has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF₃,F), (CF₃,H), (CN,F), (CN,H);
Z represents hydrogen;
n represents the number 0 or 1.
In the context of this aspect, it is most preferred if
A and B together with the carbon atoms to which they are attached represent the radical (I-21);
R² represents methyl, ethyl or tert-butyl;
Q represents C—V or nitrogen; where
  V represents hydrogen or methyl;
W represents fluorine;
X represents fluorine;
Y represents methyl;
Z represents hydrogen;
n represents the number 0 or 1.

In a fourteenth aspect of the very particularly preferred embodiment of the present invention, the compounds according to the invention have a structure of the general formula (I) in which
A and B together with the carbon atoms to which they are attached represent the radical

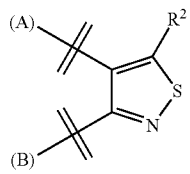

I-22 in which R² has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), (CF₃,F), (CF₃,H), (CN,F), (CN,H);
Z represents hydrogen;
n represents the number 0 or 1.
In the context of this aspect, it is most preferred if
A and B together with the carbon atoms to which they are attached represent the radical (I-22);
R² represents hydrogen;
Q represents C—V; where
  V represents hydrogen;
W represents fluorine;
X represents fluorine;
Y represents methyl;
Z represents hydrogen;
n represents the number 0 or 1.

In a fifteenth aspect of the very particularly preferred embodiment of the present invention, the compounds according to the invention have a structure of the general formula (I) in which A and B together with the carbon atoms to which they are attached represent the radical

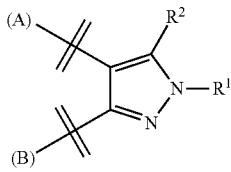
I-24 in which $R^1$ has the meaning above, in particular hydrogen, methyl, ethyl, isopropyl, tert-butyl, cyclopropyl, cyclopropylmethyl, trifluoromethyl or (2,2,2)-trifluoroethyl;
$R^2$ has the meaning above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.
  In the context of this aspect, it is most preferred if
A and B together with the carbon atoms to which they are attached represent the radical (I-24);
$R^1$ represents methyl;
$R^2$ represents hydrogen or methyl;
Q represents C—V; where
  V represents hydrogen;
W represents fluorine;
X represents fluorine;
Y represents methyl;
Z represents hydrogen;
n represents the number 0 or 1.
  In a sixteenth aspect of the very particularly preferred embodiment of the present invention, the compounds according to the invention have a structure of the general formula (I) in which
A and B together with the carbon atoms to which they are attached represent the radical

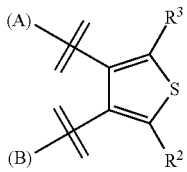
I-25 in which $R^2$ and $R^3$ have the meanings above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.
  In the context of this aspect, it is most preferred if
A and B together with the carbon atoms to which they are attached represent the radical (I-25);
$R^2$ represents hydrogen or methyl;
$R^3$ represents hydrogen or methyl;
Q represents C—V; where
  V represents hydrogen;
W represents fluorine;
X represents fluorine;
Y represents methyl;
Z represents hydrogen;
n represents the number 0 or 1.
  In a seventeenth aspect of the very particularly preferred embodiment of the present invention, the compounds according to the invention have a structure of the general formula (I) in which
A and B together with the carbon atoms to which they are attached represent the radical

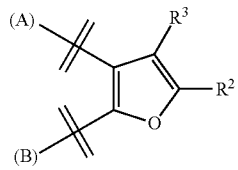
I-26 in which $R^2$ and $R^3$ have the meanings above, in particular hydrogen, methyl, ethyl, isopropyl, tert-butyl, cyclopropyl, cyclopropylmethyl, trifluoromethyl or (2,2,2)-trifluoroethyl;
Q represents C—V or nitrogen; where
  V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
  where X and Y represent in particular the following combinations (Y,X): (Me,F), (Me,Cl), (Me,Me), (Me,H), (Et,Et), (Cl,Fl), (Cl,Cl), (Cl,H), (MeO,F), (MeO,H), (Br, F), (Br,Cl), (Br,H), (F,F), (CF$_3$,F), (CF$_3$,H), (CN,F), (CN, H);
Z represents hydrogen;
n represents the number 0 or 1.
  In the context of this aspect, it is most preferred if
A and B together with the carbon atoms to which they are attached represent the radical (I-26);
$R^2$ represents methyl;
$R^3$ represents hydrogen;
Q represents C—V; where
  V represents hydrogen;
W represents fluorine;
X represents fluorine;
Y represents methyl;
Z represents hydrogen;
n represents the number 0 or 1.
  The present compounds of the general formula (I) where n=1 contain a chiral sulphur atom. According to the rules of Cahn, Ingold and Prelog (CIP rules), the substituents at this sulphur may have either an (R)- or an (S)-configuration. The present invention encompasses both the pure (R) and (S) enantiomers and mixtures in any ratio (including the racemates).

The abovementioned general or preferred radical definitions or illustrations can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred.

Particular preference is given in accordance with the invention to the compounds of the formula (I) which contain a combination of the meanings listed above as particularly preferred.

Very particular preference is given in accordance with the invention to the compounds of the formula (I) which contain a combination of the meanings listed above as very particularly preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In the context of the present invention, halogen represents fluorine, chlorine, bromine and iodine, particularly preferably fluorine, chlorine and bromine and very particularly preferably fluorine and chlorine.

Furthermore, alkyl represents straight-chain or branched $C_1$- to $C_8$-alkyl, preferably straight-chain or branched $C_1$- to $C_6$-alkyl, more preferably straight-chain or branched $C_1$- to $C_4$-alkyl, in particular methyl and ethyl.

Alkoxy represents straight-chain or branched $C_1$- to $C_8$-alkoxy, preferably straight-chain or branched $C_1$- to $C_6$-alkoxy, more preferably straight-chain or branched $C_1$- to $C_4$-alkoxy, in particular methoxy.

Haloalkyl and haloalkoxy result from substituted alkyl and alkoxy radicals according to the above definition.

Alkyl radicals in cycloalkyl, alkoxycarbonyl, alkylthioalkyl, alkylsulphinylalkyl, phenylalkyl, hetarylalkyl and alkylsulphonylalkyl likewise result from the above definition of alkyl.

Preparation Processes

The compounds of the general formula (I) can be classified into compounds where n=0 (Ia) and n=1 (Ib) and can be prepared according to the scheme below, for example according to Processes A and B, like those described in the application WO 2010/100189. In deviation from these methods, the compounds of the formula (I) can also be prepared according to Processes C, D and E.

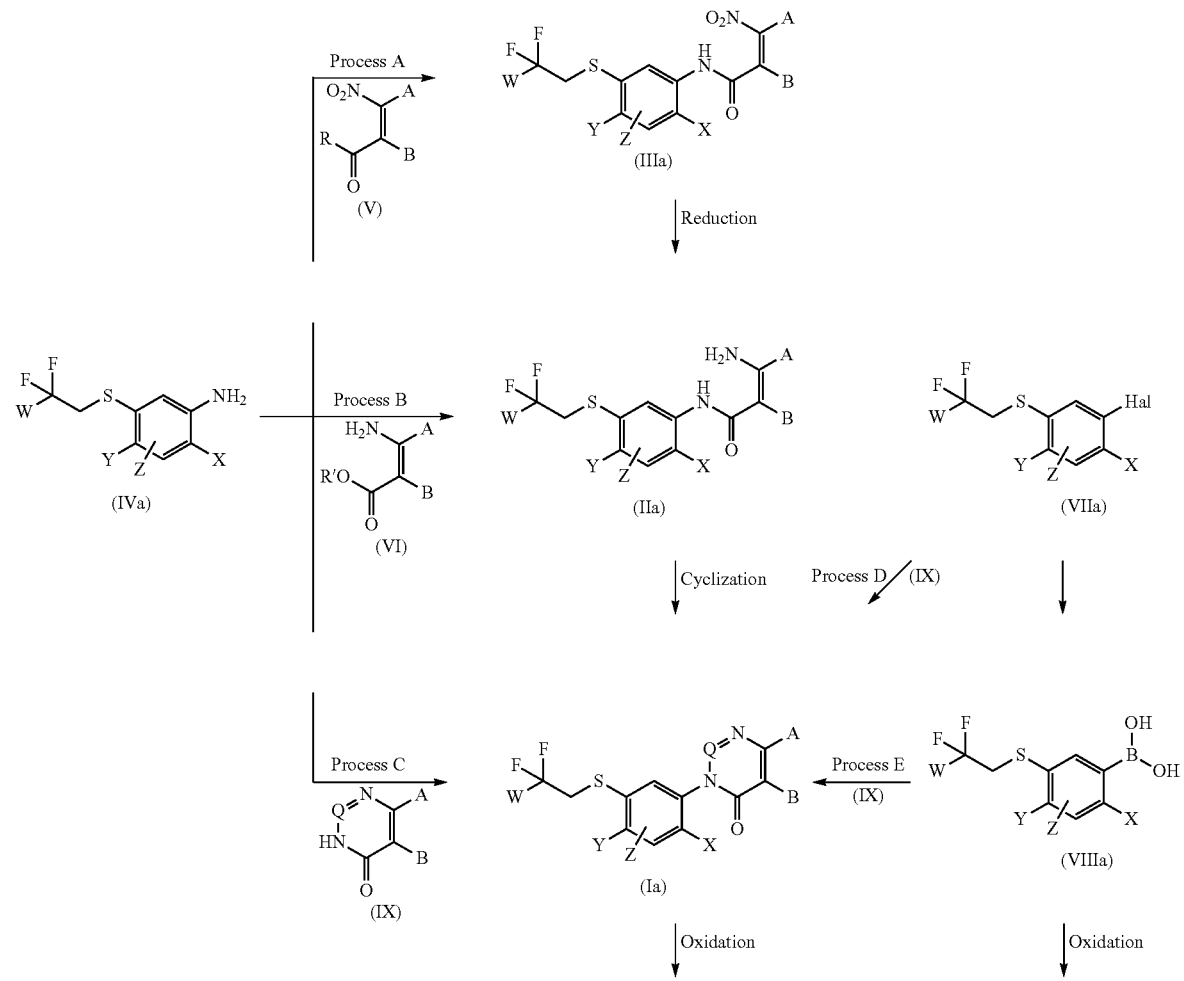

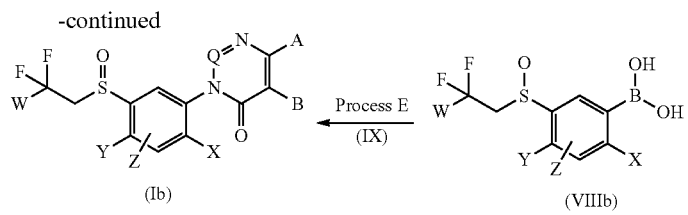

Process A

Compounds of the formula (IIIa) or tautomers thereof can be prepared, for example, according to Process A by reacting anilines of the formula (IVa) with nitro compounds of the formula (V) in which R represents hydroxy or halogen (preferably Cl and Br).

Many different methods for preparing carboxamides from carboxylic acids (R=hydroxy) or carbonyl halides (R=halogen) are known, for example G. Benz in Comprehensive Organic Synthesis, 1$^{st}$ Ed., Pergamon Press, Oxford, 1991, Vol. 6, pp. 381-417; P. D. Bailey et al. in Comprehensive Organic Functional Group Transformation, 1$^{st}$ Ed., Elsevier Science Ltd., Oxford, 1995, Vol. 5, pp. 257-308 and R. C. Larock in Comprehensive Organic Transformations, 2nd Ed., Wiley-VCH, New York, Weinheim, 1999, pp. 1929-1994. Carbonyl chlorides can be isolated or used as generated in situ.

The amidation reactions are optionally carried out in the presence of a condensing agent, optionally in the presence of an acid activator, optionally in the presence of an acid acceptor and optionally in the presence of a solvent. Suitable condensing agents are all condensing agents which can customarily be used for such amidation reactions. Examples which may be mentioned are acid halide formers such as phosgene, phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino) phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU) and 1-hydroxybenzotriazole. These reagents can be employed separately or, if appropriate, in combination. Suitable acid acceptors are all customary inorganic or organic bases, for example triethylamine, diisopropylethylamine, N-methylmorpholine or N,N-dimethylaminopyridine. Process A according to the invention is optionally carried out in the presence of a suitable reaction auxiliary such as, for example, N,N-dimethylformamide or N,N-dimethylaminopyridine.

Furthermore, it is also possible to use mixed anhydrides for preparing (III), as published, for example, in J. Am. Chem. Soc 1967, 5012. In this process, it is possible to use various chloroformic esters, for example isobutyl chloroformate, isopropyl chloroformate. It is likewise possible for this purpose to use diethylacetyl chloride, trimethylacetyl chloride and the like.

Compounds of the general formula (IIa) or tautomers thereof can be prepared, for example, by reduction of the nitro compounds of the general formula (IIIa) according to methods known from the literature. Suitable processes for such reductions are in particular metal-mediated reactions such as, for example, tin(II) chloride, iron powder, zinc powder, Raney nickel, palladium(0) on carbon or platinum dioxide (as hydrate). The metal-mediated reductions, for example with tin(II) chloride, can be carried out according to a process described in Organic Syntheses Coll. Vol. (III), 453.

Process B

Alternatively, compounds of the general formula (IIa) can be prepared by an acylation reaction according to Process B where an aniline of the general formula (IVa) is reacted with a suitable carboxylic acid derivative of the formula (VI), where R' preferably represents alkyl. This can take place without activation, as described by B. M. Trost and I. Fleming in Comprehensive Organic Synthesis, Ed. Pergamon, 1991, Vol. 6. Alternatively, the literature discloses activation methods by formation of an aluminium amide, as by T. Ooi and K. Marouka in Science of Synthesis, Ed. Georg Thieme, 2003, Vol. 7, 225-246. The aluminium amides can be obtained from the anilines or their salts by reaction with trimethylaluminium or their air-stable adduct with 1,4-diazobicyclo[2.2.3]octane (DABCO), as described by S. Woodward in Tet. Lett. 2006, 47, 5767-5769.

R' may also represent hydrogen, so that all synthesis methods described in Process A would also be suitable for the synthesis of compounds of the formula (IIa).

Various methods are suitable for the preparation of thioethers of the general formula (Ia). Examples which may be mentioned are: starting with compounds of the formula (IIa) by ring closure; starting with anilines of the formula (IVa) by reaction with bicyclic compounds of the formula (IX) according to Process C or starting with halides of the formula (VIIa) or boronic acids of the formula (VIIIa) or (VIIIb) by metal-catalysed reactions according to Process D or Process E.

Cyclization

For Q=C—V, where V represents H or alkyl, the preparation of the thioether of the general formula (Ia) can take place according to methods known from the literature by cyclization of open-chain precursors of the formula (IIa) with an orthoester such as triethyl orthoformate or triethyl orthoacetate, optionally in the presence of a solvent or diluent, optionally in the presence of an acid of organic nature (such as para-toluenesulphonic acid) or inorganic nature (such as hydrochloric acid or sulphuric acid) in catalytic or stoichiometric amounts or in excess or instead of the solvent or diluent.

Alternatively, the thioether of the general formula (Ia) can be prepared by methods known from the literature by reaction with N,N-dimethylformamide dimethyl acetal and subsequent reaction with formic acid.

For Q=C—V, where V represents alkyl or haloalkyl, the preparation of the thioether of the general formula (Ia) can also be carried out by reaction with the appropriate carboxylic anhydrides according to methods known from the literature, for example as described for V=CF3 in the patent WO 2008/039489.

For Q=N, the compounds of the formula (Ia) can be prepared by diazotization of the compounds of the formula (IIa) according to methods known from the literature. For example, a nitrite source such as sodium nitrite or isobutyl nitrite is added to compounds of the formula (IIa), typically in water, alcohol or a polar inert solvent, at from 0 to 5° C. in the presence of an organic or inorganic acid. Exemplary reaction conditions can be found, for example, in the patent WO 2004/242572 or in J. Amer. Chem. Soc. Perkin Trans. 1, 1980, 633-638.

Process C

Alternatively, the compounds of the formula (Ia) can be prepared from anilines of the formula (IVa) by reaction with bicyclic compounds of the formula (IX) or their tautomeric hydroxypyrimidinones according to Process C. As described by Yang et al. in Org. Lett. 2009, 11, 6, 1421-1424, the N-arylation of the hydroxypyrimidinones is carried out under mild reaction conditions, for example by HATU-mediated coupling with primary amines using DBU as base in acetonitrile as solvent, in most cases at room temperature or at up to 70° C.

Process D

An alternative preparation of the compounds of the formula (Ia) is provided by the reaction of halides of the formula (VIIa) with bicyclic compounds of the formula (IX) under metal-catalysed reaction conditions. The literature discloses numerous methods, for example in Chem. Pharm. Bull. 1997, 45, 4, 719-721; in Tet. Lett. 2006, 47, 7677-7680; or Synlett 2008, 9, 1335-1340, where the metal source used is copper iodide in the presence of a base and optionally a ligand at elevated temperatures (for example from 120 to 150° C.).

Process E

It has likewise been found that the reaction of boronic acids of the formula (VIIIa), which can be prepared from halides (VIIa) according to methods known from the literature, with bicyclic compounds of the formula (IX) by metal-catalysed reactions may serve to prepare the compounds of the formula (Ia). An overview of such reactions can be found in Synthesis 2011, 6, 829-856. A suitable metal source is copper(II) acetate, as in Synlett 2010, 5, 721-724; Tetrahedron 2006, 62, 8, 1764-1771; Tetrahedron Lett. 2005, 46, 34, 5699-5702 or WO 2010/104818.

The oxidation of the boronic acids of the formula (VIIIa) or their boronic esters according to methods known from the literature, for example with sodium periodate, leads to sulphoxides of the formula (VIIIb) which can likewise be reacted with bicyclic compounds of the formula (IX) under metal-catalysed reaction conditions, resulting in the target compounds (Ib).

When carrying out the Processes D and E according to the invention, any commercial microwave apparatus suitable for these reactions may optionally be employed (for example Anton Paar Monowave 300, CEM Discover S, Biotage Initiator 60).

Compounds of the general formula (Ib) can be prepared by oxidation according to processes known from the literature from compounds of the general formula (Ia), for example using an oxidizing agent in a suitable solvent and diluent. Suitable oxidizing agents are, for example, dilute nitric acid, hydrogen peroxide and peroxycarboxylic acids such as, for example, meta-chloroperbenzoic acid. Suitable solvents are inert organic solvents, typically acetonitrile and halogenated solvents such as dichloromethane, chloroform or dichloroethane.

A large number of different methods are suitable for generating enantiomerically enriched sulphoxides, as described by A. R. Maguire in ARKIVOC, 2011(i), 1-110: metal-catalysed asymmetric oxidations of thioethers, for example with titanium and vanadium as the most frequently employed catalyst sources, in the form of Ti(O$^i$Pr$_4$) and VO(acac)$_2$, together with a chiral ligand and an oxidizing agent such as tert-butyl hydroperoxide (TBHP), 2-phenyl-propan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulphoxides and nucleophilic shift (according to Andersen's method).

The enantiomers can also be obtained from the racemate, for example by separating them on a preparative scale by chiral HPLC.

Alternatively, compounds of the general formula (Ib) may be prepared by methods similar to those mentioned here carried out in a different order, for example by oxidation of the anilines of the formula (IVa) to give sulphoxides of the formula (IVb) and their further conversion according to Process A, B or C.

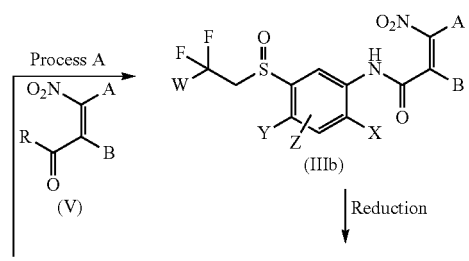

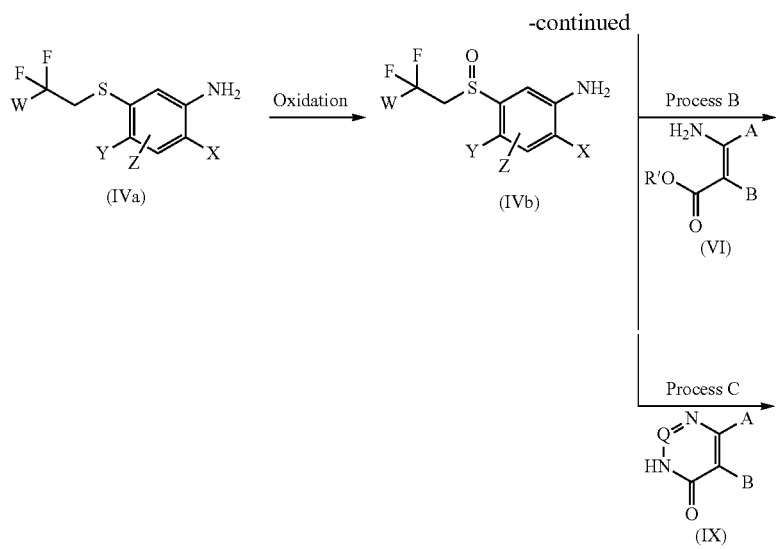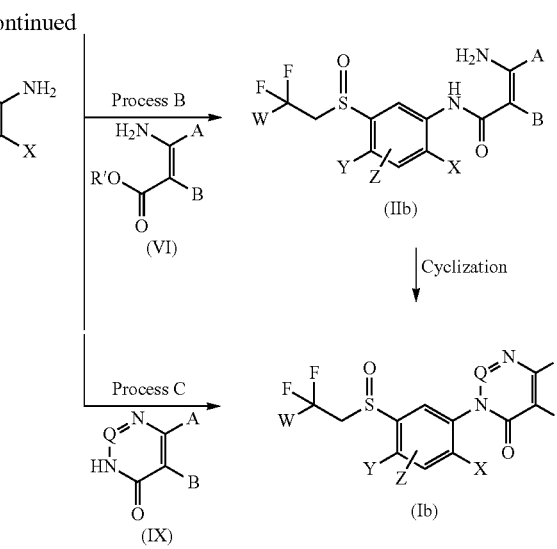

Illustration of the Starting Materials and Intermediates

The anilines of the general formula (IV) can be classified into compounds where n=0 (IVa) and n=1 (IVb).

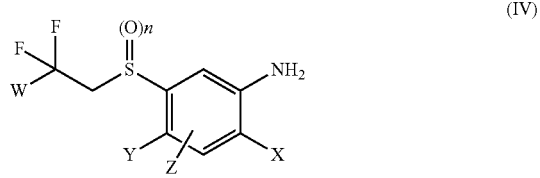

Some of the anilines of the formula (IVa) are known from the literature, for example from JP 2007/284356, or they can be synthesized by processes known from the literature.

The compounds of the formula (IVb) are novel and can be prepared by oxidation, in particular under the conditions mentioned in the Preparation Examples.

The anilines of the general formula (IVa) can be prepared, for example, as in the scheme below;

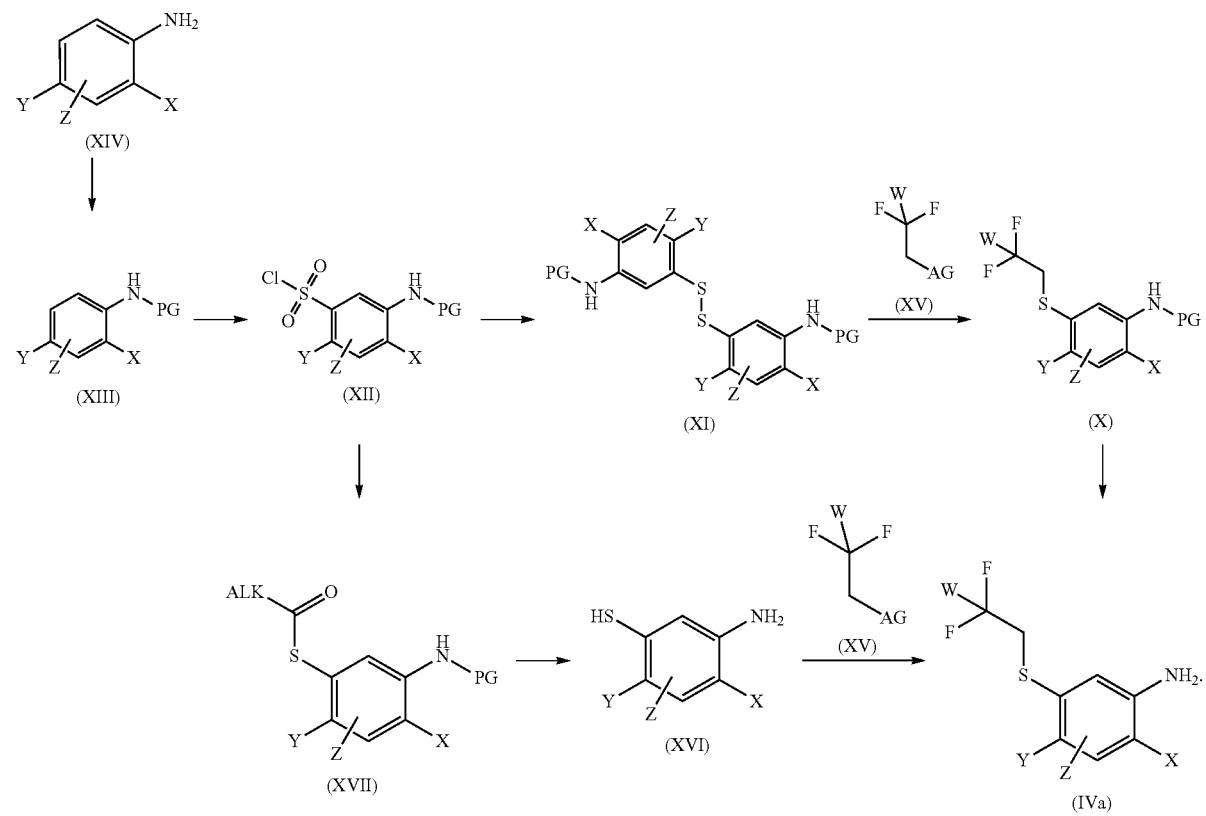

where X, Y, Z and W have the meanings given above, AG represents a leaving group and PG represents a protective group.

Anilines of the formula (XIV) are either commercially available or they can be prepared by known methods. They can be protected with a suitable protective group such as, for example, an acetyl group, to give compounds of the formula (XIII). In the presence of acids, acid anhydrides or acid chlorides, for example, the anilines (XIV) can be converted into the corresponding anilides (XIII). Chlorosulphonation of the protected anilines (XIII) with chlorosulphonic acid affords the corresponding sulphonyl chlorides (XII). Reduction of the sulphonyl chlorides (XII) to the disulphides (XI) can be carried out using methods known from the literature such as iron in hydrochloric acid or iodide. Reaction of the disulphides (XI) with haloalkyl electrophiles of the formula (XV) where AG represents a leaving group such as, for example, chlorine, bromine, tosylate, mesylate or triflate affords the sulphides (X). The protective group can be removed by suitable methods known from the literature, giving anilines of the formula (IVa).

Instead of the reduction to the disulphide (XI), the sulphonyl chloride (XII) can be reduced with a suitable reducing agent such as, for example, iodine/phosphorus to give the alkyl thioate (XVII), which is then deprotected using a suitable method, for example the reaction with potassium hydroxide solution, to afford thiols of the formula (XVI). Reaction of the thiols (XVI) with haloalkyl electrophiles of the formula (XV) where AG represents a leaving group such as, for example, chlorine, bromine, tosylate, mesylate or triflate affords the sulphides (IVa).

The compounds of the formulae (X), (XI), (XII), (XIII), (XVI) and (XVII) are novel and can be prepared in particular under the conditions mentioned in the Preparation Examples.

Alternatively, the thioethers of the formula (IVa) can be prepared according to the following scheme

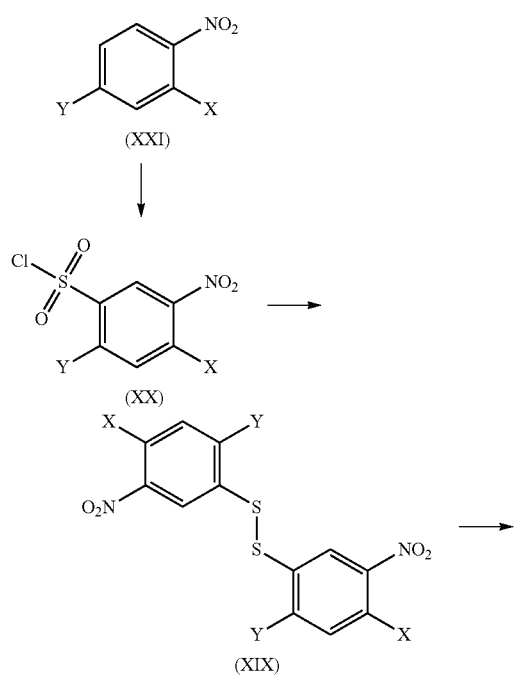

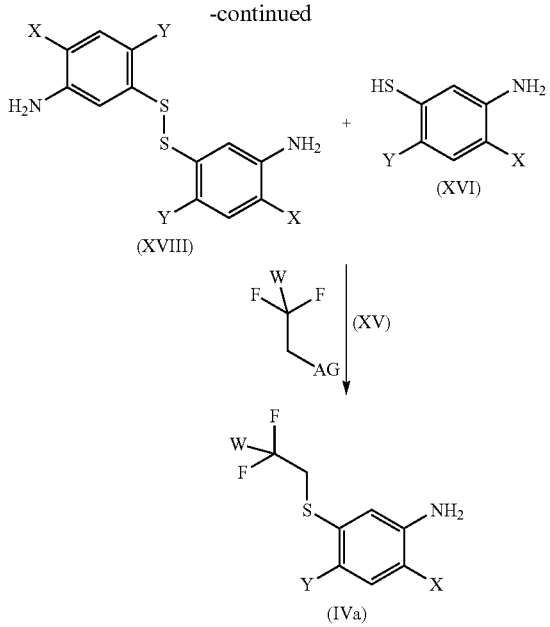

X, Y independently of one another may particularly preferably represent hydrogen, fluorine, chlorine, bromine.

Chlorosulphonation of the nitroaromatics of the formula (XXI) with chlorosulphonic acid affords the corresponding sulphonyl chlorides (XX). Reduction of the sulphonyl chlorides (XX) to the bis(nitroaryl) disulphides (XIX) can be carried out using methods known from the literature, for example iodide. Reduction of the disulphides (XXI) to the disulphanediyldianilines (XIX), some of which are formed as a mixture with the corresponding aminoarylthiols (XVI), is possible using generally known reducing agents such as, for example, hydrogen, if appropriate with the aid of heterogeneous catalysts such as, for example, Raney nickel, platinum on activated carbon or palladium on activated carbon. Reaction of the disulphides (XVIII) or thiophenols (XVI) with haloalkyl electrophiles of the formula (XV) where AG represents a leaving group such as, for example, chlorine, bromine, iodine, tosylate, mesylate or triflate affords the 3-[(2,2,2-trifluoroethyl)sulphanyl]anilines of the formula (IVa).

The compounds of the formulae (XVI), (XVIII), (XIX) and (XX) are novel and can be prepared in particular under the conditions mentioned in the Preparation Examples.

Nitro compounds of the formula (V)

in which A and B have the above meaning and R represents hydroxy or halogen are commercially available or known from the literature, or they can be synthesized by processes known from the literature. Examples which may be mentioned are:

1-methyl-5-nitro-1H-imidazole-4-carboxylic acid (commercially available),
1-ethyl-5-nitro-1H-imidazole-4-carboxylic acid (V-1) (see synthesis examples).

Carboxylic acid derivatives of the formula (VI)

in which A and B have the above meaning and R' represents hydrogen or alkyl. These are commercially available or known from the literature, or they can be synthesized by processes known from the literature.

Examples which may be mentioned are the carboxylates below (R'=alkyl):
ethyl 5-amino-1-(2,2,2-trifluoroethyl)-1H-pyrazole-4-carboxylate (commercially available),
ethyl 4-amino-1-methyl-1H-pyrazole-5-carboxylate (commercially available),
ethyl 5-amino-1,3-thiazole-4-carboxylate (commercially available),
ethyl 5-amino-2-methyl-1,3-thiazole-4-carboxylate (commercially available),
methyl 4-amino-1,3-thiazole-5-carboxylate (commercially available),
methyl 2-aminothiophene-3-carboxylate (commercially available),
ethyl 3-aminothiophene-2-carboxylate (commercially available).

Halides of the general formula (VIIa)

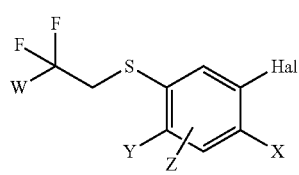

in which X, Y, Z and W have the meanings given above and Hal represents chlorine, bromine or iodine are known from the literature or can be synthesized by processes known from the literature.

Examples which may be mentioned are the bromides below:
5-bromo-4-fluoro-2-methylphenyl-2,2,2-trifluoroethyl sulphide (VIIa-1) (WO 2007/034755, JP 2007/284385 and JP 2009/023910),
5-bromo-2-methylphenyl-2,2,2-trifluoroethyl sulphide (VIIa-7) (JP 2008/308448 and JP 2008/260706, see synthesis examples),
4-bromo-1-methoxy-2-[(2,2,2-trifluoroethyl)sulphanyl]benzene (VIIa-8) (see synthesis examples),
4-bromo-1-chloro-2-[(2,2,2-trifluoroethyl)sulphanyl]benzene (VIIa-3) (see synthesis examples),
1-bromo-2,4-dichloro-5-[(2,2,2-trifluoroethyl)sulphanyl] benzene (VIIa-6) (see synthesis examples),
1-bromo-2,4-dimethyl-5-[(2,2,2-trifluoroethyl)sulphanyl] benzene (VIIa-11) (see synthesis examples),
4-bromo-2-[(2,2,2-trifluoroethyl)sulphanyl]benzonitrile (VIIa-9) (see synthesis examples),
4-bromo-2-[(2,2,2-trifluoroethyl)sulphanyl]-1-(trifluoromethyl)benzene (VIIa-10) (see synthesis examples).

Suitable starting materials for the synthesis of the iodides of the general formula (VIIa) are bromides having the same formula, for example in halogen exchange reactions according to methods known from the literature, if appropriate with metal catalysis (see H. Suzuki, Chem. Let. 1985, 3, 411-412; S. L. Buchwald, J. Amer. Chem. Soc. 2002, 124 (50), 14844-14845). Synthesis is also possible from anilines of the formula (IVa) under Sandmeyer reaction conditions as described by E. B. Merkushev in Synthesis 1988, 12, 923-937. Examples which may be mentioned are the iodides below:
4-fluoro-5-iodo-2-methylphenyl-2,2,2-trifluoroethyl sulphide (VIIa-1-I) (see synthesis examples),
4-iodo-1-methyl-2-[(2,2,2-trifluoroethyl)sulphanyl]benzene (VIIa-7-I) (see synthesis examples).

Boronic acids of the general formula (VIIIa)

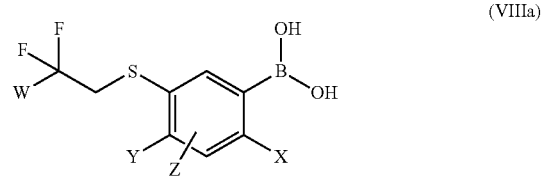

in which X, Y, Z and W have the meanings given above are known from the literature or can be synthesized by processes known from the literature.

Examples which may be mentioned are the boronic acids below:
{2-fluoro-4-methyl-5-[(2,2,2-trifluoroethyl)sulphanyl] phenyl}boronic acid (VIIIa-1) (WO 2007/034755, JP 2007/284385 and JP 2009/023910, see synthesis examples),
{4-methyl-3-[(2,2,2-trifluoroethyl)sulphanyl] phenyl}boronic acid (VIIIa-7) (see synthesis examples).

Boronic acids of the general formula (VIIIb)

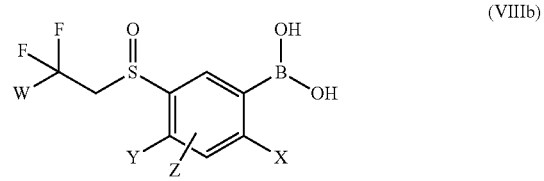

in which X, Y, Z and W have the meanings given above are known from the literature or can be synthesized by processes known from the literature.

Examples which may be mentioned are the boronic acids below:
{2-fluoro-4-methyl-5-[(2,2,2-trifluoroethyl)sulphinyl] phenyl}boronic acid (VIIIb-1) (see synthesis examples),
{4-methyl-3-[(2,2,2-trifluoroethyl)sulphinyl] phenyl}boronic acid (VIIIb-7) (see synthesis examples).

Bicyclic heterocycles of the general formula (IX)

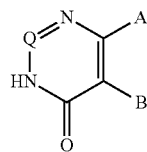

(IX)

in which A and B have the meanings given above are known from the literature or can be synthesized by processes known from the literature.

Examples which may be mentioned are the bicyclic heterocycles below:
1-methyl-1,5-dihydro-4H-pyrazolo[3,4-d]pyrimidin-4-one (commercially available),
1,3-dimethyl-1,5-dihydro-4H-pyrazolo[3,4-d]pyrimidin-4-one (commercially available),
1-methyl-1,6-dihydro-7H-pyrazolo[4,3-d]pyrimidin-7-one (commercially available),
9-methyl-1,9-dihydro-6H-purin-6-one (commercially available),
thieno[2,3-d]pyrimidin-4(3H)-one (commercially available),
thieno[3,2-d]pyrimidin-4(3H)-one (commercially available).

Use

The active compounds according to the invention, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active compounds.

The present invention further relates to formulations and use forms prepared therefrom as crop protection compositions and/or pesticides, for example drench, drip and spray liquors, comprising at least one of the active compounds according to the invention. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soya bean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the active compounds with auxiliaries such as, for example, extenders, solvents and/or solid carriers and/or other auxiliaries such as, for example, surfactants. The formulations are prepared either in suitable facilities or else before or during application.

Auxiliaries used may be substances capable of giving the formulation of the active compound, or the use forms prepared from these formulations (such as ready-to-use crop protection compositions, for example, such as spray liquors or seed dressings), particular properties, such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

It is possible for colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc, to be present as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Penetrants contemplated in the present context include all those substances which are commonly used to promote the penetration of agrochemically active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya bean oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form. The compounds are employed in a customary manner appropriate for the use forms.

The active compounds according to the invention may be used as such or in formulations thereof, including in a mixture with one or more suitable fungicides, bactericides, acaricides, nematicides, insecticides, microbicides, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products. In general, combination of the inventive active compounds and mixing partners results in synergistic effects, which means that the efficacy of the mixture in question is greater than the efficacy of the individual components. It is generally possible to use the combinations in premixes, tank mixes or ready mixes, and also in seed applications.

Particularly favourable examples of mixing partners are the following compounds:

Insecticides/Acaricides/Nematicides

The active compounds identified here by their common names are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists such as, for example, cyclodiene organochlorines, e.g. chlordane and endosulfan; or phenylpyrazoles (fiprole), e.g. ethiprole and fipronil.

(3) Sodium channel modulators/voltage-dependent sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin; or DDT; or methoxychlor.

(4) Nicotinergic acetylcholine receptor (nAChR) agonists such as, for example, neonicotinoids, e.g. acetamiprid, clothianidin, dinotefuran, imidacloprid, nitenpyram, thiacloprid and thiamethoxam; or nicotine.

(5) Nicotinergic acetylcholine receptor (nAChR) allosteric activators such as, for example, spinosyns, e.g. spinetoram and spinosad.

(6) Chloride channel activators such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene; or fenoxycarb; or pyriproxyfen.

(8) Active compounds with unknown or nonspecific mechanisms of action such as, for example,
alkyl halides, e.g. methyl bromide and other alkyl halides; or chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or
etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron; or
organotin compounds, e.g. azocyclotin, cyhexatin and fenbutatin oxide; or
propargite; or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocyclam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Moulting disruptors, dipteran, such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone; or acequinocyl; or fluacrypyrim.

(21) Complex-I electron transport inhibitors, for example METI acaricides, e.g. fenazaquin, fenpyroximate, pyrimidifen, pyridaben, tebufenpyrad and tolfenpyrad; or rotenone (Denis).

(22) Voltage-dependent sodium channel blockers, for example indoxacarb; or metaflumizone.

(23) Inhibitors of acetyl-CoA carboxylase such as, for example,
tetronic and tetramic acid derivatives, e.g. spirodiclofen, spiromesifen and spirotetramat.

(24) Complex-IV electron transport inhibitors such as, for example,
phosphines, e.g. aluminium phosphide, calcium phosphide, phosphine and zinc phosphide; or
cyanide.

(25) Complex-II electron transport inhibitors such as, for example, cyenopyrafen.

(28) Ryanodine receptor effectors such as, for example, diamides, for example chlorantraniliprole and flubendiamide.

Further active compounds with unknown mechanism of action, such as, for example, amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM I-1582, for example VOTiVO™, BioNem), and the following known active compounds:

3-bromo-N-{2-bromo-4-chloro-6-[(1-cyclopropylethyl) carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), flupyradifurone, 4-{[(6-chloro-5-fluoropyrid-3-yl)methyl](methyl)amino}furan-2(5H)-one (known from WO2007/115643), 4-{[(5,6-dichloropyrid-3-yl)methyl](2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulphanylidene}cyanamide (known from WO2007/149134) and diastereomers thereof {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO2007/149134) and sulfoxaflor and diastereomers thereof [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene]cyanamide (A2), designated as diastereomer group A (known from WO 2010/074747, WO 2010/074751), [(R)-methyl(oxido){(1S)-1-[6-(trifluoromethyl)pyridin-3-yl]ethyl}-$\lambda^4$-sulphanylidene]cyanamide (B1) and [(S)-methyl(oxido){(1R)-1-[6-(trifluoromethyl)pyridin-3-yl]ethyl}-$\lambda^4$-sulphanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3, 5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), flometoquin, PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2 (5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl) ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925) and methyl 2-[3, 5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

Fungicides (1) Inhibitors of ergosterol biosynthesis such as, for example, (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulphate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy] phenyl}imidoformamide and (1.64) O-[1-(4-methoxyphenoxy)-3,3-dimethylbutan-2-yl]1H-imidazole-1-carbothioate (111226-71-2).

(2) Respiration inhibitors (respiratory chain inhibitors) such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-5), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR, 9RS and the anti-empimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain such as, for example, (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division such as, for example, (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity such as, for example, (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulphate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulphur and sulphur preparations such as, for example, calcium polysulphide (7704-34-9), (5.31) thiram (137-26-8), (5.32) tolylfluanid (731-27-1), (5.33) zineb (12122-67-7) and (5.34) ziram (137-30-4).

(6) Resistance inducers such as, for example, (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis such as, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors such as, for example, (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis such as, for example, (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis such as, for example, (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors such as, for example, (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis such as, for example, (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors such as, for example, (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers such as, for example, (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds such as, for example, (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-8), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulphonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulphonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine- 3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazol-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulphate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds such as, for example, (16.1) 1-methyl-3-(trifluoromethyl)-N-[T-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulphonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All mixing partners mentioned in classes (1) to (16) can, if they are capable on the basis of their functional groups, optionally form salts with suitable bases or acids.

A mixture with other known active compounds, such as herbicides, fertilizers, growth regulators, safeners, semiochemicals, or else with agents for improving the plant properties, is also possible.

When used as insecticides, the inventive active compounds may also be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

All plants and plant parts can be treated in accordance with the invention. Plants in this context are understood to include all plants and plant populations, such as desired and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seed.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The terms "parts" and "parts of plants" or "plant parts" have been elucidated above.

The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They may be cultivars, biotypes and genotypes.

Depending on type and cultivar of plant, its locus and growth conditions (soils, climate, vegetation period, nutrition), the treatment according to the invention may also be accompanied by superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are emphasized in particular are the increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulphonylureas, glyphosate or phosphinothricin (for example the "PAT" gene). The genes which impart the desired traits in question may also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants include maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated in accordance with the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds according to the invention of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals, for example hamsters, guinea pigs, rats and mice. The control of these arthropods is intended to reduce cases of death and reduced productivity (of meat, milk, wool, hides, eggs, honey, etc.), and so more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

At the same time, the inventive compounds can be used for protection of objects which come into contact with saltwater or brackish water, especially hulls, screens, nets, buildings, moorings and signalling systems, against fouling.

In addition, the compounds according to the invention can be used as antifouling compositions, alone or in combinations with other active compounds.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium,* Opiliones *phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

Further, Likewise Preferred Embodiments A1 to A17 of the Invention are Mentioned Below A1. Compounds of the general formula (I)

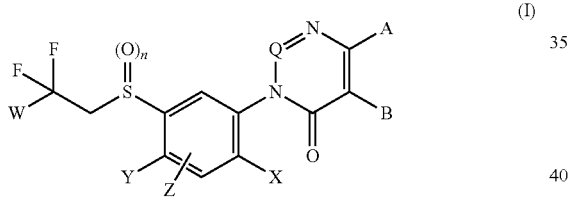

in which
A and B together with the carbon atoms to which they are attached represent an optionally substituted five-membered ring which may be interrupted by at least one or more heteroatoms;
W represents hydrogen or halogen;
Q represents C—V or nitrogen;
V represents hydrogen, hydroxy, halogen, cyano, alkyl, cycloalkyl, haloalkyl, alkoxy, haloalkoxy, alkylthio, haloalkylthio, alkylsulphinyl, haloalkylsulphinyl, alkylsulphonyl, haloalkylsulphonyl, amino, monoalkylamino or dialkylamino;
X, Y and Z independently of one another represent hydrogen, halogen, hydroxy, amino, cyano, nitro, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represent optionally substituted phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl;

or represent optionally substituted saturated or unsaturated cycloalkyl, cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl, cycloalkylalkylsulphonyl or cycloalkenyl;

or represent $NR^4R^5$, where $R^4$ and $R^5$ independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl, alkoxycarbonyl, or $R^4$ and $R^5$ together with the nitrogen atom to which they are attached may form an optionally substituted saturated or unsaturated five- to eight-membered ring which is optionally interrupted by heteroatoms from the group consisting of O, S and N;

or represent a 3- to 6-membered saturated, partially saturated or aromatic ring which may optionally contain one to three heteroatoms from the group consisting of O, S and N and which is optionally mono- or polysubstituted by identical or different substituents from the group consisting of halogen, cyano, nitro, hydroxy, amino, carboxy, alkyl, haloalkyl, alkenyl, haloalkenyl, alkynyl, alkoxy, haloalkoxy, alkylthio, alkylsulphinyl, alkylsulphonyl, alkylsulphonyloxy, haloalkylthio, haloalkylsulphinyl, haloalkylsulphonyl, alkylamino, dialkylamino, alkylcarbonylamino, alkoxycarbonyl, alkylcarbonyl, alkylcarbonyloxy, aminocarbonyl, alkylaminocarbonyl, dialkylaminocarbonyl, aminothiocarbonyl, alkylaminothiocarbonyl, dialkylaminothiocarbonyl, cycloalkylamino, alkylsulphonylamino, aminosulphonyl, alkylaminosulphonyl and dialkylaminosulphonyl, or by optionally substituted cycloalkyl, cycloalkoxy, cycloalkylalkyl or cycloalkylalkoxy which are optionally interrupted by heteroatoms from the group consisting of O, S and N;

or X and Y or Y and Z form, together with the carbon atoms to which they are attached, a 5- or 6-membered ring which is optionally substituted and optionally interrupted by heteroatoms from the group consisting of O, S, N and CO;

and n represents the number 0, 1 or 2.

A2. Compounds according to Embodiment A1, characterized in that in the general formula (I)

A and B together with the carbon atoms to which they are attached represent a substructure selected from the group consisting of I-1 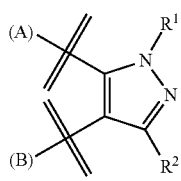
I-2 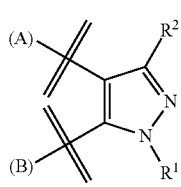
I-3 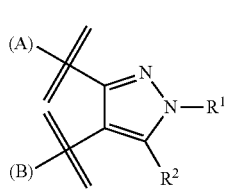
I-4 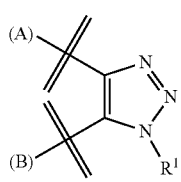
I-5 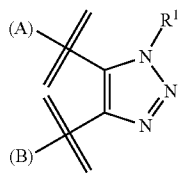
I-6 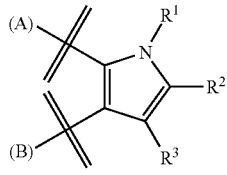
I-7 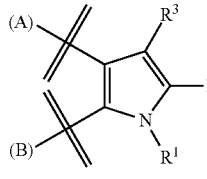
I-8 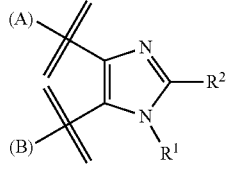
-continued
I-9 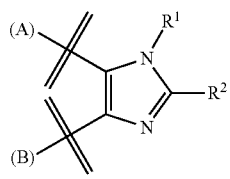
I-10 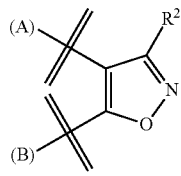
I-11 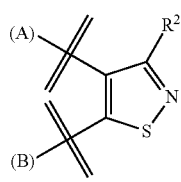
I-12 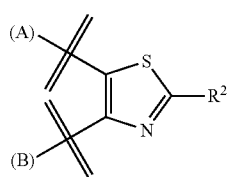
I-13 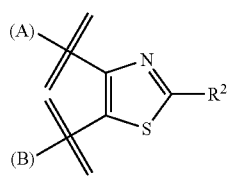
I-14 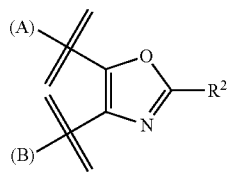
I-15 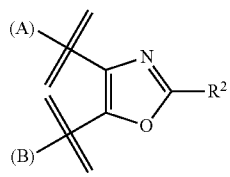
I-16 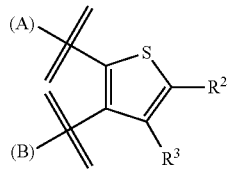

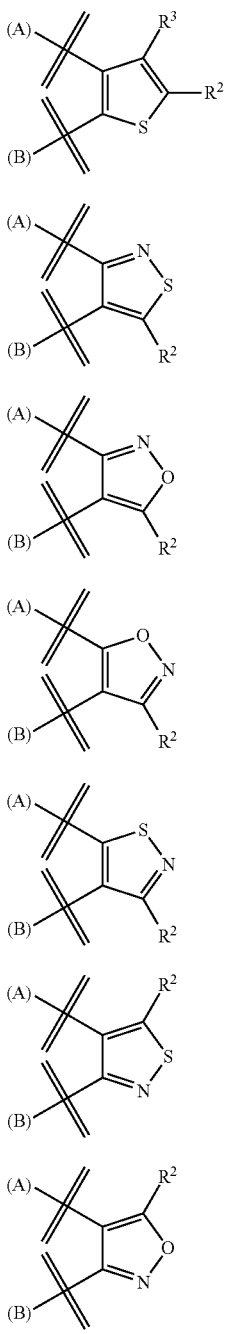

in which the labels (A) and (B) define the respective points of attachment of the radicals A and B of the general formula (I) and $R^1$, $R^2$ and $R^3$ have the following meanings:

$R^1$ represents hydrogen, optionally substituted alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkylcarbonyl, alkoxycarbonyl, haloalkoxycarbonyl, haloalkylcarbonyl, alkoxycarbonylalkyl, alkylthioalkyl, haloalkylthioalkyl, alkoxyalkylthioalkyl, alkylsulphinylalkyl, haloalkylsulphinylalkyl, alkoxyalkylsulphinylalkyl, alkylsulphonylalkyl, haloalkylsulphonylalkyl, alkoxyalkylsulphonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represents optionally substituted phenyl, phenylalkyl, phenoxyalkyl, phenylthioalkyl, hetaryl or hetarylalkyl;

or represents optionally substituted saturated or unsaturated cycloalkyl which may optionally be interrupted by one or more heteroatoms, or represents cycloalkylalkyl;

$R^2$ and $R^3$ independently of one another represent hydrogen, halogen, hydroxy, amino, cyano, nitro, OCN, SCN, $SF_5$, trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulphinyl, haloalkylsulphinyl, alkoxyalkylsulphinyl, alkylsulphinylalkyl, alkylsulphonyl, haloalkylsulphonyl, alkoxyalkylsulphonyl, alkylsulphonylalkyl, alkylsulphonyloxy, alkylcarbonyl, haloalkylcarbonyl, carboxyl, alkylcarbonyloxy, alkoxycarbonyl, haloalkoxycarbonyl, alkoxycarbonylalkyl, aminocarbonyl, alkylaminocarbonyl, dialkylaminocarbonyl, alkenylaminocarbonyl, dialkenylaminocarbonyl, cycloalkylaminocarbonyl, alkylsulphonylamino, aminosulphonyl, alkylaminosulphonyl, dialkylaminosulphonyl, alkylsulphoximino, aminothiocarbonyl, alkylaminothiocarbonyl or dialkylaminothiocarbonyl;

or represent optionally substituted phenylalkyl, phenoxy, phenylalkyloxy, phenoxyalkyl, phenylthio, phenylthioalkyl, phenylsulphinyl, phenylsulphonyl, hetarylalkyl, hetaryloxy, hetarylalkyloxy, hetarylthio, hetarylsulphinyl or hetarylsulphonyl;

or represent optionally substituted saturated or unsaturated cycloalkylalkyl, cycloalkyloxy, cycloalkylalkoxy, cycloalkylthio, cycloalkylalkylthio, cycloalkylsulphinyl, cycloalkylalkylsulphinyl, cycloalkylsulphonyl or cycloalkylalkylsulphonyl;

W represents hydrogen or halogen;

Q represents C—V or nitrogen;

V represents hydrogen, hydroxy, halogen, cyano, $(C_1-C_6)$-alkyl, $(C_3-C_8)$-cycloalkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphinyl, $(C_1-C_6)$-haloalkylsulphinyl, $(C_1-C_6)$-alkylsulphonyl, $(C_1-C_6)$-haloalkylsulphonyl, amino, $(C_1-C_6)$-alkylamino or $(C_1-C_6)$-dialkylamino;

X, Y and Z independently of one another represent hydrogen, halogen, hydroxy, amino, cyano, nitro, OCN, SCN, $SF_5$, tri-$(C_1-C_6)$-alkylsilyl, $(C_1-C_6)$-alkyl, $(C_1-C_6)$-haloalkyl, $(C_1-C_6)$-cyanoalkyl, $(C_1-C_6)$-hydroxyalkyl, $(C_1-C_6)$-alkoxycarbonyl-$(C_1-C_4)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-cyanoalkoxy, hydroxycarbonyl-$(C_1-C_4)$-alkoxy, $(C_1-C_7)$-alkoxycarbonyl-$(C_1-C_7)$-alkoxy, $(C_1-C_6)$-alkoxy-$(C_1-C_6)$-alkoxy, $(C_1-C_7)$-alkylhydroxyimino, $(C_1-C_7)$-alkoxyimino, $(C_1-C_6)$-alkyl-$(C_1-C_7)$-alkoxyimino, halo-$(C_1-$ $C_6$)-alkyl-($C_1$-$C_7$)-alkoxyimino, ($C_1$-$C_6$)-alkylthio, halo-($C_1$-$C_6$)-alkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_7$)-alkylcarbonyl, ($C_1$-$C_7$)-haloalkylcarbonyl, carboxyl, ($C_1$-$C_7$)-alkylcarbonyloxy, ($C_1$-$C_7$)-alkoxycarbonyl, ($C_1$-$C_7$)-haloalkoxycarbonyl, ($C_1$-$C_7$)-alkoxycarbonyl-($C_1$-$C_6$)-alkyl, aminocarbonyl, ($C_1$-$C_7$)-alkylaminocarbonyl, di-($C_1$-$C_7$)-alkylaminocarbonyl, ($C_2$-$C_7$)-alkenylaminocarbonyl, di-($C_2$-$C_7$)-alkenylaminocarbonyl, ($C_3$-$C_8$)-cycloalkylaminocarbonyl, ($C_1$-$C_6$)-alkylsulphonylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl or di-($C_1$-$C_6$)-alkylaminothiocarbonyl;

or represent phenyl-($C_1$-$C_6$)-alkyl, phenoxy, phenyl-($C_1$-$C_4$)-alkyloxy, phenoxy-($C_1$-$C_4$)-alkyl, phenylthio, phenylthio-($C_1$-$C_4$)-alkyl, phenylsulphinyl, phenylsulphonyl, hetaryl-($C_1$-$C_6$)-alkyl, hetaryloxy, hetaryl-($C_1$-$C_4$)-alkyloxy, hetarylthio, hetarylsulphinyl, hetarylsulphonyl, optionally saturated or unsaturated ($C_3$-$C_8$)-cycloalkyl-($C_1$-$C_6$)-alkyl, ($C_3$-$C_8$)-cycloalkyloxy, ($C_3$-$C_8$)-cycloalkyl-($C_1$-$C_6$)-alkoxy, ($C_3$-$C_8$)-cycloalkylthio, ($C_3$-$C_8$)-cycloalkyl-($C_1$-$C_6$)-alkylthio, ($C_3$-$C_8$)-cycloalkylsulphinyl, ($C_3$-$C_8$)-cycloalkyl-($C_1$-$C_6$)-alkylsulphinyl, ($C_3$-$C_8$)-cycloalkylsulphonyl or ($C_3$-$C_8$)-cycloalkyl-($C_1$-$C_6$)-alkylsulphonyl, substituted by optionally saturated or unsaturated ($C_3$-$C_8$)-cycloalkyl, ($C_3$-$C_8$)-cycloalkoxy, ($C_3$-$C_8$)-cycloalkyl-($C_1$-$C_6$)-alkyl or ($C_3$-$C_8$)-cycloalkyl-($C_1$-$C_6$)-alkoxy optionally substituted by identical or different substituents from the group consisting of halogen, cyano, nitro, hydroxy, amino, carboxy, ($C_1$-$C_6$)-alkyl, ($C_1$-$C_6$)-haloalkyl, ($C_2$-$C_7$)-alkenyl, ($C_2$-$C_7$)-haloalkenyl, ($C_2$-$C_6$)-alkynyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphonyloxy, ($C_1$-$C_6$)-haloalkylthio, ($C_1$-$C_6$)-haloalkylsulphinyl, ($C_1$-$C_6$)-haloalkylsulphonyl, ($C_1$-$C_6$)-alkylamino, di-($C_1$-$C_6$)-alkylamino, ($C_1$-$C_7$)-alkylcarbonylamino, ($C_1$-$C_7$)-alkoxycarbonyl, ($C_1$-$C_7$)-alkylcarbonyl, ($C_1$-$C_7$)-alkylcarbonyloxy, aminocarbonyl, ($C_1$-$C_6$)-alkylaminocarbonyl, di-($C_1$-$C_6$)-alkylaminocarbonyl, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, ($C_1$-$C_6$)-alkylsulphonylamino, aminosulphonyl, ($C_1$-$C_6$)-alkylaminosulphonyl and di-($C_1$-$C_6$)-alkylaminosulphonyl and optionally interrupted by one or two heteroatoms from the group consisting of O, S and N;

or represent $NR^4R^5$ where $R^4$ and $R^5$ independently of one another represent hydrogen, cyano, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-alkyl-($C_1$-$C_6$)-thioalkyl, ($C_2$-$C_7$)-alkenyl, ($C_2$-$C_7$)-haloalkenyl, ($C_2$-$C_7$)-cyanoalkenyl, ($C_2$-$C_6$)-alkynyl, ($C_2$-$C_6$)-haloalkynyl, ($C_2$-$C_6$)-cyanoalkynyl, acyl or ($C_1$-$C_7$)-alkoxycarbonyl, or $R^4$ and $R^5$ together with the nitrogen atom to which they are attached may form a saturated or unsaturated five- to seven-membered ring which is optionally substituted by identical or different substituents from the group consisting of halogen, cyano, hydroxy, amino, ($C_1$-$C_6$)-alkyl, ($C_1$-$C_6$)-haloalkyl, ($C_1$-$C_6$)-alkoxy, ($C_1$-$C_6$)-haloalkoxy or by ($C_3$-$C_8$)-cycloalkyl or ($C_3$-$C_8$)-cycloalkyl-($C_1$-$C_6$)-alkyl optionally substituted by identical or different substituents from the group consisting of halogen, cyano, ($C_1$-$C_6$)-alkyl, ($C_1$-$C_6$)-alkoxy or ($C_1$-$C_6$)-haloalkyl and optionally interrupted by heteroatoms from the group consisting of O, S and N and is optionally interrupted by heteroatoms from the group consisting of O, S and N;

or represent ($C_3$-$C_8$)-cycloalkyl, ($C_3$-$C_8$)-cycloalkoxy, ($C_3$-$C_8$)-cycloalkyl-($C_1$-$C_4$)-alkyl, ($C_3$-$C_8$)-cycloalkyl-($C_1$-$C_6$)-alkoxy, ($C_3$-$C_8$)-cycloalkylthio, ($C_3$-$C_8$)-cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl which is optionally mono- or polysubstituted by identical or different substituents from the group consisting of halogen, cyano, nitro, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphonyloxy, ($C_1$-$C_6$)-haloalkylthio, ($C_1$-$C_6$)-haloalkylsulphinyl, ($C_1$-$C_6$)-haloalkylsulphonyl, or by ($C_3$-$C_8$)-cycloalkyl, ($C_3$-$C_8$)-cycloalkoxy, ($C_3$-$C_8$)-cycloalkyl-($C_1$-$C_4$)-alkyl, ($C_3$-$C_8$)-cycloalkyl-($C_1$-$C_6$)-alkoxy, ($C_3$-$C_8$)-cycloalkylthio and ($C_3$-$C_8$)-cycloalkenyl, optionally substituted by halogen, cyano, ($C_1$-$C_6$)-alkyl, ($C_1$-$C_6$)-alkoxy, ($C_1$-$C_6$)-haloalkyl and optionally interrupted by heteroatoms from the group consisting of O, S and N;

or X and Z or Y and Z may form one of the following 5- or 6-membered rings which are optionally substituted by identical or different substituents from the group consisting of halogen, cyano, ($C_1$-$C_6$)-alkyl, ($C_3$-$C_8$)-cycloalkyl, ($C_1$-$C_6$)-haloalkyl, ($C_3$-$C_8$)-halocycloalkyl, ($C_1$-$C_6$)-alkoxy and ($C_1$-$C_6$)-haloalkoxy,

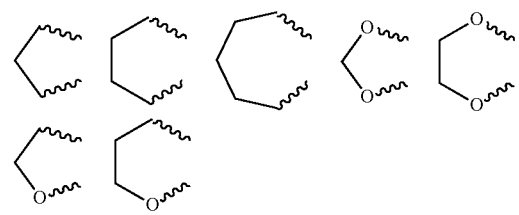

or X and Z or Y and Z may form the following fused rings which are optionally mono- or polysubstituted by identical or different substituents, where the substituents independently of one another may be selected from the group consisting of hydrogen, halogen, cyano, ($C_1$-$C_6$)-alkyl, ($C_3$-$C_8$)-cycloalkyl, ($C_1$-$C_6$)-haloalkyl, ($C_3$-$C_8$)-halocycloalkyl, ($C_1$-$C_6$)-alkoxy, ($C_1$-$C_6$)-haloalkoxy, ($C_1$-$C_6$)-alkoxy-($C_1$-$C_6$)-alkyl, ($C_1$-$C_6$)-alkylthio, ($C_1$-$C_6$)-alkylsulphonyl, amino, ($C_1$-$C_6$)-alkylamino, di-($C_1$-$C_6$)-alkylamino and ($C_3$-$C_8$)-cycloalkylamino,

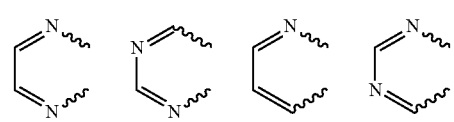

-continued

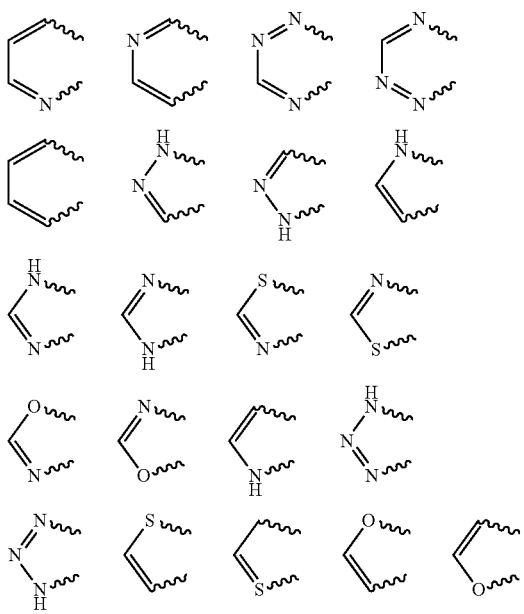

and n represents the number 0, 1 or 2.

A3. Compounds according to Embodiment A1 or A2, characterized in that in the general formula (I)

A and B together with the carbon atoms to which they are attached represent a substructure selected from the group consisting of

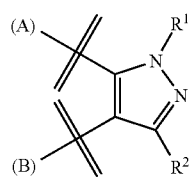

I-1

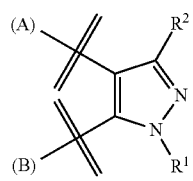

I-2

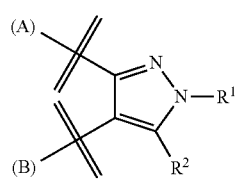

I-3

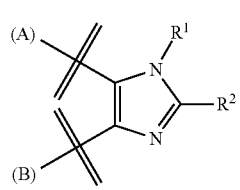

I-9

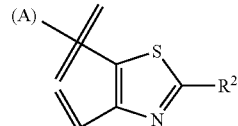

I-12

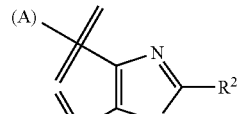

I-13

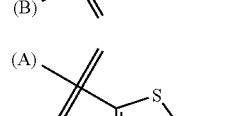

I-16

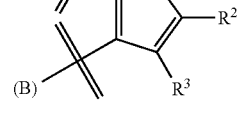

I-17

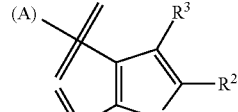

I-18

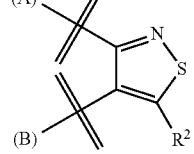

in which the labels (A) and (B) define the respective points of attachment of the radicals A and B of the general formula (I) and $R^1$, $R^2$ and $R^3$ have the following meanings:

$R^1$ represents hydrogen, methyl, ethyl, propyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represents cyclopropyl, cyclobutyl, cyclopentyl or cyclohexyl which are mono- or polysubstituted by identical or different substituents from the group consisting of fluorine, chlorine, bromine, cyano, nitro, methyl, ethyl and trifluoromethyl;

or represents cyclopropylmethyl or cyclobutylmethyl which are mono- or polysubstituted by identical or different substituents from the group consisting of fluorine, chlorine, bromine, cyano, nitro, methyl, ethyl and trifluoromethyl;

$R^2$ and $R^3$ independently of one another represent hydrogen, fluorine, chlorine, bromine, iodine, hydroxy, amino, cyano, nitro, OCN, SCN, $SF_5$, trimethylsilyl, methyl, ethyl, propyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represent cyclopropyl, cyclobutyl, cyclopentyl or cyclohexyl which are mono- or polysubstituted by identical or different substituents from the group consisting of fluorine, chlorine, bromine, cyano, nitro, methyl, ethyl and trifluoromethyl;

or represent cyclopropylmethyl or cyclobutylmethyl which are mono- or polysubstituted by identical or different substituents from the group consisting of fluorine, chlorine, bromine, cyano, nitro, methyl, ethyl and trifluoromethyl;

Q represents C—V or nitrogen; where

V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl, (2,2)-difluoroethyl;

W represents hydrogen or fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

A4. Compounds according to any of Embodiments A1 to A3, characterized in that in the general formula (I)

A and B together with the carbon atoms to which they are attached represent the radical

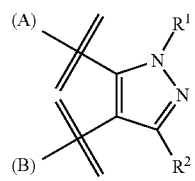

in which $R^1$ and $R^2$ have the meanings according to one of Embodiments A2 and A3, in particular hydrogen, methyl, ethyl, cyclopropyl or (2,2,2)-trifluoroethyl;

Q represents C—V or nitrogen; where

V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl or (2,2)-difluoroethyl;

W represents hydrogen or fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

A5. Compounds according to any of Embodiments A1 to A3, characterized in that in the general formula (I)

A and B together with the carbon atoms to which they are attached represent the radical

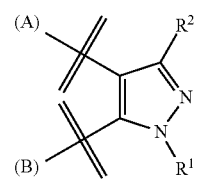

in which $R^1$ and $R^2$ have the meanings according to one of Embodiments A2 and A3, in particular hydrogen, methyl, ethyl, cyclopropyl or (2,2,2)-trifluoroethyl;

Q represents C—V or nitrogen; where

V represents hydrogen, fluorine, chlorine, bromine, methyl, ethyl, propyl, butyl, sec-butyl, isopropyl, tert-butyl, trifluoromethyl, (2,2,2)-trifluoroethyl, difluoromethyl or (2,2)-difluoroethyl;

W represents hydrogen or fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

A6. Compounds according to any of Embodiments A1 to A3, characterized in that in the general formula (I)

A and B together with the carbon atoms to which they are attached represent the radical

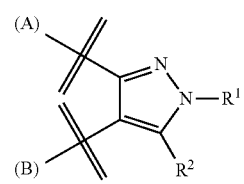

in which $R^1$ and $R^2$ have the meanings according to one of Embodiments A2 and A3, in particular hydrogen, methyl, ethyl, cyclopropyl or (2,2,2)-trifluoroethyl;

Q represents C—V or nitrogen; where

V represents hydrogen, methyl, ethyl or trifluoromethyl;

W represents fluorine;

X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;

Z represents hydrogen;

n represents the number 0 or 1.

A7. Compounds according to any of Embodiments A1 to A3, characterized in that in the general formula (I)

A and B together with the carbon atoms to which they are attached represent the radical

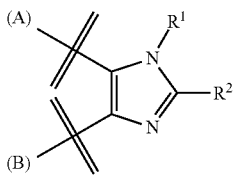

in which R¹ and R² have the meanings according to one of Embodiments A2 and A3, in particular hydrogen, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A8. Compounds according to any of Embodiments A1 to A3, characterized in that in the general formula (I) A and B together with the carbon atoms to which they are attached represent the radical

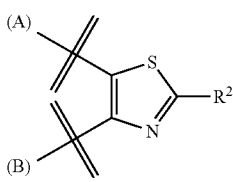

in which R² has the meaning according to one of Embodiments A2 and A3, in particular hydrogen, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A9. Compounds according to any of Embodiments A1 to A3, characterized in that in the general formula (I) A and B together with the carbon atoms to which they are attached represent the radical

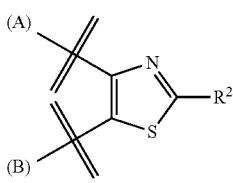

in which R² has the meaning according to one of Embodiments A2 and A3, in particular hydrogen, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A10. Compounds according to any of Embodiments A1 to A3, characterized in that in the general formula (I) A and B together with the carbon atoms to which they are attached represent the radical

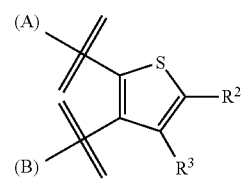

in which R² and R³ have the meanings according to one of Embodiments A2 and A3, in particular hydrogen, methyl, ethyl, cyclopropyl or (2,2,2)-trifluoroethyl;
Q represents C—V or nitrogen, where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A11. Compounds according to any of Embodiments A1 to A3, characterized in that in the general formula (I) A and B together with the carbon atoms to which they are attached represent the radical

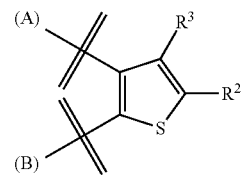

in which R² and R³ have the meanings according to one of Embodiments A2 and A3, in particular hydrogen, fluorine, chlorine, methyl, ethyl, cyclopropyl or (2,2,2)-trifluoroethyl;
Q represents C—V or nitrogen; where
V represents hydrogen, methyl, ethyl, trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A12. Compounds according to any of Embodiments A1 to A3, characterized in that in the general formula (I)

A and B together with the carbon atoms to which they are attached represent the radical

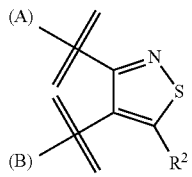

I-18 in which R² has the meaning according to one of Embodiments A2 and A3, in particular hydrogen, methyl, ethyl, cyclopropyl, tert-butyl or (2,2,2)-trifluoroethyl;
Q represents C—V or nitrogen; where
V represents hydrogen, methyl, ethyl or trifluoromethyl;
W represents fluorine;
X and Y independently of one another represent hydrogen, fluorine, chlorine, bromine, methyl, ethyl, trifluoromethyl, (2,2)-difluoromethyl, difluoromethoxy, trifluoromethoxy, cyano or nitro;
Z represents hydrogen;
n represents the number 0 or 1.

A13. Active compound composition comprising at least one compound of the general formula (I) according to any of Embodiments A1 to A12 and at least one further insecticidally, acaricidally or nematicidally active compound selected from the group consisting of (1) Acetylcholinesterase (AChE) inhibitors such as, for example,
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists such as, for example,
cyclodiene organochlorines, e.g. chlordane and endosulfan; or
phenylpyrazoles (fiprole), e.g. ethiprole and fipronil.

(3) Sodium channel modulators/voltage-dependent sodium channel blockers such as, for example,
pyrethroids, e.g. acrinathrin, allethrin, d-cis-trans allethrin, d-trans allethrin, bifenthrin, bioallethrin, bioallethrin s-cyclopentenyl isomer, bioresmethrin, cyprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin; or
DDT; or methoxychlor.

(4) Nicotinergic acetylcholine receptor (nAChR) agonists such as, for example,
neonicotinoids, e.g. acetamiprid, clothianidin, dinotefuran, imidacloprid, nitenpyram, thiacloprid and thiamethoxam; or
nicotine.

(5) Nicotinergic acetylcholine receptor (nAChR) allosteric activators such as, for example,
spinosyns, e.g. spinetoram and spinosad.

(6) Chloride channel activators such as, for example,
avermectins/milbemycins, for example abamectin, emamectin benzoate, lepimectin and milbemectin.

(7) Juvenile hormone imitators such as, for example,
juvenile hormone analogues, e.g. hydroprene, kinoprene and methoprene; or
fenoxycarb; or pyriproxyfen.

(8) Active compounds with unknown or nonspecific mechanisms of action such as, for example,
alkyl halides, e.g. methyl bromide and other alkyl halides; or
chloropicrin; or sulphuryl fluoride; or borax; or tartar emetic.

(9) Selective antifeedants, for example pymetrozine; or flonicamid.

(10) Mite growth inhibitors, for example clofentezine, hexythiazox and diflovidazin; or
etoxazole.

(11) Microbial disruptors of the insect gut membrane, for example Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron; or
organotin compounds, e.g. azocyclotin, cyhexatin and fenbutatin oxide; or
propargite; or tetradifon.

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocyclam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Moulting disruptors, dipteran, such as, for example, cyromazine.

(18) Ecdysone receptor agonists such as, for example, chromafenozide, halofenozide, methoxyfenozide and tebufenozide.
(19) Octopaminergic agonists such as, for example, amitraz.
(20) Complex-III electron transport inhibitors such as, for example, hydramethylnone; or acequinocyl; or fluacrypyrim.
(21) Complex-I electron transport inhibitors, for example METI acaricides, e.g. fenazaquin, fenpyroximate, pyrimidifen, pyridaben, tebufenpyrad and tolfenpyrad; or rotenone (Denis).
(22) Voltage-dependent sodium channel blockers, for example indoxacarb; or metaflumizone.
(23) Inhibitors of acetyl-CoA carboxylase such as, for example,
tetronic and tetramic acid derivatives, e.g. spirodiclofen, spiromesifen and spirotetramat.
(24) Complex-IV electron transport inhibitors such as, for example,
phosphines, e.g. aluminium phosphide, calcium phosphide, phosphine and zinc phosphide; or
cyanide.
(25) Complex-II electron transport inhibitors such as, for example, cyenopyrafen.
(28) Ryanodine receptor effectors such as, for example, diamides, for example chlorantraniliprole and flubendiamide.
Further active compounds having an unknown mechanism of action, such as, for example, amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulphone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM I-1582, for example VOTiVO™, BioNem), and the following known active compounds: 3-bromo-N-{2-bromo-4-chloro-6-[(1-cyclopropylethyl) carbamoyl]phenyl}-1-(3-chloropyridin-2-yl)-1H-pyrazole-5-carboxamide, 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), flupyradifurone, 4-{[(6-chloro-5-fluoropyrid-3-yl)methyl](methyl)amino}furan-2(5H)-one (known from WO 2007/115643), 4-{[(5,6-dichloropyrid-3-yl)methyl] (2-fluoroethyl)amino}furan-2(5H)-one (known from WO 2007/115646), 4-{[(6-chloro-5-fluoropyrid-3-yl)methyl] (cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl) amino}furan-2(5H)-one (known from EP-A-0 539 588), {[1-(6-chloropyridin-3-yl)ethyl](methyl)oxido-$\lambda^4$-sulphanylidene}cyanamide (known from WO 2007/149134) and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl) oxido-$\lambda^4$-sulphanylidene}cyanamide (B) (likewise known from WO 2007/149134) and also sulfoxaflor and its diastereomers [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene]cyanamide (A2), identified as diastereomer group A (known from WO 2010/074747, WO 2010/074751), [(R)-methyl (oxido){(1S)-1-[6-(trifluoromethyl)pyridin-3-yl]ethyl}-$\lambda^4$-sulphanylidene]cyanamide (B1) and [(S)-methyl (oxido){(1R)-1-[6-(trifluoromethyl)pyridin-3-yl]ethyl}-$\lambda^4$-sulphanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulphinyl]phenyl}-3-(trifluoromethyl)-1H-1,2,4-triazole-5-amine (known from WO 2006/043635), [(3S, 4aR,12R,12aS,12bS)-3-[(cyclopropylcarbonyl)oxy]-6, 12-dihydroxy-4,12b-dimethyl-11-oxo-9-(pyridin-3-yl)-1, 3,4,4a,5,6,6a,12,12a,12b-decahydro-2H,11H-benzo[f] pyrano[4,3-b]chromen-4-yl] methylcyclopropanecarboxylate (known from WO 2008/066153), 2-cyano-3-(difluoromethoxy)-N,N-dimethylbenzenesulphonamide (known from WO 2006/056433), 2-cyano-3-(difluoromethoxy)-N-methylbenzenesulphonamide (known from WO 2006/100288), 2-cyano-3-(difluoromethoxy)-N-ethylbenzenesulphonamide (known from WO 2005/035486), 4-(difluoromethoxy)-N-ethyl-N-methyl-1,2-benzothiazole-3-amine 1,1-dioxide (known from WO 2007/057407), N-[1-(2,3-dimethylphenyl)-2-(3,5-dimethylphenyl)ethyl]-4,5-dihydro-1,3-thiazole-2-amine (known from WO 2008/104503), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO 2009/049851), 3-(2,5-dimethylphenyl)-8-methoxy-2-oxo-1,8-diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl) (3,3,4,4,4-pentafluorobutyl)malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), flometoquin, PF1364 (CAS Reg. No. 1204776-60-2) (known from JP2010/018586), 5-[5-(3,5-dichlorophenyl)-5-(trifluoromethyl)-4,5-dihydro-1, 2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl) methyl](cyclopropyl)amino}-1,3-oxazol-2(5H)-one, 4-{[(6-chloropyridin-3-yl)methyl](2,2-difluoroethyl) amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2 (5H)-one (all known from WO 2010/005692), NNI-0711 (known from WO 2002/096882), 1-acetyl-N-[4-(1,1,1,3, 3,3-hexafluoro-2-methoxypropan-2-yl)-3-isobutylphenyl]-N-isobutyryl-3,5-dimethyl-1H-pyrazole-4-carboxamide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO 2005/085216), methyl 2-[3,5-dibromo-2({[3-bromo-1-(3-chloropyridin-2-yl)-1H-pyrazol-5-yl]carbonyl}amino)benzoyl]-1,2-diethylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO 2010/069502), (1E)-N-[(6-chloropyridin-3-yl)methyl]-N'-cyano-N-(2,2-difluoroethyl)ethanimidamide (known from WO 2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO 2011/049233), and/or at least one further fungicidally active compound selected from the group consisting of (1) Inhibitors of ergosterol biosynthesis such as, for example, (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulphate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]1H-imidazole-1-carbothioate (111226-71-2).

(2) Respiration inhibitors (respiratory chain inhibitors) such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR,9RS and the anti-empimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0) (known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1, 4-methanonaphthalen-5-yl]-3-(difluoromethyl)-1-methyl-1H-pyrazole-4-carboxamide and (2.31) N-[(1R,4S)-9-(dichloromethylene-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain such as, for example, (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division such as, for example, (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity such as, for example, (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulphate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulphur and sulphur preparations such as, for example, calcium polysulphide (7704-34-9), (5.31) thiram (137-26-8), (5.32) tolylfluanid (731-27-1), (5.33) zineb (12122-67-7) and (5.34) ziram (137-30-4).

(6) Resistance inducers such as, for example, (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis such as, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors such as, for example, (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis such as, for example, (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis such as, for example, (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors such as, for example, (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis such as, for example, (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors such as, for example, (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers such as, for example, (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds such as, for example, (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulphonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulphonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenyl-prop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88)

N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazol-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulphate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds such as, for example, (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl) (2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulphonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

A14. Agrochemical compositions, characterized in that they comprise at least one compound of the formula (I) according to Embodiments A1 to A12 or a composition according to Embodiment A13 and also extenders and/or surfactants.

A15. Process for preparing agrochemical compositions, characterized in that compounds of the formula (I) according to Embodiments A1 to A12 or a composition according to Embodiment A13 are/is mixed with extenders and/or surfactants.

A16. Method for controlling animal pests, characterized in that compounds of the formula (I) according to Embodiments A1 to A12 or a composition according to Embodiment A13 are/is allowed to act on animal pests and/or their habitat.

A17. Use of compounds of the formula (I) according to any of Embodiments A1 to A12 or a composition according to Embodiment A13 for controlling animal pests in crop protection, in the protection of materials and/or in the veterinary sector.

Illustration of the Processes and Intermediates

The Preparation and Use Examples which follow illustrate the invention without limiting it. The products were characterized by 1H-NMR spectroscopy and/or LC/MS (Liquid Chromatography Mass Spectrometry).

The log P values were determined according to EEC directive 79/831 Annex V.A8 by HPLC (High Performance Liquid Chromatography) on reversed-phase columns (C 18), using the methods below:

[a] The LC-MS determination in the acidic range is carried out at pH 2.7 with 0.1% aqueous formic acid and acetonitrile (contains 0.1% formic acid) as mobile phases; linear gradient from 10% acetonitrile to 95% acetonitrile.

[b] The LC-MS determination in the neutral range is carried out at pH 7.8 using the mobile phases 0.001 molar aqueous ammonium bicarbonate solution and acetonitrile; linear gradient from 10% acetonitrile to 95% acetonitrile.

The calibration is effected with unbranched alkan-2-ones (having 3 to 16 carbon atoms) with known log P values (log P values determined on the basis of the retention times by linear interpolation between two successive alkanones).

The NMR spectra were determined using a Bruker Avance 400 fitted with a flow probe head (volume 60 µl). In individual cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), sept (septet), m (multiplet), br (for broad signals). Solvents used were $CD_3CN$, $CDCl_3$ or D6-DMSO, and tetramethylsilane (0.00 ppm) was used as reference.

The GC-MS spectra were determined using an Agilent 6890 GC, HP 5973 MSD on a dimethylsilicone phase, using a temperature gradient from 50° C. to 320° C. GC-MS indices are determined as Kovats indices using solutions of a homologous series of n-alkanes (having an even number of 8 to 38 carbon atoms).

Synthesis of Anilines of the Formulae (IVa), (IVb) and Intermediates (X), (XI), (XII), (XIII), (XVI), (XVII), (XVIII), (XIX) and (XX)

2,2,2-Trifluoro-N-(2-fluoro-4-methylphenyl)acetamide (XIII-1)

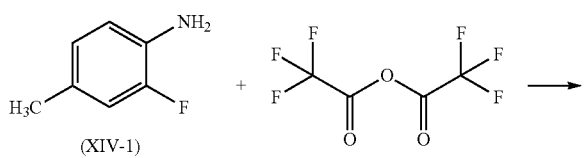

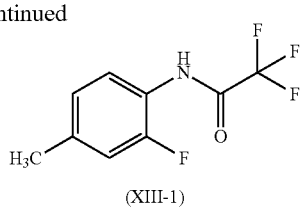

(XIII-1)

At 0° C., 27.5 g of 2-fluoro-4-methylaniline are initially charged in 300 ml of dichloromethane, 26.7 g of triethylamine are added and 50.8 g of trifluoroacetic anhydride are then added dropwise. The mixture is stirred at 0° C. for 2 h and then concentrated by rotary evaporation. The residue is taken up in water and extracted twice with ethyl acetate. The combined organic phases are dried over sodium sulphate and filtered and the solvent is removed under reduced pressure. This gives 49.0 g (100% of theory) of the title compound.

log P[a]: 2.40

The following was obtained analogously:

N-(4-Chloro-2-fluorophenyl)-2,2,2-trifluoroacetamide (XIII-2)

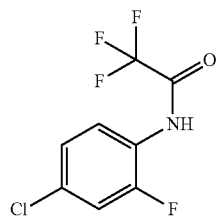

(XIII-2)

log P[a]: 2.53; log P[b]: 2.40; 1H-NMR (D6-DMSO, 400 MHz) δ ppm 11.29 (s, 1H), 7.62 (dd, 1H), 7.55 (dd, 1H), 7.37 (dd, 1H)

4-Fluoro-2-methyl-5-[(trifluoroacetyl)amino]benzenesulphonyl chloride (XII-1)

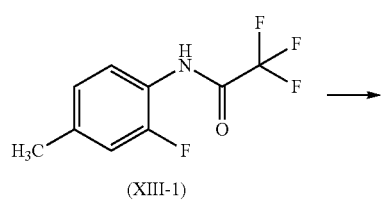

258 g of chlorosulphonic acid are initially charged, and 49 g of 2,2,2-trifluoro-N-(2-fluoro-4-methylphenyl)acetamide are added a little at a time at room temperature. The mixture is stirred at room temperature for another 16 h. With stirring, the mixture is added to ice and extracted twice with ethyl acetate. The combined organic phases are dried over sodium sulphate and filtered and the solvent is removed under reduced pressure. This gives 70.8 g of the chlorosulphonyl (XII-1). The crude product is immediately reacted further.

N,N'-[Disulphanediylbis(6-fluoro-4-methylbenzene-3,1-diyl)]bis(2,2,2-trifluoroacetamide) (XI-1)

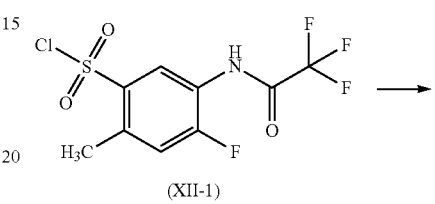

(XII-1)

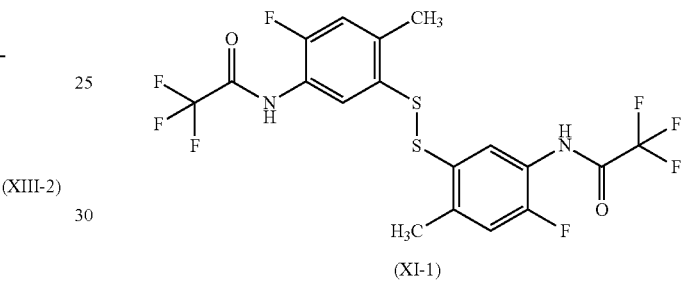

(XI-1)

298.8 g of sodium iodide are dissolved in 1000 ml of trifluoroacetic acid, and 70.8 g of 4-fluoro-2-methyl-5-[(trifluoroacetyl)amino]benzenesulphonyl chloride are added at room temperature. The mixture is stirred at room temperature for 16 h and the solvent is then removed under reduced pressure. The residue is triturated with water and filtered off with suction. This gives 62.3 g (86% of theory) of the title compound as a solid.

log P[a]: 4.41

The following was obtained analogously:

N,N'-[Disulphanediylbis(4-chloro-6-fluorobenzene-3,1-diyl)]bis(2,2,2-trifluoroacetamide) (XI-2)

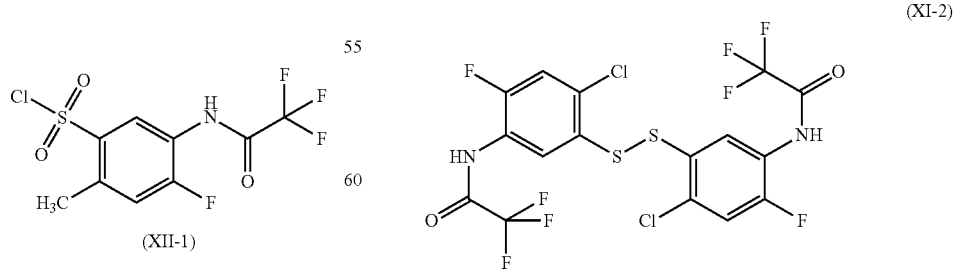

(XI-2)

log P[a]: 4.60; log P[b]: 3.82; 1H-NMR (D6-DMSO, 400 MHz) δ ppm 11.44 (s, 2H), 7.95 (d, 2H), 7.83 (d, 2H)

2,2,2-Trifluoro-N-{2-fluoro-4-methyl-5-[(2,2,2-trifluoroethyl)sulphanyl]phenyl}acetamide (X-1)

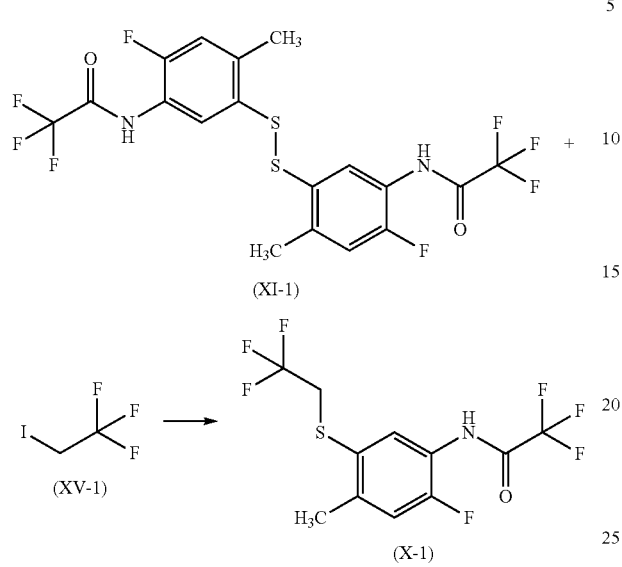

3.4 g of N,N'-[disulphanediylbis(6-fluoro-4-methylbenzene-3,1-diyl)]bis(2,2,2-trifluoroacetamide) are dissolved in 150 ml of N,N-dimethylformamide, and 1.86 g of potassium carbonate, 3.11 g of 1,1,1-trifluoroiodoethane, 2.39 g of Rongalit and a few drops of water are added. The reaction mixture is stirred at room temperature for 16 hours. Most of the N,N-dimethylformamide is distilled off under reduced pressure. The residue is taken up in water and extracted twice with ethyl acetate. The combined organic phases are dried over sodium sulphate and filtered, and the solvent is then removed under reduced pressure. This gives 4.48 g (90% of theory) of the title compound.

log P[a]: 3.31

The following was obtained analogously:

N-{4-Chloro-2-fluoro-5-[(2,2,2-trifluoroethyl)sulphanyl]phenyl}-2,2,2-trifluoroacetamide (X-2)

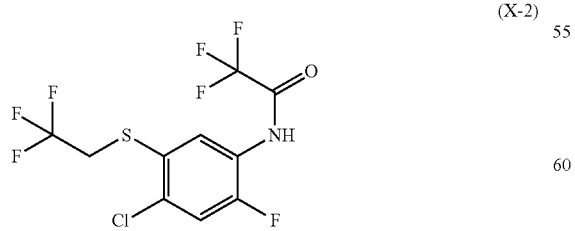

log P[a]: 3.34; log P[b]: 3.14; 1H-NMR (D6-DMSO, 400 MHz) δ ppm 11.47 (bs, 1H), 7.85 (d, 1H), 7.76 (d, 1H), 4.09 (q, 2H)

S-(5-Acetamido-4-fluoro-2-methylphenyl)ethanethioate (XVII-1)

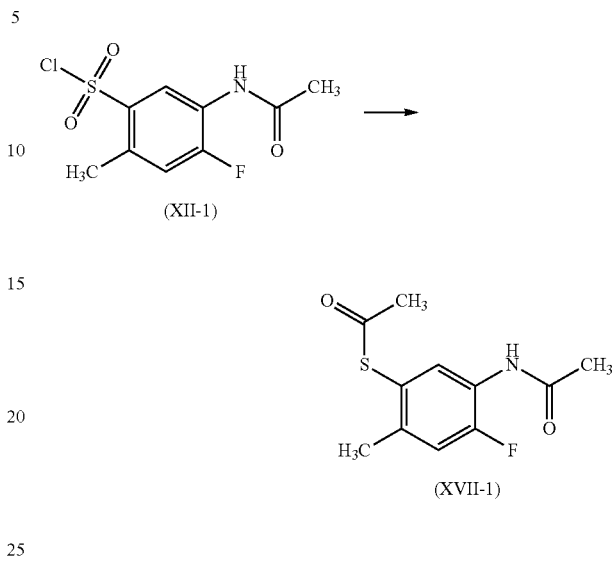

99.3 g of 5-acetamido-4-fluoro-2-methylbenzenesulphonyl chloride are suspended in 700 ml of glacial acetic acid, 0.9 g of iodine and 38.7 g of red phosphorus are added, and the mixture is stirred at reflux for 5 h. After cooling, the solid is filtered off and the filtrate is concentrated by rotary evaporation. The residue is triturated with water and filtered off with suction. This gives 57.6 g (67% of theory) of the title compound as a solid.

log P[a]: 1.78

5-Amino-4-fluoro-2-methylbenzenethiol (XVI-1)

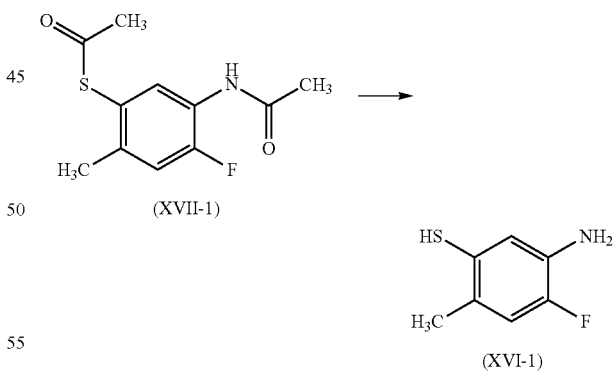

57.4 g of S-(5-acetamido-4-fluoro-2-methylphenyl)ethanethioate are dissolved in 750 ml of water and 96.6 g of potassium hydroxide. The reaction mixture is boiled at reflux for 16 hours. After cooling, the solution is adjusted to pH 2-3 using hydrochloric acid, and the precipitated solid is filtered off with suction. This gives 35.8 g (94% of theory) of the title compound as a solid.

log P[a]: 3.70

2-Fluoro-4-methyl-5-[(2,2,2-trifluoroethyl)sulphinyl]aniline (IVb-1)

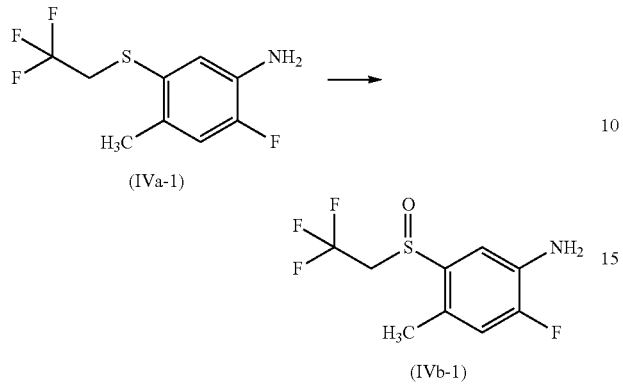

At 0-4° C., 5.00 g (0.21 mmol) of 2-fluoro-4-methyl-5-[(2,2,2-trifluoroethyl)sulphanyl]aniline are initially charged in 100 ml of dichloromethane, 6.18 g (0.25 mmol) of meta-chloroperbenzoic acid are added and the reaction mixture is stirred at room temperature for 2 h. A 33% strength sodium thiosulphate solution is then added (peroxide test carried out), and the mixture is extracted twice with dichloromethane. The combined organic phases are washed with a saturated sodium carbonate solution, dried over sodium sulphate and filtered, and the solvent is removed under reduced pressure. The residue comprises 5.10 g (90% pure, 86% of theory) of the title compound as a brown oil.

log P[a]: 1.77; log P[b]: 1.72; 1H-NMR (D6-DMSO, 400 MHz) δ ppm 7.26 (d, 1H), 7.02 (d, 1H), 5.45 (bs, 2H), 4.08-3.95 (m, 1H), 3.88-3.75 (m, 1H), 2.19 (s, 3H)

1,1'-Disulphanediylbis(2-chloro-5-nitrobenzene) (XIX-3)

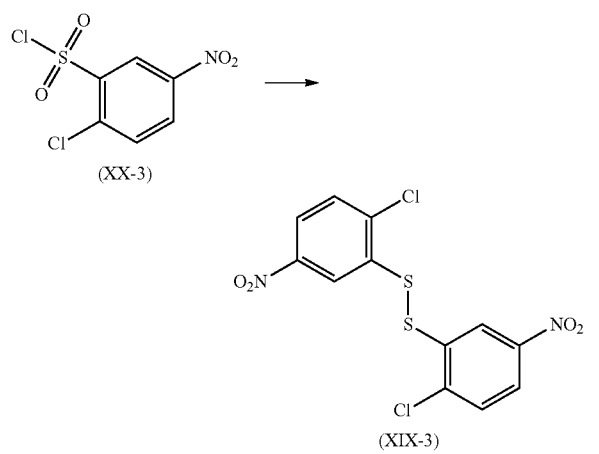

With vigorous stirring, 236.1 g (1.02 mol) of chlorosulphonic acid are added to 52.0 g (203.1 mmol) of 2-chloro-5-nitrobenzenesulphonyl chloride, and the mixture is stirred at room temperature overnight. After addition of 40% strength aqueous sodium bisulphite solution, the solid formed is filtered off with suction, washed with water and dried on a clay disc overnight. This gives 36.1 g (100% pure, 94% of theory) of the title compound as a grey-brown solid.

log P[a]: 5.03; log P[b]: 5.01; 1H-NMR (D6-DMSO, 400 MHz) δ ppm 8.40 (d, 2H), 8.18-8.16 (m, 2H), 7.91 (d, 2H); GC-MS: EI mass (m/z): 376 (2Cl) [M]+

The following were obtained analogously:

1,1'-Disulphanediylbis(4-chloro-3-nitrobenzene) (XIX-4)

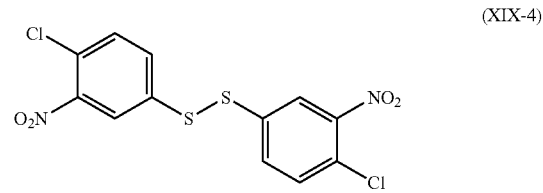 [SMILES: O=[N+]([O-])c1cc(SSc2ccc(Cl)c([N+](=O)[O-])c2)ccc1Cl]

log P[a]: 4.58; log P[b]: 4.58; 1H-NMR (D6-DMSO, 400 MHz) δ ppm 8.29 (d, 2H), 7.89-7.86 (m, 2H), 7.81 (d, 2H); GC-MS: EI mass (m/z): 376 (2Cl) [M]+

1,1'-Disulphanediylbis(4-fluoro-3-nitrobenzene) (XIX-5)

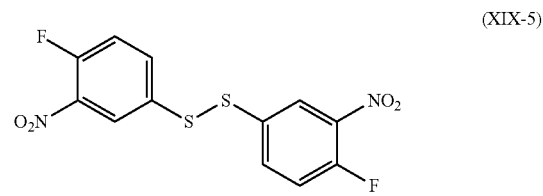 [SMILES: O=[N+]([O-])c1cc(SSc2ccc(F)c([N+](=O)[O-])c2)ccc1F]

log P[a]: 3.83; log P[b]: 3.79; 1H-NMR (D6-DMSO, 400 MHz) δ ppm 8.32-8.29 (m, 2H), 8.03-7.97 (m, 2H), 7.69-7.63 (m, 2H); GC-MS: EI mass (m/z): 344 [M]+

1,1'-Disulphanediylbis(2,4-dichloro-5-nitrobenzene) (XIX-6)

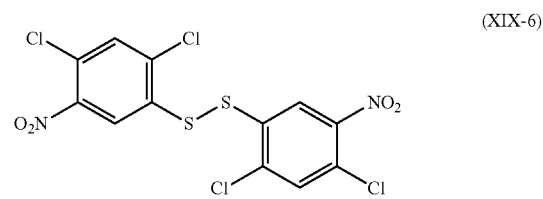 [SMILES: O=[N+]([O-])c1cc(SSc2cc([N+](=O)[O-])c(Cl)cc2Cl)c(Cl)cc1Cl]

log P[a]: 5.69; log P[b]: 5.64; 1H-NMR (D6-DMSO, 400 MHz) δ ppm 8.33 (s, 2H), 8.21 (s, 2H)

3,3'-Disulphanediylbis(4-chloroaniline) (XVIII-3)

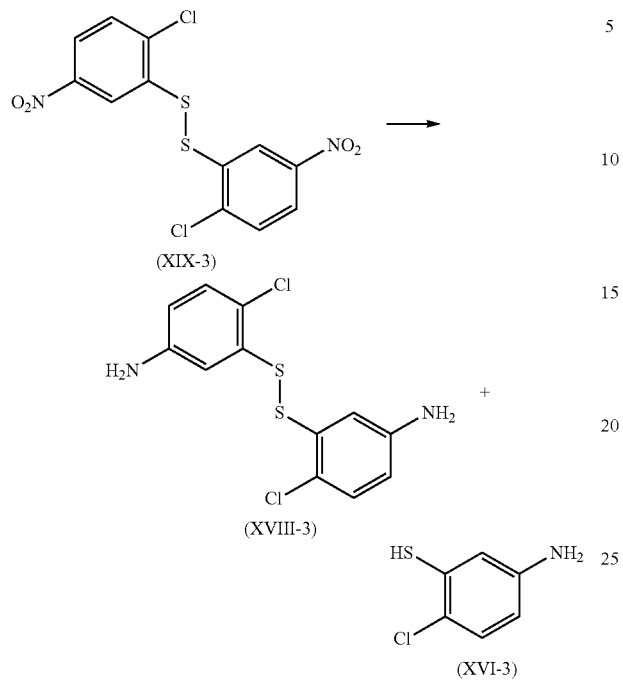

8.00 g (21.2 mmol) of 1,1'-disulphanediylbis(2-chloro-5-nitrobenzene) are dissolved in 150 ml of THF, 1.6 g of Raney nickel are added and the mixture is stirred at 50° C. under a hydrogen atmosphere (20 bar) for 72 h. Using THF, the reaction mixture is filtered through kieselguhr, and the filtrate is freed from the solvent under reduced pressure. This gives 6.64 g (90% pure, 89% of theory) of a mixture of 1,1'-disulphanediylbis(2-chloro-5-nitrobenzene) and 5-amino-2-chlorobenzenethiol which is alkylated without further purification.

1,1'-Disulphanediylbis(2-chloro-5-nitrobenzene) (XVIII-3)

log P[a]: 3.31; log P[b]: 3.35; 1H-NMR (D6-DMSO, 400 MHz) δ ppm 7.10 (d, 2H), 6.73 (d, 2H), 6.47-6.44 (m, 2H), 5.51 (broad, 4H); GC-MS: EI mass (m/z): 316 (2Cl) [M]+

5-Amino-2-chlorobenzenethiol (XVI-3)

log P[a]: 1.64; 1H-NMR (D6-DMSO, 400 MHz) δ ppm 7.01 (d, 1H), 6.54 (d, 1H), 6.35-6.32 (m, 1H), 5.28 (broad, 3H); GC-MS: EI mass (m/z): 159 (1Cl) [M]+

The following were obtained analogously:

3,3'-Disulphanediylbis(6-chloroaniline) (XVIII-4)

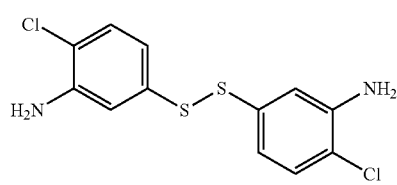

log P[a]: 3.84; log P[b]: 3.83; 1H-NMR (D6-DMSO, 400 MHz) δ ppm 7.18 (d, 2H), 6.94 (d, 2H), 6.65-6.62 (m, 2H), 5.59 (broad, 4H); GC-MS: EI mass (m/z): 316 (2Cl) [M]+

3,3'-Disulphanediylbis(6-fluoroaniline) (XVIII-5)

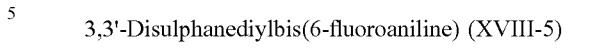

log P[a]: 2.98; log P[b]: 2.97; 1H-NMR (D6-DMSO, 400 MHz) δ ppm 7.02-6.95 (m, 2H), 6.95-6.82 (m, 2H), 6.62-6.57 (m, 2H), 5.40 (broad, 4H); GC-MS: EI mass (m/z): 284 [M]+

3,3'-Disulphanediylbis(4,6-dichloroaniline) (XVIII-6)

log P[a]: 5.14; log P[b]: 4.95; 1H-NMR (D6-DMSO, 400 MHz) δ ppm 7.41 (s, 2H), 6.95 (s, 2H), 5.78 (broad, 4H); GC-MS: EI mass (m/z): 386 (4Cl) [M]+

4-Chloro-3-[(2,2,2-trifluoroethyl)sulphanyl]aniline (IVa-3)

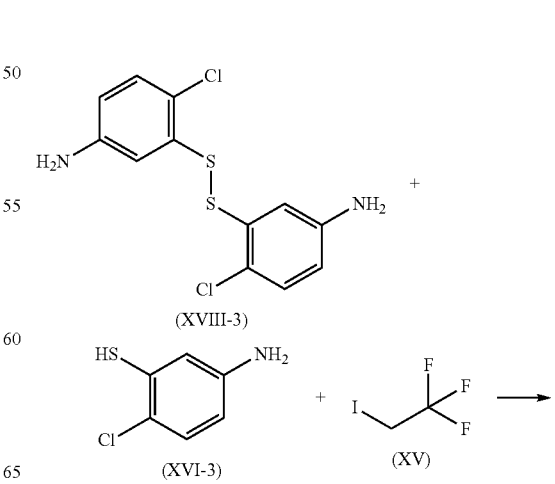

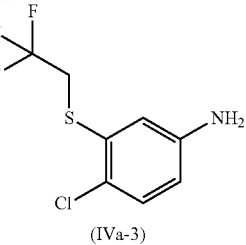

(IVa-3)

6.40 g of a mixture of disulphanediylbis(2-chloro-5-nitrobenzene) and 5-amino-2-chlorobenzenethiol (about 20 mmol) are initially charged in 100 ml of N,N-dimethylformamide, and 7.02 g (40.3 mmol) of sodium dithionite, 5.58 g (40.3 mmol) of potassium carbonate and 5.49 g (40.3 mmol) of Rongalit are added and the mixture is cooled to 0° C. 9.32 g of 1,1,1-trifluoro-2-iodoethane are added dropwise at 0° C. The reaction mixture is stirred at room temperature overnight. Most of the solvent is removed under reduced pressure, water is added to the residue and the mixture is extracted with ethyl acetate. The combined organic phases are washed successively with water and saturated aqueous sodium chloride solution, dried over magnesium sulphate, filtered and freed from the solvent under reduced pressure. Purification by column chromatography on silica gel by means of MPLC using the mobile phase cyclohexane/ethyl acetate gives 4.70 g (98% pure, 47% of theory) of the title compound as a yellow liquid.

log P[a]: 2.64; log P[b]: 2.69; 1H-NMR (D6-DMSO, 400 MHz) δ ppm 7.09 (d, 1H), 6.78 (d, 1H), 6.49-6.46 (m, 1H), 5.37 (broad, 2H), 3.90 (q, 2H); GC-MS: EI mass (m/z): 241 (1Cl) [M]+

The following were obtained analogously:

2-Chloro-5-[(2,2,2-trifluoroethyl)sulphanyl]aniline (IVa-4)

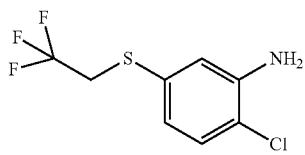

(IVa-4)

log P[a]: 3.00; log P[b]: 2.95; 1H-NMR (D6-DMSO, 400 MHz) δ ppm 7.16 (d, 1H), 6.89 (d, 1H), 6.68-6.65 (m, 1H), 5.48 (broad, 2H), 3.89 (q, 2H); GC-MS: EI mass (m/z): 241 (1Cl) [M]+

2-Fluoro-5-[(2,2,2-trifluoroethyl)sulphanyl]aniline (IVa-5)

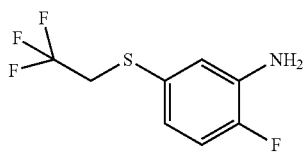

(IVa-5)

log P[a]: 2.57; log P[b]: 2.53; 1H-NMR (D6-DMSO, 400 MHz) δ ppm 7.01-6.97 (m, 1H), 6.92-6.89 (m, 1H), 6.69-6.64 (m, 1H), 5.31 (broad, 2H), 3.82 (q, 2H); GC-MS: EI mass (m/z): 225 [M]+

4-Chloro-2-fluoro-5-[(2,2,2-trifluoroethyl)sulphanyl]aniline (IVa-2)

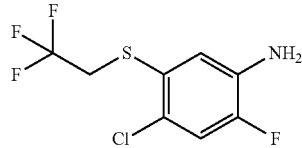

(IVa-2)

11.0 g (30.9 mmol) of N-{4-chloro-2-fluoro-5-[(2,2,2-trifluoroethyl)sulphanyl]phenyl}-2,2,2-trifluoroacetamide in 150 ml of dioxane are added carefully to a solution of 10.3 ml (186 mmol) of sulphuric acid (96% strength) in 100 ml of water. The reaction mixture is then heated under reflux overnight. After cooling, the solution is adjusted to pH 7 using a saturated sodium bicarbonate solution and a little sodium carbonate and extracted three times with ethyl acetate. The combined organic phases are washed with a saturated sodium chloride solution, dried over sodium sulphate, filtered and concentrated. The residue comprises 8.27 g (96% pure, 99% of theory) of the title compound as a black oil/solid mixture.

log P[a]: 3.02; log P[b]: 3.00; 1H-NMR (D6-DMSO, 400 MHz) δ ppm 7.27 (d, 1H), 7.04 (d, 1H), 5.46 (bs, 2H), 3.85 (q, 2H)

N-{4-Chloro-3-[(2,2,2-trifluoroethyl)sulphanyl]phenyl}-2,2,2-trifluoroacetamide (X-3)

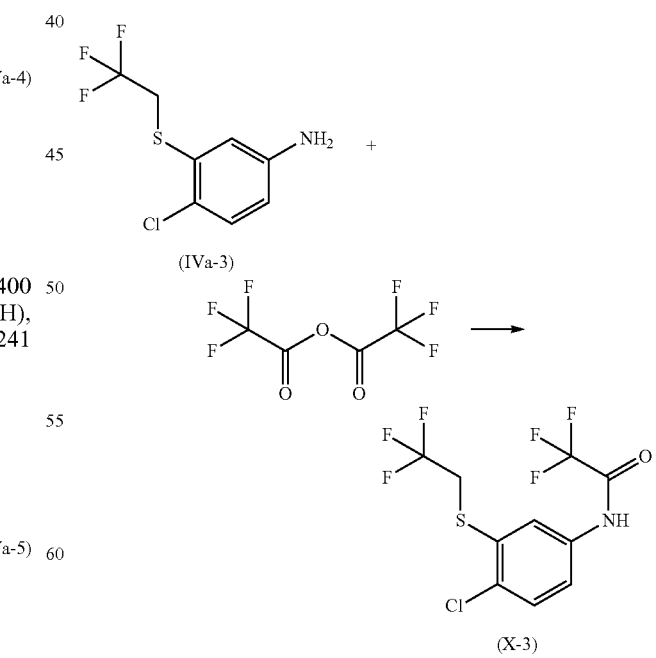

(IVa-3)

(X-3)

1.00 g (4.14 mmol) of 4-chloro-3-[(2,2,2-trifluoroethyl)sulphanyl]aniline is initially charged in 14 ml of dichloromethane, and 0.50 g (4.97 mmol) of triethylamine are added at 0° C. 0.96 g (4.55 mmol) of trifluoroacetic anhydride is added dropwise at 0° C. The reaction mixture is stirred at room temperature overnight, then washed with water and saturated aqueous sodium chloride solution, dried over magnesium sulphate, filtered and freed from the solvent under reduced pressure. Purification by column chromatography on silica gel by means of MPLC using the mobile phase cyclohexane/ethyl acetate gives 1.00 g (99% pure, 71% of theory) of the title compound as a colourless solid.

log P[a]: 3.46; log P[b]: 3.41; 1H-NMR (D6-DMSO, 400 MHz) δ ppm 11.43 (s, 1H), 7.91 (d, 1H), 7.63-7.69 (m, 1H), 7.56-7.58 (m, 1H), 4.05 (q, 2H); 1H-NMR (CDCl$_3$, 400 MHz) δ ppm 7.85 (broad, 1H), 7.82 (d, 1H), 7.52-7.45 (m, 2H), 3.53 (q, 2H); GC-MS: EI mass (m/z): 337 (1Cl) [M]+

Synthesis of Nitro Compounds of the Formula (V)

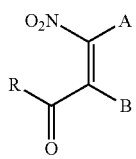

(V)

1-Ethyl-5-nitro-1H-imidazole-4-carboxylic acid (V-1)

Step 1. Methyl 5-nitro-M-imidazole-4-carboxylate

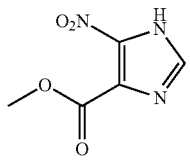

At 100° C., 45.0 g (0.56 mol) of ammonium nitrate are added a little at a time to a solution of 20.0 g (0.18 mol) of 1H-imidazole-4-carboxylic acid in 160 ml of concentrated sulphuric acid. The reaction mixture is stirred at this temperature for two days and, after cooling, 60 ml of methanol are added carefully and with constant stirring. The solution is then stirred at 60° C. for 24 h and, after cooling, poured onto ice. This results in the precipitation of a fine white solid. The suspension is neutralized using a 33% strength solution of ammonia. The solid is filtered off and dried, giving 17.2 g (56% of theory) of the title compound.

1H-NMR (D6-DMSO, 400 MHz) δ ppm: 14.24 (bs, 1H), 7.99 (s, 1H), 3.87 (s, 3H)

Step 2. Methyl 1-ethyl-5-nitro-M-imidazole-4-carboxylate

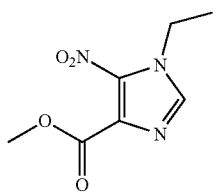

20.1 g (0.13 mol) of diethyl sulphate, 132 ml of an 8% strength aqueous sodium bicarbonate solution and 132 ml of water are added to a solution of 15.0 g (0.09 mol) of methyl 5-nitro-1H-imidazole-4-carboxylate in 420 ml of tetrahydrofuran. The reaction mixture is stirred at room temperature overnight and then extracted with 3×50 ml of ethyl acetate. The combined organic phases are dried over magnesium sulphate and freed of the solvent under reduced pressure. Purification by column chromatography on silica gel using pentane/ethyl acetate (40:1) gives 3.50 g (20% of theory) of the title compound and 12.0 g (69% of theory) of the isomeric methyl 1-ethyl-4-nitro-M-imidazole-5-carboxylate.

Title compound 1H-NMR (MeOD-D4, 400 MHz) δ ppm: 7.99 (s, 1H), 4.36 (q, 2H), 3.91 (s, 3H), 1.48 (t, 3H)

Methyl 1-ethyl-4-nitro-1H-imidazole-5-carboxylate 1H-NMR (CDCl$_3$, 400 MHz) δ ppm: 7.45 (s, 1H), 4.26 (s, 3H), 3.96 (s, 3H), 1.49 (t, 3H)

Step 3. 1-Ethyl-5-nitro-1H-imidazole-4-carboxylic acid (V-1)

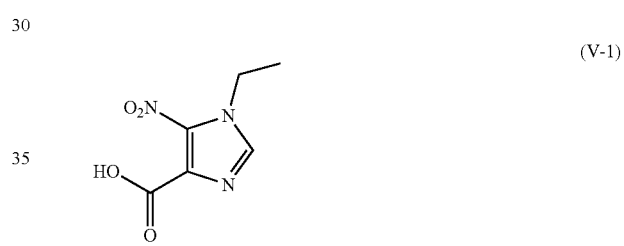

8 ml of a 2.5M aqueous sodium hydroxide solution are added to a solution of 3.50 g (17.6 mmol) of methyl 1-ethyl-5-nitro-1H-imidazole-4-carboxylate in 8 ml of methanol. The reaction mixture is stirred at room temperature for 16 h and then freed of the solvent under reduced pressure. The residue is taken up in a little water and the pH of the solution is adjusted to 5 using 1M HCl. The resulting solid is filtered off and dried under reduced pressure. This gives 2.10 g (66% of theory) of the title compound as a white solid.

1H-NMR (MeOD-D4, 400 MHz) δ ppm: 8.12 (s, 1H), 4.29 (q, 2H), 1.39 (t, 3H)

Synthesis of Bromides of the Formula (VIIa)

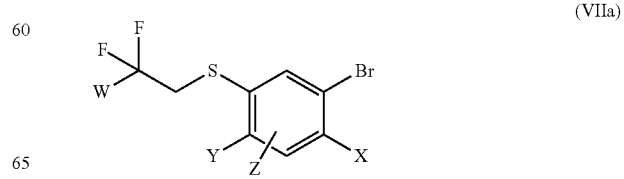

5-Bromo-2-methylphenyl-2,2,2-trifluoroethyl sulphide (VIIa-7)

Step 1: 5-Bromo-2-methylbenzenesulphonyl chloride

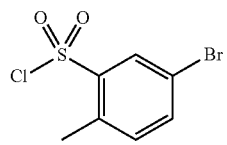

69.50 g (406.3 mmol) of 4-bromotoluene are initially charged in 250 ml of dichloromethane, and 175.33 g (1.50 mol) of chlorosulphonic acid are added dropwise at −5-5° C. With stirring, the reaction mixture is brought to room temperature overnight, 1000 ml of ice-water are added and the mixture is extracted with dichloromethane. The combined organic phases are washed with saturated aqueous sodium chloride solution, dried over magnesium sulphate, filtered and freed from the solvent under reduced pressure. This gives 89.54 g (95% pure, 78% of theory) of the title compound as a yellow liquid which is reacted further without further purification.

log P[a]: 3.73; log P[b]: 3.74; GC-MS: EI mass (m/z): 270 (1Cl, 1Br) [M]$^+$; $^1$H-NMR (CDCl$_3$, 400 MHz): 8.19 (d, 1H), 7.73-7.72 (m, 1H), 7.31 (d, 1H), 2.73 (s, 3H); $^1$H-NMR (CD$_3$CN, 400 MHz): 8.18 (d, 1H), 7.88-7.85 (m, 1H), 7.46 (d, 1H), 2.71 (s, 3H)

Step 2: 4-Bromo-2-[(3-bromo-4-methylphenyl)disulphanyl]-1-methylbenzene

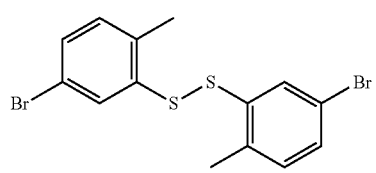 [SMILES: Cc1ccc(Br)cc1SSc1cc(Br)ccc1C]

With vigorous stirring, 145.7 g of aqueous hydroiodic acid (57% strength, 649.2 mmol) are added to 25.00 g (92.7 mmol) of 5-bromo-2-methylbenzenesulphonyl chloride. The reaction mixture is stirred at room temperature for 3 days, and 40% strength aqueous sodium bisulphite solution is then added. The solid is filtered off with suction, washed thoroughly with water and dried on a clay disc overnight. This gives 19.50 g (95% pure, 99% of theory) of the title compound as a yellow solid which is reacted further without further purification.

log P[a]: >7.36; log P[b]: >7.36; GC-MS: EI mass (m/z): 404 (2Br) [M]$^+$

1H-NMR (D6-DMSO): 7.56 (d, 2H), 7.46-7.43 (m, 2H), 7.26 (d, 2H), 2.35 (s, 6H)

Step 3: 5-Bromo-2-methylphenyl-2,2,2-trifluoroethyl sulphide (VIIa-7)

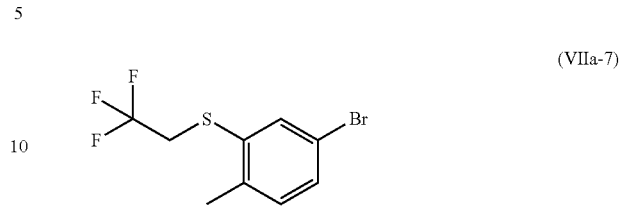

(VIIa-7)

27.70 g (68.5 mmol) of 4-bromo-2-[(3-bromo-4-methylphenyl)disulphanyl]-1-methylbenzene are initially charged in 350 ml of N,N-dimethylformamide, 23.86 g (137.1 mmol) of sodium dithionite, 18.66 g (137.1 mmol) of Rongalit® and 18.94 g (137.1 mmol) of potassium carbonate are added and the mixture is cooled to 0° C. 31.65 g (150.8 mmol) of 1,1,1-trifluoro-2-iodoethane in 20 ml of N,N-dimethylformamide are added dropwise at 0° C. With stirring, the reaction mixture is brought to room temperature overnight, 500 ml of water are added and the mixture is extracted with tert-butyl methyl ether. The combined organic phases are washed with water, saturated aqueous sodium bicarbonate solution and saturated aqueous sodium chloride solution, dried over magnesium sulphate, filtered and freed from the solvent under reduced pressure. Purification by column chromatography on silica gel by means of MPLC using the mobile phase cyclohexane/ethyl acetate gives 30.01 g (93% pure, 71% of theory) of the title compound as a colourless liquid.

log P[a]: 4.29; log P[b]: 4.26; GC-MS: EI mass (m/z): 286 (1Br) [M]$^+$

1H-NMR (D6-DMSO, 400 MHz) δ ppm: 7.70 (d, 1H), 7.39-7.36 (m, 1H), 7.21 (d, 1H), 4.09 (q, 2H), 2.30 (s, 3H)

The following were obtained analogously:

4-Bromo-1-methoxy-2-[(2,2,2-trifluoroethyl)sulphanyl]benzene (VIIa-8)

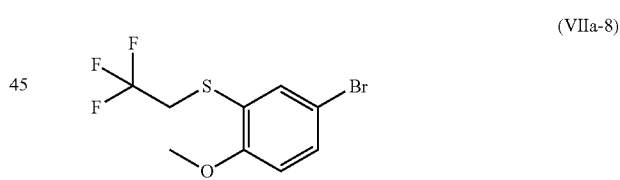

(VIIa-8)

log P[a]: 3.69; log P[b]: 3.81; GC-MS: EI mass (m/z): 302 (1Br) [M]$^+$

1H-NMR (D6-DMSO, 400 MHz) δ ppm: 7.59 (d, 1H), 7.45-7.42 (m, 1H), 7.00 (d, 1H), 4.02 (q, 2H), 3.85 (s, 3H)

4-Bromo-1-chloro-2-[(2,2,2-trifluoroethyl)sulphanyl]benzene (VIIa-3)

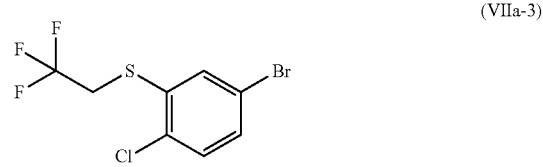

(VIIa-3)

-continued

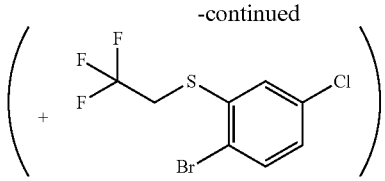

Obtained as a mixture of 60% 4-bromo-1-chloro-2-[(2,2,2-trifluoroethyl)sulphanyl]benzene and 40% 1-bromo-4-chloro-2-[(2,2,2-trifluoroethyl)sulphanyl]benzene.

log P[a]: 4.20; log P[b]: 4.21; GC-MS: EI mass (m/z): 306 (1Br, 1Cl) [M]$^+$

1H-NMR (D6-DMSO, 400 MHz) δ ppm: 7.85 (broad, 1H), 7.70 (d, 1'H), 7.67 (d, 1'H), 7.50-7.44 (m, 2H), 7.27-7.24 (m, 1'H), 4.30-4.22 (m, 2H+2'H)

1-Bromo-2-fluoro-4-methyl-5-[(2,2,2-trifluoroethyl)sulphanyl]benzene (VIIa-1)

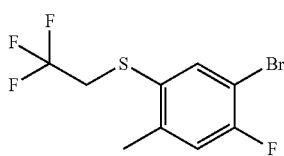

log P[a]: 4.30; log P[b]: 4.34; GC-MS: EI mass (m/z): 304 (1Br) [M]$^+$

1H-NMR (D6-DMSO, 400 MHz): 7.87 (d, 1H), 7.36 (d, 1H), 4.02 (q, 2H), 2.35 (s, 3H)

1-Bromo-2,4-dichloro-5-[(2,2,2-trifluoroethyl)sulphanyl]benzene (VIIa-6)

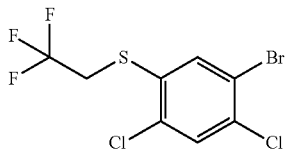

log P[a]: 4.80; log P[b]: 4.77; GC-MS: EI mass (m/z): 340 (1Br, 2Cl) [M]$^+$

1H-NMR (D6-DMSO, 400 MHz): 8.04 (s, 1H), 7.91 (s, 1H), 4.28 (q, 2H)

1-Bromo-2,4-dimethyl-5-[(2,2,2-trifluoroethyl)sulphanyl]benzene (VIIa-11)

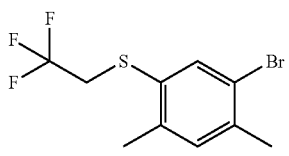

log P[a]: 4.81; log P[b]: 4.77; GC-MS: EI mass (m/z): 340 (1Br, 2Cl) [M]$^+$

1H-NMR (D6-DMSO, 400 MHz): 8.04 (s, 1H), 7.91 (s, 1H), 4.28 (q, 2H)

4-Bromo-2-[(2,2,2-trifluoroethyl)sulphanyl]benzonitrile (VIIa-9)

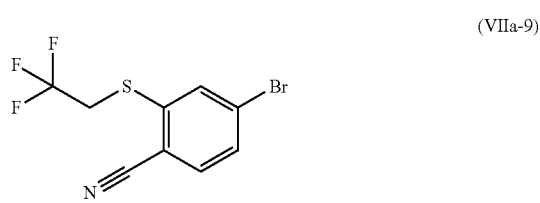 [SMILES: N#Cc1ccc(Br)cc1SCC(F)(F)F]

24.0 g (86.4 mmol) of sodium hydride (60% in mineral oil) are initially charged in 300 ml of N,N-dimethylformamide, and 10.0 g (86.4 mmol) of 2,2,2-trifluoroethanethiol are added dropwise at 0° C. At 0° C., the reaction mixture is added dropwise to a solution of 14.4 g (72.0 mmol) of 4-bromo-2-fluorobenzonitrile in 100 ml of N,N-dimethylformamide, and the mixture is brought to room temperature overnight while stirring. The reaction mixture is poured into water, neutralized with saturated aqueous ammonium chloride solution and extracted with tert-butyl methyl ether. The combined organic phases are washed successively with water and saturated aqueous sodium chloride solution, dried over magnesium sulphate, filtered and freed from the solvent under reduced pressure. The residue is triturated with petroleum ether, filtered off and recrystallized from diethyl ether. This gives 17.6 g (99% pure, 82% of theory) of the title compound as a colourless solid.

log P[a]: 3.21; log P[b]: 3.16; 1H-NMR (D6-DMSO, 400 MHz) δ ppm: 8.12 (d, 1H), 7.83 (d, 1H), 7.72-7.69 (m, 1H), 4.33 (q, 2H)

The following was obtained analogously:

4-Bromo-2-[(2,2,2-trifluoroethyl)sulphanyl]-1-(trifluoromethyl)benzene (VIIa-10)

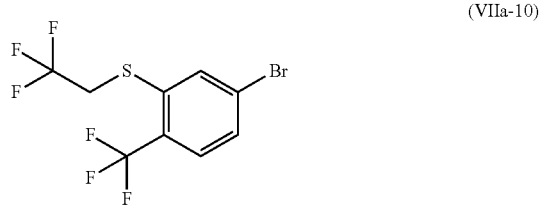 [SMILES: FC(F)(F)CSc1cc(Br)ccc1C(F)(F)F]

log P[a]: 4.22; log P[b]: 4.20; $^1$H-NMR (D6-DMSO, 400 MHz): 8.18 (s, 1H), 7.73-7.68 (m, 2H), 4.30 (q, 2H)

Synthesis of Iodides of the Formula (VIIa)

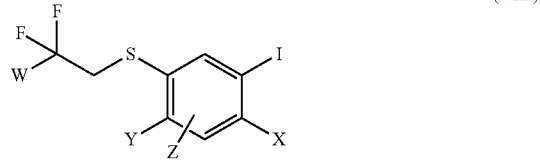

121

1-Fluoro-2-iodo-5-methyl-4-[(2,2,2-trifluoroethyl)sulphanyl]benzene (VIIa-1-I)

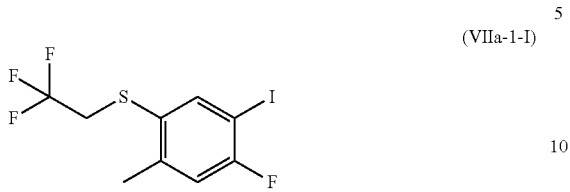
(VIIa-1-I)

10.0 g (33.0 mmol) of 5-bromo-2-methylphenyl-2,2,2-trifluoroethyl sulphide, 9.89 g (66.0 mmol) of sodium iodide, 314 mg (1.65 mmol) of copper(I) iodide and 469 mg (3.3 mmol) of trans-N,N'-dimethylcyclohexane-1,2-diamine (racemic) were stirred in 33 ml of degassed dioxane at 110° C. overnight. Another 9.89 g (66.0 mmol) of sodium iodide, 314 mg (1.65 mmol) of copper(I) iodide and 234 mg (1.65 mmol) of trans-N,N'-dimethylcyclohexane-1,2-diamine (racemic) were added, and the mixture was stirred at 110° C. overnight. Another 9.89 g (66.0 mmol) of sodium iodide and 314 mg (1.65 mmol) of copper(I) iodide and 20 ml of dioxane were added, and the mixture was stirred at 110° C. overnight. After cooling to room temperature, the mixture was diluted with ethyl acetate, filtered through kieselguhr and concentrated. Purification by column chromatography on silica gel by means of MPLC using the mobile phase cyclohexane/ethyl acetate gives 8.77 g (97% pure, 74% of theory) of the title compound as a colourless oil.

log P[a]: 4.44; log P[b]: 4.44; GC-MS: EI mass (m/z): 350 [M]$^+$

1H-NMR (D6-DMSO, 400 MHz): 7.97 (d, 1H), 7.24 (d, 1H), 3.96 (q, 2H), 2.35 (s, 3H)

The following was obtained analogously:

4-Iodo-1-methyl-2-[(2,2,2-trifluoroethyl)sulphanyl]benzene (VIIa-7-I)

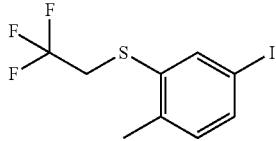
(VIIa-7-I)

log P[a]: 4.49; log P[b]: 4.48; GC-MS: EI mass (m/z): 332 [M]$^+$

1H-NMR (D6-DMSO, 400 MHz): 7.83 (d, 1H), 7.55-7.53 (m, 1H), 7.05 (d, 1H), 4.05 (q, 2H), 2.30 (s, 3H)

Synthesis of Boronic Acids of the Formula (VIII)

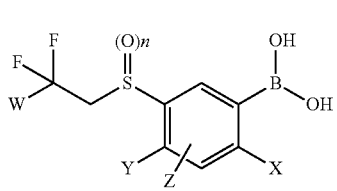
(VIII)

122

{4-Methyl-3-[(2,2,2-trifluoroethyl)sulphanyl]phenyl}boronic acid (VIIIa-7)

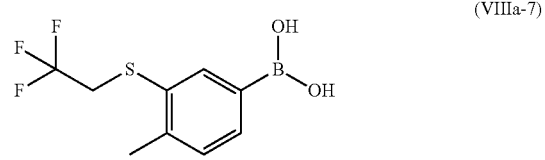 [SMILES: Cc1ccc(B(O)O)cc1SCC(F)(F)F]
(VIIIa-7)

Step 1: 4,4,5,5-Tetramethyl-2-{4-methyl-3-[(2,2,2-trifluoroethyl)sulphanyl]phenyl}-1,3,2-dioxaborolane

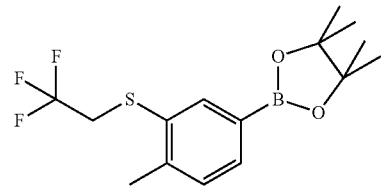 [SMILES: Cc1ccc(B2OC(C)(C)C(C)(C)O2)cc1SCC(F)(F)F]

15.0 g (52.6 mmol) of 5-bromo-2-methylphenyl-2,2,2-trifluoroethyl sulphide, 14.7 g (57.9 mmol) of 4,4,4',4',5,5,5',5'-octamethyl-2,2'-bi-1,2,3-dioxaborolane, 10.3 g (105.2 mmol) of potassium acetate and 2.15 g (2.63 mmol) of 1,1'-bis(diphenylphosphino)ferrocenepalladium(II) dichloride/methylene chloride adduct are initially charged in 78 ml of degassed dry dioxane and stirred at 160° C. under microwave irradiation (Anton Paar Multiwave) for 40 min. Using ethyl acetate, the reaction mixture is filtered through silica gel, and the filtrate is freed from the solvent under reduced pressure. Purification by column chromatography on silica gel by means of MPLC using the mobile phase cyclohexane/ethyl acetate gives 14.07 g (90% pure, 72% of theory) of the title compound as a green oil.

log P[a]: 3.73; log P[b]: 3.74; ESI mass (m/z): 333 [M+1]$^+$; GC-MS: EI mass (m/z): 332 [M]$^+$ 1H-NMR (D6-DMSO, 400 MHz) δ ppm: 7.77 (s, 1H), 7.52 (d, 1H), 7.30 (d, 1H), 3.87 (q, 2H), 2.42 (s, 3H), 1.29 (s, 12H)

Step 2: {4-Methyl-3-[(2,2,2-trifluoroethyl)sulphanyl]phenyl}boronic acid (VIIIa-7) and {4-methyl-3-[(2,2,2-trifluoroethyl)sulphinyl]phenyl}boronic acid (VIIIb-7)

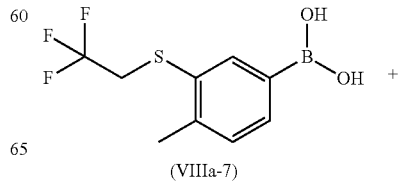
(VIIIa-7)
+

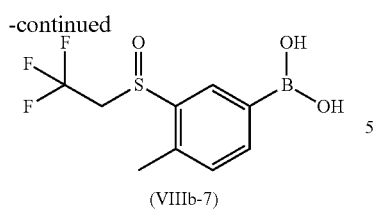

(VIIIb-7)

730 mg (2.2 mmol) of 4,4,5,5-tetramethyl-2-{4-methyl-3-[(2,2,2-trifluoroethyl)sulphanyl]phenyl}-1,3,2-dioxaborolane are initially charged in 20 ml of acetone and 20 ml of water, and 381 mg (4.9 mmol) of ammonium acetate and 1.06 g (4.9 mmol) of sodium periodate are added at 0° C. The reaction mixture is stirred at room temperature overnight and then freed from the acetone under reduced pressure. The acidic aqueous phase is extracted with ethyl acetate, and the combined organic phases are washed successively with water and saturated aqueous sodium chloride solution, dried over magnesium sulphate, filtered and freed from the solvent under reduced pressure. Purification by column chromatography on silica gel by means of MPLC using the mobile phase cyclohexane/ethyl acetate gives 105 mg (96% pure, 18% of theory) of {4-methyl-3-[(2,2,2-trifluoroethyl)sulphanyl]phenyl}boronic acid and 138 mg (97% pure, 23% of theory) of {4-methyl-3-[(2,2,2-trifluoroethyl)sulphinyl]phenyl}boronic acid as colourless solids.

{4-Methyl-3-[(2,2,2-trifluoroethyl)sulphanyl]phenyl}boronic acid (VIIIa-7)

log P[a]: 2.30; log P[b]: 2.24; ESI mass (m/z): pos. [a]: 251 [M+1]+, neg. [b]: 249 [M−1]−

$^1$H-NMR (D6-DMSO, 400 MHz): 8.08 (s, 2H), 7.92 (s, 1H), 7.61-7.59 (m, 1H), 7.23 (d, 1H), 3.90 (q, 2H), 2.38 (s, 3H)

{4-Methyl-3-[(2,2,2-trifluoroethyl)sulphinyl]phenyl}boronic acid (VIIIb-7)

log P[a]: 1.41; log P[b]: 1.36; ESI mass (m/z): pos. [a]: 267 [M+1]+; GC-MS: decomposition $^1$H-NMR (D6-DMSO, 400 MHz): 8.31 (s, 1H), 8.24 (s, 2H), 7.89-7.87 (m, 1H), 7.31 (d, 1H), 4.12-4.02 (m, 1H), 3.94-3.82 (m, 1H), 2.39 (s, 3H)

The following were obtained analogously:

{2-Fluoro-4-methyl-5-[(2,2,2-trifluoroethyl)sulphanyl]phenyl}boronic acid (VIIIa-1)

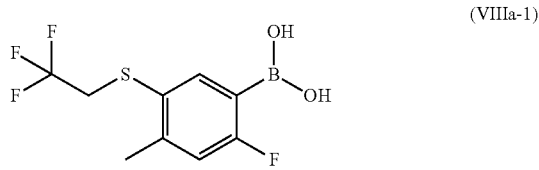 [SMILES: Cc1cc(F)c(B(O)O)cc1SCC(F)(F)F]

(VIIIa-1)

log P[a]: 2.34; log P[b]: 2.41; ESI mass (m/z): pos. [a]: 269 [M+1]+, neg. [a]: 313 [M+HCOO−]−, neg. [b]: 267 [M−1]−

$^1$H-NMR (D6-DMSO, 400 MHz): 8.21 (s, 2H), 7.74 (d, 1H), 7.06 (d, 1H), 3.82 (q, 2H), 2.40 (s, 3H)

{2-Fluoro-4-methyl-5-[(2,2,2-trifluoroethyl)sulphinyl]phenyl}boronic acid (VIIIb-1)

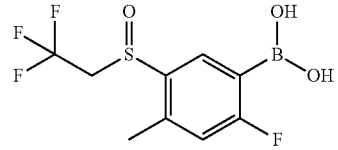

(VIIIb-1)

log P[a]: 1.38; log P[b]: 1.11; ESI mass (m/z): pos. [a]: 285 [M+1]+, neg. [a]: 329 [M+HCOO−]−

$^1$H-NMR (D6-DMSO, 400 MHz): 8.36 (s, 2H), 8.08 (d, 1H), 7.15 (d, 1H), 4.14-3.92 (m, 2H), 2.39 (s, 3H)

Preparation Example 1

5-{2-Fluoro-4-methyl-5-[(2,2,2-trifluoroethyl)sulphanyl]phenyl}-1-methyl-1,5-dihydro-4H-pyrazolo[3,4-d]pyrimidin-4-one (2)

1.1. N-{2-Fluoro-4-methyl-5-[(2,2,2-trifluoroethyl)sulphanyl]phenyl}-1-methyl-5-nitro-1H-pyrazole-4-carboxamide (according to Process A)

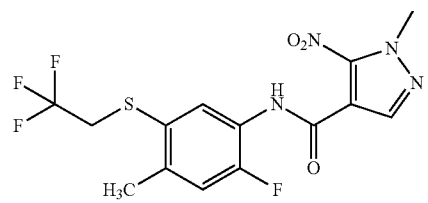 [SMILES: Cc1cc(F)c(NC(=O)c2cnn(C)c2[N+](=O)[O-])cc1SCC(F)(F)F]

A little at a time, 150 mg (0.63 mmol) of 2-fluoro-4-methyl-5-[(2,2,2-trifluoroethyl)sulphanyl]aniline are added to a solution of 1-methyl-5-nitro-1H-pyrazole-4-carbonyl chloride [prepared from 100 mg (0.58 mmol) of 1-methyl-5-nitro-1H-pyrazole-4-carboxylic acid and 0.13 ml (1.75 mmol) of thionyl chloride in toluene] and 0.28 ml (2.51 mmol) of N-methylmorpholine in 3 ml of dichloroethane. The reaction mixture is stirred at 40° C. overnight and, after cooling to room temperature, diluted with dichloromethane, and water is added. The organic phase is separated off, dried over sodium sulphate, filtered and applied to RP(C-18) material. Purification by column chromatography by means of MPLC on RP(C-18) using water/acetonitrile gives 139 mg (100% pure, 60% of theory) of the title compound.

log P[a]: 3.22; log P[b]: 3.16; 1H-NMR (D6-DMSO, 400 MHz) δ ppm: 10.33 (s, 1H), 8.06 (d, 1H), 7.98 (s, 1H), 7.30 (d, 1H), 4.14 (s, 3H), 3.83 (q, 2H), 2.41 (s, 3H)

1.2. 5-Amino-N-{2-fluoro-4-methyl-5-[(2,2,2-trifluoroethyl)sulphanyl]phenyl}-1-methyl-1H-pyrazole-4-carboxamide

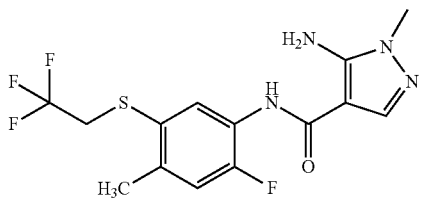

139 mg (0.35 mmol) of N-{2-fluoro-4-methyl-5-[(2,2,2-trifluoroethyl)sulphanyl]phenyl}-1-methyl-5-nitro-M-pyrazole-4-carboxamide are initially charged in 4.5 ml of a mixture of tetrahydrofuran and glacial acetic acid 2:1 and cooled to 0° in an ice bath. 0.1 ml of 33% strength aqueous hydrochloric acid solution are then added dropwise, followed by 232 mg (3.54 mmol), a little at a time. The reaction mixture is stirred at room temperature for about 2 h and the pH is then carefully adjusted to 8 using a saturated aqueous sodium bicarbonate solution. The combined organic phases are extracted with ethyl acetate and then dried over magnesium sulphate, filtered and freed from the solvent under reduced pressure. The residue comprises 58 mg (100% pure, 45% of theory) of the title compound.

log P[a]: 2.44; log P[b]: 2.23; 1H-NMR (D6-DMSO, 400 MHz) δ ppm: 9.29 (bs, 1H), 7.79 (d, 1H), 7.23 (d, 1H), 6.28 (bs, 2H), 3.83 (q, 2H), 3.54 (s, 3H), 2.39 (s, 3H)

Alternative preparation according to Process B: 540 g (2.26 mmol) of 2-fluoro-4-methyl-5-[(2,2,2-trifluoroethyl)sulphanyl]aniline are initially charged in dry dichloromethane. The flask is flushed with argon, and 2.5 ml of a 2M solution of trimethylaluminium in toluene are added dropwise. The reaction mixture is stirred at room temperature for 30 min, and 405 mg (2.39 mmol) of ethyl 5-amino-1-methyl-1H-pyrazole-4-carboxylate are then added. The mixture is stirred at room temperature overnight, and a 10% strength potassium/sodium tartrate solution is then added. The organic phase is separated off and the aqueous phase is extracted twice with dichloromethane. The combined organic phases are dried over sodium sulphate and the mixture is applied to RP(C-18) material. Removal of the solvents is followed by purification by means of MPLC on an RP(C-18) column using water/acetonitrile. This gives 577 mg (100% pure, 71% of theory) of the title compound.

1.3. 5-{2-Fluoro-4-methyl-5-[(2,2,2-trifluoroethyl)sulphanyl]phenyl}-1-methyl-1,5-dihydro-4H-pyrazolo[3,4-d]pyrimidin-4-one (1)

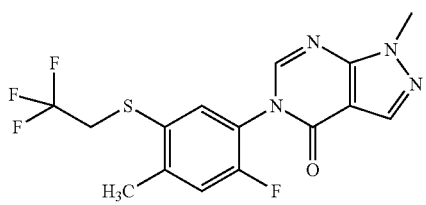

0.07 ml of concentrated sulphuric acid is added to 56 mg (0.16 mmol) of 5-amino-N-{2-fluoro-4-methyl-5-[(2,2,2-trifluoroethyl)sulphanyl]phenyl}-1-methyl-1H-pyrazole-4-carboxamide and 3.5 ml (21 mmol) of triethyl orthoformate, and the mixture is stirred at a temperature of 140° C. for 3 h. The reaction mixture is cooled to room temperature and diluted with ethyl acetate. The mixture is then poured into water and extracted twice with ethyl acetate. The organic phase is washed with water, dried over sodium sulphate, filtered and freed from the solvent under reduced pressure. The residue comprises 54 mg (96% pure, 90% of theory) of the title compound.

log P[a]: 2.66; log P[b]: 2.65; 1H-NMR (D6-DMSO, 400 MHz) δ ppm: 8.41 (s, 1H), 8.18 (s, 1H), 7.83 (d, 1H), 7.45 (d, 1H), 4.05-3.98 (m, 5H), 2.45 (s, 3H)

Preparation Example 2

5-{2-Fluoro-4-methyl-5-[(2,2,2-trifluoroethyl)sulphinyl]phenyl}-1-methyl-1,5-dihydro-4H-pyrazolo[3,4-d]pyrimidin-4-one (2)

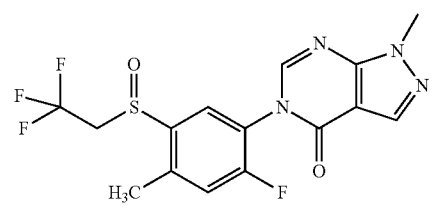

At 0-4° C., 18 mg (70% pure, 0.07 mmol) of meta-chloroperbenzoic acid are added to a solution of 25 mg (0.07 mmol) of 5-{2-fluoro-4-methyl-5-[(2,2,2-trifluoroethyl)sulphanyl]phenyl}-1-methyl-1,5-dihydro-4H-pyrazolo[3,4-d]pyrimidin-4-one in 2 ml of dichloromethane, and the reaction mixture is stirred at RT for 2 h. A 33% strength aqueous bisulphite solution is added, and the mixture is then extracted twice with ethyl acetate. The combined organic phases are washed with water, dried over sodium sulphate and filtered. Removal of the solvent under reduced pressure gives 20 mg (100% pure, 77% of theory) of the sulphoxide.

log P[a]: 1.73; log P[b]: 1.69; 1H-NMR (D6-DMSO, 400 MHz) δ ppm: 8.47 (s, 1H), 8.20 (s, 1H), 8.07 (d, 1H), 7.58 (d, 1H), 4.40-4.00 (broad, 2H), 3.98 (s, 3H), 2.48 (s, 3H)

Preparation Example 3

5-{2-Fluoro-4-methyl-5-[(2,2,2-trifluoroethyl)sulphanyl]phenyl}-1-methyl-6-(trifluoromethyl)-1,5-dihydro-4H-pyrazolo[3,4-d]pyrimidin-4-one (13)

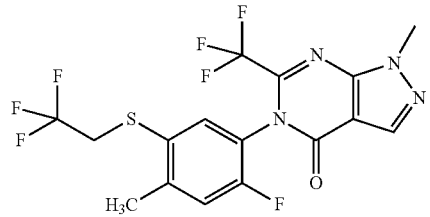

0.60 g (1.66 mmol) of 5-amino-N-{2-fluoro-4-methyl-5-[(2,2,2-trifluoroethyl)sulphanyl]phenyl}-1-methyl-1H-pyrazole-4-carboxamide and 2.08 ml (14.9 mmol) are initially charged in 5 ml of acetonitrile. At 0° C., 0.94 ml (6.62 mmol) of trifluoroacetic anhydride are added slowly, and the mixture is stirred at 0° C. for 1 h. The mixture is then stirred at 90° C. for 12 h. After cooling, a saturated sodium bicarbonate solution is added, and the reaction mixture is extracted twice with ethyl acetate. The organic phase is washed with a saturated sodium chloride solution, dried over sodium sulphate, filtered and concentrated. To remove the trifluoroacetic acid completely, the residue is dissolved in ethyl acetate and washed with dilute aqueous sodium hydroxide solution. The organic phase is dried over sodium sulphate, filtered and concentrated. The residue is applied to RP(C-18) material and purified by means of MPLC on an RP(C-18) column using water/acetonitrile. 370 mg (95% pure, 48% of theory) of the title compound are isolated.

log P[a]: 3.75; log P[b]: 3.94; 1H-NMR (D6-DMSO, 400 MHz) δ ppm: 8.35 (s, 1H), 7.93 (d, 1H), 7.49 (d, 1H), 4.05 (s, 3H), 3.89 (q, 2H), 2.47 (s, 3H)

Preparation Example 4

5-{2-Fluoro-4-methyl-5-[(2,2,2-trifluoroethyl)sulphinyl]phenyl}-1-methyl-6-(trifluoromethyl)-1,5-dihydro-4H-pyrazolo[3,4-d]pyrimidin-4-one (16)

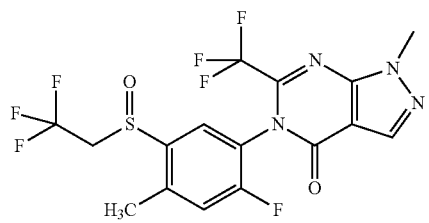

At 0-4° C., 200 mg (70% pure, 0.8 mmol) of meta-chloroperbenzoic acid are added to a solution of 340 mg (0.77 mmol) of 5-{2-fluoro-4-methyl-5-[(2,2,2-trifluoroethyl)sulphanyl]phenyl}-1-methyl-6-(trifluoromethyl)-1,5-dihydro-4H-pyrazolo[3,4-d]pyrimidin-4-one in 5 ml of dichloromethane, and the reaction mixture is stirred at RT for 2 h. A 33% strength aqueous bisulphite solution is added, and the mixture is then extracted twice with dichloromethane. The combined organic phases are washed with a saturated sodium bicarbonate solution, dried over sodium sulphate and filtered. Removal of the solvent under reduced pressure gives 303 mg (99% pure, 85% of theory) of the title compound as a mixture of two rotamers.

log P[a]: 2.67 and 2.74; log P[b]: 2.63 and 2.70; 1H-NMR (D6-DMSO, 400 MHz) δ ppm: 8.35-8.34 (m, 1H), 8.23-8.18 (2×d, 1H), 7.62 (d, 1H), 4.38-4.32 (m, 1H), 4.05-4.04 (m, 3H), 3.92-3.78 (m, 1H), 3H under the DMSO peak Preparation Example 5

5-{2-Fluoro-4-methyl-5-[(2,2,2-trifluoroethyl)sulphanyl]phenyl}-1,6-dimethyl-1,5-dihydro-4H-pyrazolo[3,4-d]pyrimidin-4-one (14)

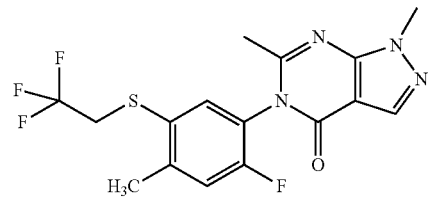 [SMILES: Cc1cc(F)c(-n2c(C)nc3c(cnn3C)c2=O)cc1SCC(F)(F)F]

0.05 ml of concentrated sulphuric acid is added to 600 mg (1.66 mmol) of 5-amino-N-{2-fluoro-4-methyl-5-[(2,2,2-trifluoroethyl)sulphanyl]phenyl}-1-methyl-1H-pyrazole-4-carboxamide and 5.0 ml (27.2 mmol) of triethyl orthoacetate, and the mixture is stirred at a temperature of 140° C. for 3 h. The reaction mixture is cooled to room temperature and diluted with ethyl acetate. The mixture is then poured into water and extracted twice with ethyl acetate. The organic phase is washed with water, dried over sodium sulphate, filtered, applied to RP(C-18) material and freed from the solvent under reduced pressure. Purification by column chromatography by means of MPLC on RP(C-18) using water/acetonitrile gives 217 mg (94% pure, 32% of theory) of the title compound.

log P[a]: 2.84; log P[b]: 2.79; 1H-NMR (D6-DMSO, 400 MHz) δ ppm: 8.11 (s, 1H), 7.81 (d, 1H), 7.47 (d, 1H), 4.07-3.92 (m, 5H), 2.45 (s, 3H), 2.20 (s, 3H)

Preparation Example 6

5-{2-Fluoro-4-methyl-5-[(2,2,2-trifluoroethyl)sulphinyl]phenyl}-1,6-dimethyl-1,5-dihydro-4H-pyrazolo[3,4-d]pyrimidin-4-one (15)

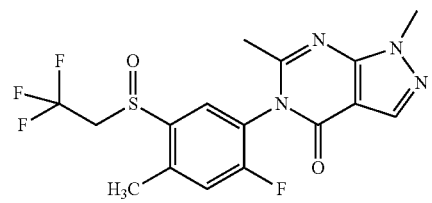 [SMILES: Cc1cc(F)c(-n2c(C)nc3c(cnn3C)c2=O)cc1S(=O)CC(F)(F)F]

At 0-4° C., 134 mg (70% pure, 0.54 mmol) of meta-chloroperbenzoic acid are added to a solution of 200 mg (0.52 mmol) of 5-{2-fluoro-4-methyl-5-[(2,2,2-trifluoroethyl)sulphanyl]phenyl}-1,6-dimethyl-1,5-dihydro-4H-pyrazolo[3,4-d]pyrimidin-4-one in 2 ml of dichloromethane, and the reaction mixture is stirred at RT for 2 h. A 33% strength aqueous bisulphite solution is added, and the mixture is then extracted twice with dichloromethane. The combined organic phases are washed with a saturated sodium bicarbonate solution, dried over sodium sulphate and filtered. Removal of the solvent under reduced pressure gives 203 mg (84% pure, 82% of theory) of the title compound.

log P[a]: 1.85; log P[b]: 1.84; 1H-NMR (D6-DMSO, 400 MHz) δ ppm: 8.12-8.11 (m, 1H), 8.05 (d, 1H), 7.60 (dd, 1H), 4.38-4.20 (m, 2H), 3.96-3.94 (m, 3H), 3H under the DMSO peak, 2.27 (s) and 2.21 (s)(3H)

Preparation Example 7

3-{4-Methyl-3-[(2,2,2-trifluoroethyl)sulphanyl]phenyl}thieno[2,3-d]pyrimidin-4(3H)-one (83)

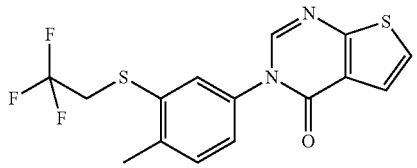 [SMILES: Cc1ccc(-n2cnc3sccc3c2=O)cc1SCC(F)(F)F]

Preparation according to Process D: 427.7 mg (1.5 mmol) of 5-bromo-2-methylphenyl-2,2,2-trifluoroethyl sulphide, 342.4 mg (2.25 mmol) of thieno[2,3-d]pyrimidin-4(3H)-one, 57.1 mg (0.30 mmol) of copper(I) iodide, 85.3 mg (0.60 mmol) of trans-N,N'-dimethylcyclohexane-1,2-diamine (racemic), 74.7 mg (0.45 mmol) of potassium iodide and 621.9 mg (4.50 mmol) of potassium carbonate are stirred in 6 ml of degassed dry dioxane at 110° C. overnight. After cooling to room temperature, the reaction mixture is diluted with ethyl acetate and filtered through silica gel using ethyl acetate. Purification by column chromatography on silica gel by means of MPLC using the mobile phase cyclohexane/ethyl acetate gives 37 mg (99% pure, 7% of theory) of the title compound as a beige solid.

Preparation according to Process E: 100 mg (0.40 mmol) of {4-methyl-3-[(2,2,2-trifluoroethyl)sulphanyl]phenyl}boronic acid, 61 mg (0.40 mmol) of thieno[2,3-d]pyrimidin-4(3H)-one, 109 mg (0.60 mmol) of copper(II) acetate, 63 mg (0.80 mmol) of pyridine and 0.75 g of activated 3 Å molecular sieve are stirred in 6 ml of dioxane at 80° C. overnight. After cooling to room temperature, the reaction mixture is diluted with ethyl acetate and filtered through kieselguhr using ethyl acetate. Purification by column chromatography on silica gel by means of MPLC using the mobile phase cyclohexane/ethyl acetate gives 60 mg (98% pure, 41% of theory) of the title compound as a colourless solid.

log P[a]: 3.04; log P[b]: 3.02; 1H-NMR (D6-DMSO, 400 MHz) δ ppm: 8.37 (s, 1H), 7.71-7.68 (m, 2H), 7.48 (d, 1H), 7.43 (d, 1H), 7.36-7.33 (m, 1H), 4.07 (q, 2H), 2.41 (s, 3H)

Preparation Example 8

3-{4-Methyl-3-[(2,2,2-trifluoroethyl)sulphinyl]phenyl}thieno[2,3-d]pyrimidin-4(3H)-one (86)

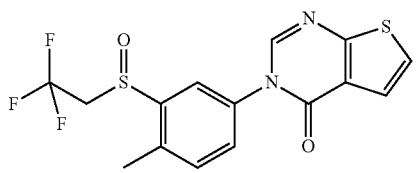 [SMILES: Cc1ccc(-n2cnc3sccc3c2=O)cc1S(=O)CC(F)(F)F]

At 0° C., 7.4 mg (0.043 mmol) of meta-chloroperbenzoic acid are added to a solution of 13.8 mg (0.039 mmol) of 3-{4-methyl-3-[(2,2,2-trifluoroethyl)sulphanyl]phenyl}thieno[2,3-d]pyrimidin-4(3H)-one in 1 ml of dichloromethane. After 4 h at 0° C., another 3.3 mg (0.019 mmol) of meta-chloroperbenzoic acid are added, and the mixture is stirred at room temperature overnight. The reaction mixture is washed successively with 40% strength aqueous sodium bisulphite solution and saturated aqueous sodium bicarbonate solution, dried over magnesium sulphate, filtered and freed from the solvent under reduced pressure. Purification by column chromatography on silica gel by means of MPLC using the mobile phase cyclohexane/ethyl acetate gives 8.6 mg (90% pure, 54% of theory) of the title compound.

log P[a]: 1.94; log P[b]: 1.93; 1H-NMR (D6-DMSO, 400 MHz) δ ppm: 8.46 (s, 1H), 7.97 (d, 1H), 7.71-7.69 (m, 2H), 7.55 (d, 1H), 7.48 (d, 1H), 4.26-4.16 (m, 1H), 4.11-4.02 (m, 1H), 2.46 (s, 3H)

Preparation Example 9

3-{2-Fluoro-4-methyl-5-[(2,2,2-trifluoroethyl)sulphanyl]phenyl}-7-methyl-3,7-dihydro-4H-pyrazolo[3,4-d][1,2,3]triazin-4-one (119)

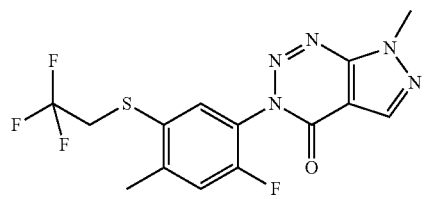 [SMILES: Cc1cc(F)c(-n2nnc3c(cnn3C)c2=O)cc1SCC(F)(F)F]

250 mg (0.69 mmol) of 5-amino-N-{2-fluoro-4-methyl-5-[(2,2,2-trifluoroethyl)sulphanyl]phenyl}-1-methyl-1H-pyrazole-4-carboxamide are initially charged in 5 ml of water and 5 ml of concentrated hydrochloric acid. 405 mg (5.86 mmol) of sodium nitrite dissolved in 5 ml of water are added dropwise. The mixture is stirred at 70° C. overnight. After cooling, the reaction mixture is diluted with dichloromethane, and concentrated sodium bicarbonate solution is added carefully. The organic phase is separated off and the aqueous phase is once more extracted with dichloromethane. The combined organic phases are dried over sodium sulphate, filtered, concentrated and applied to RP(C-18) material. Purification by column chromatography by means of MPLC on RP(C-18) using water/acetonitrile gives 99 mg (100% pure, 38% of theory) of the title compound.

log P[a]: 3.16; log P[b]: 3.13; 1H-NMR (D6-DMSO, 400 MHz) δ ppm: 8.50 (s, 1H), 7.90 (d, 1H), 7.51 (d, 1H), 4.25 (s, 3H), 3.97 (q, 2H), 3H under the DMSO peak Preparation Example 10

3-{2-Fluoro-4-methyl-5-[(2,2,2-trifluoroethyl)sulphinyl]phenyl}-7-methyl-3,7-dihydro-4H-pyrazolo[3,4-d][1,2,3]triazin-4-one (120)

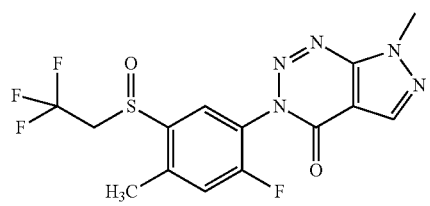 [SMILES: Cc1cc(F)c(-n2nnc3c(cnn3C)c2=O)cc1S(=O)CC(F)(F)F]

At 0-4° C., 55 mg (70% pure, 0.22 mmol) of meta-chloroperbenzoic acid are added to a solution of 80 mg (0.21 mmol) of 3-{2-fluoro-4-methyl-5-[(2,2,2-trifluoroethyl)sulphanyl]phenyl}-7-methyl-3,7-dihydro-4H-pyrazolo[3,4-d][1,2,3]triazin-4-one in 5 ml of dichloromethane, and the reaction mixture is stirred at RT for 2 h. A 33% strength aqueous bisulphite solution is added, and the mixture is then extracted twice with dichloromethane. The combined organic phases are washed with a saturated sodium bicarbonate solution, dried over sodium sulphate and filtered. Removal of the solvent under reduced pressure gives 65 mg (93% pure, 72% of theory) of the title compound.

log P[a]: 2.14; log P[b]: 2.10; 1H-NMR (D6-DMSO, 400 MHz) δ ppm: 8.50 (s, 1H), 8.16 (d, 1H), 7.63 (d, 1H), 4.36-4.25 (m, 4H), 4.07-4.01 (m, 1H), 3H under the DMSO peak The following compounds of the general formula (I) were prepared according to the processes described above:

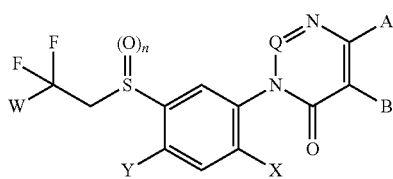

where Z=H according to the above general definition of the compounds of the general formula (I)

| Compound | W | n | Y | X | Q | A—B | R¹ | R² | R³ |
|---|---|---|---|---|---|---|---|---|---|
| 1 | F | 0 | CH₃ | F | C—H | I-1 | CH₃ | H | — |
| 2 | F | 1 | CH₃ | F | C—H | I-1 | CH₃ | H | — |
| 3 | F | 0 | Cl | Cl | C—H | I-1 | CH₃ | H | — |
| 4 | F | 1 | Cl | Cl | C—H | I-1 | CH₃ | H | — |
| 5 | F | 0 | Cl | Cl | C—CH₃ | I-1 | CH₃ | H | — |
| 6 | F | 0 | CH₃ | CH₃ | C—CH₃ | I-1 | CH₃ | H | — |
| 7 | F | 0. | CH₃ | CH₃ | C—H | I-1 | CH₃ | H | — |
| 8 | F | 0 | CH₃ | H | C—H | I-1 | CH₃ | H | — |
| 9 | F | 1 | CH₃ | CH₃ | C—H | I-1 | CH₃ | H | — |
| 10 | F | 1 | CH₃ | CH₃ | C—CH₃ | I-1 | CH₃ | H | — |
| 11 | F | 0 | CH₃ | CH₃ | C—CF₃ | I-1 | CH₃ | H | — |
| 12 | F | 1 | CH₃ | CH₃ | C—CF₃ | I-1 | CH₃ | H | — |
| 13 | F | 0 | CH₃ | F | C—CF₃ | I-1 | CH₃ | H | — |
| 14 | F | 0 | CH₃ | F | C—CH₃ | I-1 | CH₃ | H | — |
| 15 | F | 1 | CH₃ | F | C—CH₃ | I-1 | CH₃ | H | — |
| 16 | F | 1 | CH₃ | F | C—CF₃ | I-1 | CH₃ | H | — |
| 17 | F | 0 | CH₃ | F | C—H | I-1 | CH₂CF₃ | H | — |
| 18 | F | 1 | CH₃ | F | C—H | I-1 | CH₂CF₃ | H | — |
| 19 | F | 0 | CH₃ | F | C—CF₃ | I-1 | CH₂CF₃ | H | — |
| 20 | F | 0 | CH₃ | F | C—CH₃ | I-1 | CH₂CF₃ | H | — |
| 21 | F | 1 | CH₃ | F | C—CF₃ | I-1 | CH₂CF₃ | H | — |
| 22 | F | 1 | CH₃ | F | C—CH₃ | I-1 | CH₂CF₃ | H | — |
| 23 | F | 0 | Cl | H | C—H | I-1 | CH₃ | H | — |
| 24 | F | 0 | CN | H | C—H | I-1 | CH₃ | H | — |
| 25 | F | 0 | CF₃ | H | C—H | I-1 | CH₃ | H | — |
| 26 | F | 1 | CN | H | C—H | I-1 | CH₃ | H | — |
| 27 | F | 1 | CH₃ | H | C—H | I-1 | CH₃ | H | — |
| 28 | F | 1 | Cl | H | C—H | I-1 | CH₃ | H | — |
| 29 | F | 1 | CF₃ | H | C—H | I-1 | CH₃ | H | — |
| 30 | F | 0 | CH₃ | H | C—H | I-1 | CH₃ | CH₃ | — |
| 31 | F | 0 | CF₃ | H | C—H | I-1 | CH₃ | CH₃ | — |
| 32 | F | 1 | CF₃ | H | C—H | I-1 | CH₃ | CH₃ | — |
| 33 | F | 1 | CH₃ | H | C—H | I-1 | CH₃ | CH₃ | — |
| 34 | F | 0 | CN | H | C—H | I-1 | CH₃ | CH₃ | — |
| 35 | F | 1 | CN | H | C—H | I-1 | CH₃ | CH₃ | — |
| 36 | F | 0 | Cl | H | C—H | I-1 | CH₃ | CH₃ | — |
| 37 | F | 1 | Cl | H | C—H | I-1 | CH₃ | CH₃ | — |
| 38 | F | 0 | CH₃ | F | C—H | I-2 | CH₃ | H | — |
| 39 | F | 0 | CH₃ | F | C—CH₃ | I-2 | CH₃ | H | — |
| 40 | F | 1 | CH₃ | F | C—H | I-2 | CH₃ | H | — |
| 41 | F | 1 | CH₃ | F | C—CH₃ | I-2 | CH₃ | H | — |
| 42 | F | 0 | CH₃ | F | C—CF₃ | I-3 | CH₃ | H | — |
| 43 | F | 1 | CH₃ | F | C—CF₃ | I-3 | CH₃ | H | — |
| 44 | F | 0 | CH₃ | H | C—H | I-3 | CH₃ | CH₃ | — |
| 45 | F | 0 | CF₃ | H | C—H | I-3 | CH₃ | CH₃ | — |
| 46 | F | 1 | CF₃ | H | C—H | I-3 | CH₃ | CH₃ | — |
| 47 | F | 1 | CH₃ | H | C—H | I-3 | CH₃ | CH₃ | — |
| 48 | F | 0 | Cl | H | C—H | I-3 | CH₃ | CH₃ | — |
| 49 | F | 1 | Cl | H | C—H | I-3 | CH₃ | CH₃ | — |
| 50 | F | 0 | CN | H | C—H | I-3 | CH₃ | CH₃ | — |
| 51 | F | 1 | CN | H | C—H | I-3 | CH₃ | CH₃ | — |
| 52 | F | 0 | CH₃ | F | C—H | I-9 | CH₃ | H | — |
| 53 | F | 0 | CH₃ | F | C—H | I-9 | CH₂CH₃ | H | — |
| 54 | F | 1 | CH₃ | F | C—H | I-9 | CH₂CH₃ | H | — |
| 55 | F | 0 | CH₃ | CH₃ | C—H | I-9 | CH₃ | H | — |
| 56 | F | 0 | CH₃ | CH₃ | C—CH₃ | I-9 | CH₃ | H | — |
| 57 | F | 0 | Cl | F | C—H | I-9 | CH₃ | H | — |
| 58 | F | 1 | CH₃ | CH₃ | C—H | I-9 | CH₃ | H | — |
| 59 | F | 1 | CH₃ | CH₃ | C—CH₃ | I-9 | CH₃ | H | — |
| 60 | F | 0 | CH₃ | F | C—H | I-12 | — | H | — |
| 61 | F | 1 | CH₃ | F | C—H | I-12 | — | H | — |
| 62 | F | 0 | CH₃ | CH₃ | C—H | I-12 | — | H | — |
| 63 | F | 0 | Cl | Cl | C—H | I-12 | — | H | — |
| 64 | F | 0 | CH₃ | F | C—CH₃ | I-12 | — | H | — |
| 65 | F | 0 | CH₃ | F | C—CF₃ | I-12 | — | H | — |
| 66 | F | 1 | CH₃ | CH₃ | C—H | I-12 | — | H | — |
| 67 | F | 1 | Cl | Cl | C—H | I-12 | — | H | — |
| 68 | F | 1 | CH₃ | F | C—CH₃ | I-12 | — | H | — |
| 69 | F | 1 | CH₃ | F | C—CF₃ | I-12 | — | H | — |
| 70 | F | 0 | CH₃ | F | C—H | I-12 | — | CH₃ | — |
| 71 | F | 0 | Cl | Cl | C—H | I-12 | — | CH₃ | — |
| 72 | F | 0 | CH₃ | CH₃ | C—H | I-12 | — | CH₃ | — |
| 73 | F | 1 | CH₃ | F | C—H | I-12 | — | CH₃ | — |
| 74 | F | 1 | Cl | Cl | C—H | I-12 | — | CH₃ | — |
| 75 | F | 1 | CH₃ | CH₃ | C—H | I-12 | — | CH₃ | — |
| 76 | F | 0 | CH₃ | CH₃ | C—H | I-13 | — | H | — |
| 77 | F | 0 | Cl | Cl | C—H | I-13 | — | H | — |
| 78 | F | 0 | CH₃ | F | C—H | I-13 | — | H | — |
| 79 | F | 1 | CH₃ | F | C—H | I-13 | — | H | — |
| 80 | F | 1 | Cl | Cl | C—H | I-13 | — | H | — |
| 81 | F | 1 | CH₃ | CH₃ | C—H | I-13 | — | H | — |
| 82 | F | 0 | CN | F | C—H | I-16 | — | H | H |
| 83 | F | 0 | CH₃ | H | C—H | I-16 | — | H | H |
| 84 | F | 0 | OCH₃ | H | C—H | I-16 | — | H | H |
| 85 | F | 0 | Cl | H | C—H | I-16 | — | H | H |
| 86 | F | 1 | CH₃ | H | C—H | I-16 | — | H | H |
| 87 | F | 1 | Cl | H | C—H | I-16 | — | H | H |
| 88 | F | 1 | CN | H | C—H | I-16 | — | H | H |
| 89 | F | 1 | OCH₃ | H | C—H | I-16 | — | H | H |
| 90 | F | 0 | Cl | Cl | C—H | I-16 | — | H | H |
| 91 | F | 0 | CH₃ | CH₃ | C—H | I-16 | — | H | H |
| 92 | F | 0 | CH₃ | F | C—H | I-16 | — | H | H |
| 93 | F | 0 | CN | H | C—H | I-16 | — | H | H |
| 94 | F | 0 | CF₃ | H | C—H | I-16 | — | H | H |
| 95 | F | 1 | CN | H | C—H | I-16 | — | H | H |
| 96 | F | 1 | CH₃ | F | C—H | I-16 | — | H | H |
| 97 | F | 1 | CH₃ | CH₃ | C—H | I-16 | — | H | H |
| 98 | F | 1 | Cl | Cl | C—H | I-16 | — | H | H |
| 99 | F | 1 | CF₃ | H | C—H | I-16 | — | H | H |
| 100 | F | 0 | CH₃ | H | C—H | I-17 | — | H | H |
| 101 | F | 1 | CH₃ | H | C—H | I-17 | — | H | H |
| 102 | F | 0 | CN | H | C—H | I-17 | — | H | H |
| 103 | F | 0 | Cl | H | C—H | I-17 | — | H | H |
| 104 | F | 0 | CF₃ | H | C—H | I-17 | — | H | H |
| 105 | F | 1 | CN | H | C—H | I-17 | — | H | H |
| 106 | F | 1 | Cl | H | C—H | I-17 | — | H | H |
| 107 | F | 1 | CF₃ | H | C—H | I-17 | — | H | H |
| 108 | F | 0 | CH₃ | F | C—H | I-17 | — | H | H |
| 109 | F | 0 | CH₃ | F | C—H | I-17 | — | H | H |
| 110 | F | 0 | CH₃ | F | C—H | I-17 | — | H | Cl |
| 111 | F | 0 | CH₃ | F | C—H | I-17 | — | Cl | Cl |
| 112 | F | 1 | CH₃ | F | C—H | I-17 | — | H | H |
| 113 | F | 1 | CH₃ | F | C—H | I-17 | — | H | H |
| 114 | F | 1 | CH₃ | F | C—H | I-17 | — | H | Cl |
| 115 | F | 1 | CH₃ | F | C—H | I-17 | — | Cl | Cl |

-continued

| Com-pound | W | n | Y | X | Q | A—B | R¹ | R² | R³ |
|---|---|---|---|---|---|---|---|---|---|
| 116 | F | 0 | CH₃ | H | C—H | I-18 | — | C(CH₃)₃ | — |
| 117 | F | 0 | Cl | H | C—H | I-18 | — | C(CH₃)₃ | — |
| 118 | F | 1 | Cl | H | C—H | I-18 | — | C(CH₃)₃ | — |
| 119 | F | 0 | CH₃ | F | N | I-1 | CH₃ | H | — |
| 120 | F | 1 | CH₃ | F | N | I-1 | CH₃ | H | — |

Furthermore, the following compounds of the general formula (I) were prepared according to the processes described above:

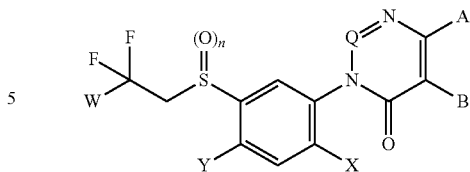

where Z=H according to the above general definition of the compounds of the general formula (I)

| Compound | W | n | Y | X | Q | A—B | R¹ | R² | R³ |
|---|---|---|---|---|---|---|---|---|---|
| 122 | F | 0 | Cl | F | C—H | I-1 | CH₃ | H | — |
| 123 | F | 1 | Cl | F | C—H | I-1 | CH₃ | H | — |
| 124 | F | 0 | CH₃ | F | C—H | I-1 | CH₂CH₃ | H | — |
| 125 | F | 0 | CH₃ | F | C—CH₃ | I-1 | CH₂CH₃ | H | — |
| 126 | F | 1 | CH₃ | F | C—H | I-1 | CH₂CH₃ | H | — |
| 127 | F | 1 | CH₃ | F | C—CH₃ | I-1 | CH₂CH₃ | H | — |
| 128 | F | 0 | CH₃ | F | C—H | I-2 | CH₃ | CH₃ | — |
| 129 | F | 1 | CH₃ | F | C—H | I-2 | CH₃ | CH₃ | — |
| 130 | F | 0 | CH₃ | CH₃ | C—H | I-2 | CH₃ | H | — |
| 131 | F | 0 | CH₃ | CH₃ | C—CH₃ | I-2 | CH₃ | H | — |
| 132 | F | 1 | CH₃ | CH₃ | N | I-2 | CH₃ | H | — |
| 133 | F | 0 | CH₃ | CH₃ | N | I-2 | CH₃ | H | — |
| 134 | F | 1 | CH₃ | CH₃ | C—H | I-2 | CH₃ | H | — |
| 135 | F | 1 | CH₃ | CH₃ | C—CH₃ | I-2 | CH₃ | H | — |
| 136 | F | 1 | CH₃ | F | N | I-2 | CH₃ | H | — |
| 137 | F | 0 | CH₃ | F | N | I-2 | CH₃ | H | — |
| 138 | F | 0 | CH₃ | H | C—H | I-2 | CH₃ | H | — |
| 139 | F | 0 | CH₃ | F | C—CH₃ | I-2 | CH₃ | H | — |
| 140 | F | 0 | Cl | Cl | C—H | I-2 | CH₃ | H | — |
| 141 | F | 0 | Cl | Cl | C—CH₃ | I-2 | CH₃ | H | — |
| 142 | F | 1 | CH₃ | H | C—H | I-2 | CH₃ | H | — |
| 143 | F | 1 | Cl | Cl | C—H | I-2 | CH₃ | H | — |
| 144 | F | 0 | Cl | Cl | C—CH₃ | I-2 | CH₃ | H | — |
| 145 | F | 1 | CH₃ | H | C—CH₃ | I-2 | CH₃ | H | — |
| 146 | F | 0 | CH₃ | F | C—CH₂CH₃ | I-2 | CH₃ | H | — |
| 147 | F | 1 | CH₃ | F | C—CH₂CH₃ | I-2 | CH₃ | H | — |
| 148 | F | 0 | Cl | F | C—H | I-2 | CH₃ | H | — |
| 149 | F | 0 | Cl | F | C—CH₃ | I-2 | CH₃ | H | — |
| 150 | F | 0 | Cl | F | N | I-2 | CH₃ | H | — |
| 151 | F | 0 | CH₃ | Cl | C—H | I-2 | CH₃ | H | — |
| 152 | F | 0 | CH₃ | Cl | C—CH₃ | I-2 | CH₃ | H | — |
| 153 | F | 1 | CH₃ | Cl | N | I-2 | CH₃ | H | — |
| 154 | F | 0 | CH₃ | Cl | N | I-2 | CH₃ | H | — |
| 155 | F | 1 | Cl | F | C—CH₃ | I-2 | CH₃ | H | — |
| 156 | F | 1 | Cl | F | C—H | I-2 | CH₃ | H | — |
| 157 | F | 1 | CH₃ | Cl | C—CH₃ | I-2 | CH₃ | H | — |
| 158 | F | 1 | CH₃ | Cl | C—H | I-2 | CH₃ | H | — |
| 159 | F | 0 | CH₃ | F | C—H | I-2 | CH₂CH₃ | H | — |
| 160 | F | 0 | CH₃ | F | C—CH₃ | I-2 | CH₂CH₃ | H | — |
| 161 | F | 0 | CH₃ | F | C—H | I-2 | CH(CH₃)₂ | H | — |
| 162 | F | 0 | CH₃ | F | C—CH₃ | I-2 | CH(CH₃)₂ | H | — |
| 163 | F | 1 | CH₃ | F | C—H | I-2 | CH₂CH₃ | H | — |
| 164 | F | 1 | CH₃ | F | C—CH₃ | I-2 | CH₂CH₃ | H | — |
| 165 | F | 1 | CH₃ | F | C—H | I-2 | CH(CH₃)₂ | H | — |
| 166 | F | 1 | CH₃ | F | C—CH₃ | I-2 | CH(CH₃)₂ | H | — |
| 167 | F | 0 | CH₃ | F | C—H | I-2 | CH₂cPr | H | — |
| 168 | F | 0 | CH₃ | F | C—CH₃ | I-2 | CH₂cPr | H | — |
| 169 | F | 1 | CH₃ | F | C—H | I-2 | CH₂cPr | H | — |
| 170 | F | 1 | CH₃ | F | C—CH₃ | I-2 | CH₂cPr | H | — |
| 171 | F | 0 | CH₃ | F | C—H | I-3 | CH₃ | CH₃ | — |
| 172 | F | 1 | CH₃ | F | C—H | I-3 | CH₃ | CH₃ | — |
| 173 | F | 0 | CH₃ | F | C—H | I-3 | CH₃ | H | — |
| 174 | F | 0 | CH₃ | F | C—CH₃ | I-3 | CH₃ | H | — |
| 175 | F | 1 | CH₃ | F | C—CH₃ | I-3 | CH₃ | H | — |
| 176 | F | 0 | CH₃ | F | C—H | I-3 | CH₂CH₃ | H | — |
| 177 | F | 1 | CH₃ | F | C—H | I-3 | CH₃ | H | — |
| 178 | F | 1 | CH₃ | F | C—H | I-8 | CH₃ | H | — |
| 179 | F | 1 | CH₃ | F | C—H | I-9 | CH₃ | H | — |
| 180 | F | 0 | CH₃ | F | C—H | I-11 | — | CH₃ | — |
| 181 | F | 1 | CH₃ | F | C—H | I-11 | — | CH₃ | — |
| 182 | F | 0 | CH₃ | F | N | I-11 | — | CH₃ | — |
| 183 | F | 1 | CH₃ | F | N | I-11 | — | CH₃ | — |

-continued

| Compound | W | n | Y | X | Q | A—B | R¹ | R² | R³ |
|---|---|---|---|---|---|---|---|---|---|
| 184 | F | 0 | CH₃ | F | C—CH₃ | I-12 | — | CH₃ | — |
| 185 | F | 1 | CH₃ | F | C—CH₃ | I-12 | — | CH₃ | — |
| 186 | F | 1 | CH₃ | CH₃ | C—CH₃ | I-12 | — | CH₃ | — |
| 187 | F | 0 | CH₃ | F | C—CH₃ | I-13 | — | H | — |
| 188 | F | 1 | CH₃ | F | C—CH₃ | I-13 | — | H | — |
| 189 | F | 0 | CH₃ | F | C—H | I-12 | — | CH₃ | — |
| 190 | F | 1 | CH₃ | F | C—H | I-12 | — | CH₃ | — |
| 191 | F | 0 | CH₃ | F | C—H | I-18 | — | C(CH₃)₃ | — |
| 192 | F | 1 | CH₃ | F | C—H | I-18 | — | C(CH₃)₃ | — |
| 193 | F | 0 | CH₃ | F | C—H | I-20 | — | CH(CH₃)₂ | — |
| 194 | F | 0 | CH₃ | F | C—H | I-20 | — | CH₃ | — |
| 195 | F | 0 | CH₃ | F | C—H | I-20 | — | CH₂CH₃ | — |
| 196 | F | 1 | CH₃ | F | C—H | I-20 | — | CH₃ | — |
| 197 | F | 0 | CH₃ | F | C—H | I-20 | — | CF₃ | — |
| 198 | F | 1 | CH₃ | F | C—H | I-20 | — | CH₂CH₃ | — |
| 199 | F | 1 | CH₃ | F | C—H | I-20 | — | CF₃ | — |
| 200 | F | 1 | CH₃ | F | C—H | I-20 | — | CH(CH₃)₂ | — |
| 201 | F | 0 | CH₃ | F | C—H | I-21 | — | CH₂CH₃ | — |
| 202 | F | 0 | CH₃ | F | C—H | I-21 | — | CH₃ | — |
| 203 | F | 1 | CH₃ | F | C—H | I-21 | — | CH₂CH₃ | — |
| 204 | F | 1 | CH₃ | F | C—H | I-21 | — | CH₃ | — |
| 205 | F | 0 | CH₃ | F | N | I-21 | — | CH₃ | — |
| 206 | F | 1 | CH₃ | F | N | I-21 | — | CH₃ | — |
| 207 | F | 0 | CH₃ | F | C—H | I-21 | — | C(CH₃)₃ | — |
| 208 | F | 1 | CH₃ | F | C—H | I-21 | — | C(CH₃)₃ | — |
| 209 | F | 0 | CH₃ | F | C—CH₃ | I-21 | — | CH₃ | — |
| 210 | F | 1 | CH₃ | F | C—CH₃ | I-21 | — | CH₃ | — |
| 211 | F | 0 | CH₃ | F | C—H | I-22 | — | H | — |
| 212 | F | 1 | CH₃ | F | C—H | I-22 | — | H | — |
| 213 | F | 0 | CH₃ | F | C—H | I-24 | CH₃ | CH₃ | — |
| 214 | F | 1 | CH₃ | F | C—H | I-24 | CH₃ | CH₃ | — |
| 215 | F | 0 | CH₃ | F | C—H | I-24 | CH₃ | H | — |
| 216 | F | 1 | CH₃ | F | C—H | I-24 | CH₃ | H | — |
| 217 | F | 0 | CH₃ | F | C—H | I-25 | — | CH₃ | H |
| 218 | F | 1 | CH₃ | F | C—H | I-25 | — | CH₃ | H |
| 219 | F | 0 | CH₃ | F | C—H | I-25 | — | H | CH₃ |
| 220 | F | 1 | CH₃ | F | C—H | I-25 | — | H | CH₃ |
| 221 | F | 0 | CH₃ | F | C—H | I-26 | — | CH₃ | H |
| 222 | F | 1 | CH₃ | F | C—H | I-26 | — | CH₃ | H |

NMR data of the compounds:

| Compound | logP[a] | logP[b] | 1H-NMR (D6-DMSO): |
|---|---|---|---|
| 1 | 2.66 | 2.65 | 8.41(s, 1H), 8.18(s, 1H), 7.83(d, 1H), 7.45(d, 1H), 4.05-3.98(m, 5H), 2.45(s, 3H) |
| 2 | 1.73 | 1.69 | 8.47(s, 1H), 8.20(s, 1H), 8.07(d, 1H), 7.58(d, 1H), 4.40-4.00(broad, 2H), 3.98(s, 3H), 2.48(s, 3H) |
| 3 | 2.94 | 2.94 | 8.39(s, 1H), 8.20(s, 1H), 8.03(s, 2H), 4.24-4.16(m, 2H), 3.99(s, 3H) |
| 4 | 2.11 | 2.09 | 8.41-8.16(m, 4H), 4.52-4.02(m, 2H), 3.98(d, 3H) |
| 5 | 3.18 | 3.11 | 8.13(s, 1H), 8.05(s, 1H), 8.02(s, 1H), 4.22-4.17(m, 2H), 3.95(s, 3H) |
| 6 | 2.92 | 2.86 | 8.09(s, 1H), 7.55(s, 1H), 7.33(s, 1H), 4.07-3.90(m, 5H), 2.38(s, 3H), 2.09(s, 3H), 1.95(s, 3H) |
| 7 | 2.79 | 2.73 | 8.27(s, 1H), 8.16(s, 1H), 7.56(s, 1H), 7.32(s, 1H), 4.02-3.94(m, 5H), 2.39(bs, 3H), 2.01(bs, 3H) |
| 8 | 2.56 | 2.54 | 8.35(s, 1H), 8.15(s, 1H), 7.65(d, 1H), 7.42(d, 1H), 7.31-7.28(m, 1H), 4.06(q, 2H), 3.97(s, 3H), 2.41(s, 3H) |
| 9 | 1.74 | 1.74 | 8.33(d, 1H), 8.18(d, 1H), 7.81(d, 1H), 7.44 (d, 1H), 4.30-3.93 (2xm, 5H), 2.43(s, 3H), 2.11(s, 3H) |
| 10 | 1.86 | 1.84 | 8.10(s) and 8.09(s)(1H), 7.79(s) and 7.77(s)(1H), 7.47-7.46(m, 1H), 4.31-4.15(m) and 3.96-3.90(m)(5H), 2.44-2.43(m, 3H), 2.17(s) and 2.08(s)(3H), 2.05-2.04(m, 3H) |
| 11 | 3.83 | 3.77 | 8.32(s, 1H), 7.68(s, 1H), 7.32(s, 1H), 4.05(s, 3H), 3.87(q, 2H), 2.40(s, 3H), 1.99(s, 3H) |
| 12 | 2.67, 2.73 | 2.64, 2.70 | 8.32-8.31(m, 1H), 7.99-7.92(m, 1H), 7.45(s, 1H), 4.30-4.23(m, 1H), 4.05(s, 3H), 3.88-3.70(m, 1H), 2.43(s, 3H), 2.09-2.08(m, 3H) |
| 13 | 3.75 | 3.94 | 8.35(s, 1H), 7.93(d, 1H), 7.49(d, 1H), 4.05(s, 3H), 3.89(q, 2H), 2.47(s, 3H) |
| 14 | 2.84 | 2.79 | 8.11(s, 1H), 7.81(d, 1H), 7.47(d, 1H), 4.07-3.92(m, 5H), 2.45(s, 3H), 2.20(s, 3H) |
| 15 | 1.85 | 1.84 | 8.12-8.11(m, 1H), 8.05(d, 1H), 7.60(dd, 1H), 4.38-4.20(m, 2H), 3.96-3.94(m, 3H), 3H under the DMSO peak, 2.27(s) and 2.21(s)(3H) |
| 16 | 2.67, 2.74 | 2.63, 2.70 | 8.35-8.34(m, 1H), 8.23-8.18(2xd, 1H), 7.62(d, 1H), 4.38-4.32(m, 1H), 4.05-4.04(m, 3H), 3.92-3.78(m, 1H), 3H under the DMSO peak |
| 17 | 3.31 | 3.21 | 8.53(s, 1H), 8.37(s, 1H), 7.88(d, 1H), 7.46(d, 1H), 5.37-5.34(m, 2H), 4.01(q, 2H), 2.45(s, 3H) |
| 18 | 2.34 | 2.33 | 8.56(s, 1H), 8.37(s, 1H), 8.14(d, 1H), 7.59(d, 1H), 5.35(q, 2H), 4.25-4.00(2xbroad, 2H), 3H under the DMSO peak |
| 19 | 4.20 | 4.10 | 8.53(s, 1H), 8.00(d, 1H), 7.52(d, 1H), 5.45(q, 2H), 3.94-3.86(m, 2H), 2.49(s, 3H) |
| 20 | 3.50 | 3.44 | 8.30(s, 1H), 7.87(d, 1H), 7.48(d, 1H), 5.32-5.25(m, 2H), 4.08-3.94(m, 2H), 2.45(s, 3H), 2.23(s, 3H) |
| 21 | 3.17, 3.26 | 3.14, 3.22 | 8.52-8.51(m, 1H), 8.31-8.26(2xd, 1H), 7.65(d, 1H), 5.43(q, 2H), 4.43-4.30(m, 1H), 3.92-3.74(m, 1H), 3H under the DMSO peak |

-continued

| Compound | logP[a] | logP[b] | 1H-NMR (D6-DMSO): |
|---|---|---|---|
| 22 | 2.52 | 2.45, 2.48 | 8.30-8.29(m, 1H), 8.14-8.11(2xd, 1H), 7.63-7.60(2xd, 1H), 5.28(q, 2H), 4.39-3.93(m, 2H), 3H under the DMSO peak, 2.30(s) and 2.23(s)(3H) |
| 23 | 2.58 | 2.53 | 1H-NMR (D6-DMSO): 8.38(s, 1H), 8.18(s, 1H), 7.82(d, 1H), 7.69(d, 1H), 7.43-7.40(m, 1H), 4.19(q, 2H), 3.97(s, 3H) |
| 24 | 2.07 | 2.06 | 8.43(s, 1H), 8.20(s, 1H), 8.09-8.05(m, 2H), 7.66-7.64(m, 1H), 4.27(q, 2H), 3.98(s, 3H) |
| 25 | 2.82 | 2.75 | 8.45(s, 1H), 8.20(s, 1H), 8.11(d, 1H), 7.96(d, 1H), 7.66-7.63(m, 1H), 4.24(q, 2H), 3.98(s, 3H) |
| 26 | 1.51 | 1.56 | 8.51(s, 1H), 8.32-8.26(m, 2H), 8.21(s, 1H), 8.02-8.00(m, 1H), 4.48-4.31(m, 2H), 3.99(s, 3H) |
| 27 | 1.57 | 1.57 | 8.43(s, 1H), 8.17(s, 1H), 7.93(d, 1H), 7.66-7.63(m, 1H), 7.54(d, 1H), 4.25-4.19(m, 1H), 4.08-4.01(m, 1H), 3.97(s, 3H), 2.46(s, 3H) |
| 28 | 1.80 | 1.80 | 8.45(s, 1H), 8.19(s, 1H), 8.00(d, 1H), 7.90-7.81(m, 2H), 4.36-4.26(m, 1H), 4.21-4.10(m, 1H), 3.98(s, 3H) |
| 29 | 2.16 | 2.11 | 8.54(s, 1H), 8.41(d, 1H), 8.22(s, 1H), 8.17(d, 1H), 8.05(d, 1H), 4.26(q, 2H), 3.99(s, 3H) |
| 30 | 2.81 | 2.73 | 8.28(s, 1H), 7.64(d, 1H), 7.40(d, 1H), 7.30-7.27(m, 1H), 4.06(q, 2H), 3.87(s, 3H), 2.44(s, 3H), 2.41(s, 3H) |
| 31 | 3.06 | 2.99 | 8.39(s, 1H), 8.10(d, 1H), 7.94(d, 1H), 7.63(d, 1H), 4.24(q, 2H), 3.89(s, 3H), 2.45(s, 3H) |
| 32 | 2.39 | 2.34 | 8.47(s, 1H), 8.40(d, 1H), 8.15(d, 1H), 8.04-8.02(m, 1H), 4.30-4.22(m, 2H), 3.90(s, 3H), 2.46(s, 3H) |
| 33 | 1.79 | 1.75 | 8.37(s, 1H), 7.91(d, 1H), 7.64-7.62(m, 1H), 7.54(d, 1H), 4.25-4.18(m, 1H), 4.07-4.01(m, 1H), 3.88(s, 3H), 2.46(s, 3H), 2.45(s, 3H) |
| 34 | 2.30 | 2.24 | 8.36(s, 1H), 8.08-8.05(m, 2H), 7.65-7.62(m, 1H), 4.27(q, 2H)), 3.88(s, 3H), 2.45(s, 3H) |
| 35 | 1.74 | 1.70 | 8.45(s, 1H), 8, .9(d, 1H), 8.25(d, 1H), 8.01-7.98(m, 1H), 4.48-4.31(m, 2H), 3.89(s, 3H), 2.46(s, 3H) |
| 36 | 2.82 | 2.79 | 8.30(s, 1H), 7.81(d, 1H), 7.68(d, 1H), 7.42-7.39(m, 1H), 4.19(q, 2H), 3.87(s, 3H), 2.44(s, 3H) |
| 37 | 2.01 | 1.98 | 8.38(s, 1H), 7.99(d, 1H), 7.86(d, 1H), 7.82-7.79(m, 1H), 4.35-4.29(m, 1H), 4.18-4.12(m, 1H), 3.88(s, 3H), 2.45(s, 3H) |
| 38 | 2.76 | 2.76 | 8.14(s, 1H), 8.10(s, 1H), 7.85(d, 1H), 7.47(d, 1H), 4.22(s, 3H), 4.01(q, 2H), 2.46(s, 3H) |
| 39 | 2.94 | 2.87 | 8.00(s, 1H), 7.85(d, 1H), 7.49(d, 1H), 4.17(s, 3H), 4.09-3.94(m, 2H), 2.46(s, 3H), 2.12(s, 3H) |
| 40 | 1.82 | 1.81 | 8.20(s, 1H), 8.11(s, 1H), 8.08(d, 1H), 7.60(d, 1H), 4.23-4.01(m, 5H), 2.49(s, 3H) |
| 41 | 1.90 | 1.88 | 8.07(dd, 1H), 8.00(s, 1H), 7.63(dd, 1H), 4.38-4.17(m, 4H), 4.01-3.95(m, 1H), 2.19(s, 3H), 2.11(s, 3H) |
| 42 | 3.27 | 3.19 | 8.80(s, 1H), 7.94(d, 1H), 7.46(d, 1H), 4.11(s, 3H), 3.91(q, 2H), 2.43(s, 3H) |
| 43 | 2.32, 2.37 | 2.25, 2.31 | 8.80(s, 1H), 8.22-8.17(m, 1H), 7.60(d, 1H), 4.38-4.28(m, 1H), 4.11(s, 3H), 3.94-3.76(m, 1H), 2.50(s, 3H) |
| 44 | 2.38 | 2.33 | 8.10(s, 1H), 7.62(d, 1H), 7.39(d, 1H), 7.27-7.25(m, 1H), 4.06(q, 2H), 3.90(s, 3H), 2.61(s, 3H), 2.40(s, 3H) |
| 45 | 2.70 | 2.63 | 8.20(s, 1H), 8.08(d, 1H), 7.92(d, 1H), 7.62-7.60(m, 1H), 4.25(q, 2H), 3.92(s, 3H), 2.62(s, 3H) |
| 46 | 2.11 | 2.07 | 8.37(d, 1H), 8.31(s, 1H), 8.13(d, 1H), 8.03-8.00(m, 1H), 4.35-4.19(m, 2H), 3.92(s, 3H), 2.64(s, 3H) |
| 47 | 1.54 | 1.51 | 8.20(s, 1H), 7.88(d, 1H), 7.63-7.60(m, 1H), 7.51(d, 1H), 4.23-4.05(m, 2H), 3.91(s, 3H), 2.62(s, 3H), 2.45(m, 3H) |
| 48 | 2.45 | 2.36 | 8.12(s, 1H), 7.79(d, 1H), 7.66(d, 1H), 7.39-7.37(m, 1H), 4.21(q, 2H), 3.91(s, 3H), 2.61(s, 3H) |
| 49 | 1.78 | 1.75 | 8.22(s, 1H), 7.95(d, 1H), 7.84(d, 1H), 7.80-7.78(m, 1H), 4.33-4.14(m, 2H), 3.91(s, 3H), 2.62(s, 3H) |
| 50 | 1.99 | 1.92 | 8.19(s, 1H), 8.06-8.02(m, 2H), 7.63-7.60(m, 1H), 4.28(q, 2H), 3.91(s, 3H), 2.62(s, 3H) |
| 51 | 1.52 | 1.50 | 8.29(s, 1H), 8.27(d, 1H), 8.22(d, 1H), 8.00-7.97(m, 1H), 4.47-4.34(m, 2H), 3.92(s, 3H), 2.63(s, 3H) |
| 52 | 2.17 | 2.11 | 8.38(s, 1H), 8.16(s, 1H), 7.81(d, 1H), 7.45(d, 1H), 4.01(q, 2H), 3.79(s, 3H), 2.45(s, 3H) |
| 53 | 2.46 | 2.41 | 8.37(s, 1H), 8.23(s, 1H), 7.82(d, 1H), 7.45(d, 1H), 4.23(q, 2H), 4.02(q, 2H), 2.45(s, 3H), 1.44(t, 3H) |
| 54 | 1.60 | 1.59 | 8.43(s, 1H), 8.24(s, 1H), 8.05(d, 1H), 7.58(d, 1H), 4.26-4.08(q + broad, 4H), 3H under the DMSO peak, 1.45(t, 3H) |
| 55 | 2.28 | 2.23 | 8.24(s, 1H), 8.14(s, 1H), 7.54(s, 1H), 7.32(s, 1H), 3.99(q, 2H), 3.79(s, 3H), 2.39(s, 3H), 2.04(s, 3H) |
| 56 | 2.36 | 2.35 | 8.06(s, 1H), 7.52(s, 1H), 7.22(s, 1H), 4.08-3.90(m, 2H), 3.76(s, 3H), 2.39(s, 3H), 2.14(s, 3H), 1.94(s, 3H) |
| 57 | 2.19 | 2.17 | 8.40(s, 1H), 8.17(s, 1H), 8.01(d, 1H), 7.89(d, 1H), 4.16(q, 2H), 3.80(s, 3H) |
| 58 | 1.43 | 1.40 | 8.32-8.30(m, 1H), 8.15(s, 1H), 7.79-7.69(m, 1H), 7.46-7.44(m, 1H), 4.30-3.95 (m, 2H), 3.80(m, 3H), 2.44(m, 3H), 2.11-2.10(m, 3H) |
| 59 | 1.52 | 1.50 | 8.07(s, 1H), 7.75(s) and 7.73(s)(1H), 7.48-7.47(m, 1H), 4.31-3.91(m, 2H) and 3.77-3.76(m, 3H), 2.45-2.43(m, 3H), 2.30(s) and 2.08(s, 3H), 2.04-2.03(m, 3H) |
| 60 | 2.54 | 2.52 | 9.29(s, 1H), 8.58(s, 1H), 7.89(d, 1H), 7.48(d, 1H), 4.01(q, 2H), 2.46(s, 3H) |
| 61 | 1.57 | 1.56 | 9.29(s, 1H), 8.63(s, 1H), 8.16(d, 1H), 7.61(d, 1H), 4.25(broad, 1H), 4.07(broad, 1H), 2.09(s, 3H) |
| 62 | 2.67 | 2.64 | 9.27(s, 1H), 8.44(s, 1H), 7.64(s, 1H), 7.35(s, 1H), 3.99(q, 2H), 2.40(s, 3H), 2.05(s, 3H) |
| 63 | 2.83 | 2.77 | 9.31(s, 1H), 8.56(s, 1H), 8.11(s, 1H), 8.07(s, 1H), 4.25-4.14(m, 2H) |
| 64 | 2.72 | 2.70 | 9.21(s, 1H), 7.88(d, 1H), 7.51(d, 1H), 4.07-3.93(m, 2H), 2.46(s, 3H), 2.22(s, 3H) |
| 65 | 3.55 | 3.51 | 9.50(s, 1H), 7.98(d, 1H), 7.53(d, 1H), 3.95-3.83(m, 2H), 3H under the DMSO peak |
| 66 | 1.6 | 1.62 | 9.28(s, 1H), 8.50-8.49(m, 1H), 7.91-7.89(m, 1H), 7.48-7.46(m, 1H), 4.31-3.91(m, 2H), 2.45-2.44(m, 3H), 2.16-2.15(m, 3H) |
| 67 | 1.96 | 1.96 | 9.30-9.29(m, 1H), 8.57-8.52(m, 1H), 8.32-8.27(m, 2H), 4.54-4.10(m, 2H) |
| 68 | 1.72 | 1.70 | 9.21(s, 1H), 8.16-8.14(m, 1H), 7.66-7.63(m, 1H), 4.40-3.92(m, 2H), 2.29(s, 3H), 2.21(s, 3H) |
| 69 | 2.55, 2.47 | 2.53, 2.45 | 9.49(s, 1H), 8.27(d, 1H), 7.66(d, 1H), 4.42-3.81(m, 2H), 3H under DMSO peak and 9.49(s, 1H), 8.30(d, 1H), 7.67(d, 1H), 4.40-3.78(m, 2H), 3H under DMSO peak |
| 70 | 2.80 | 2.74 | 8.51(s, 1H), 7.88(d, 1H), 7.47(d, 1H), 4.02(q, 2H), 2.78(s, 3H), 2.46(s, 3H) |
| 71 | 3.09 | 3.02 | 8.49(s, 1H), 8.09(s, 1H), 8.06(s, 1H), 4.24-4.15(m, 2H), 2.79(s, 3H) |
| 72 | 2.92 | 2.86 | 8.37(s, 1H), 7.62(s, 1H), 7.34(s, 1H), 4.03-3.95(m, 2H), 2.78(s, 3H), 2.39(s, 3H), 2.04(s, 3H) |
| 73 | 1.80 | 1.77 | 8.56(s, 1H), 8.14(d, 1H), 7.59(d, 1H), 4.37-3.96(m, 2H), 2.79(s, 3H), 2.09(s, 3H) |
| 74 | 2.22 | 2.17 | 8.50-8.45(m, 1H), 8.28-8.25(m, 2H), 4.53-4.11(m, 2H), 2.79(s, 3H) |
| 75 | 1.84 | 1.81 | 8.42(s, 1H), 7.88-7.87(m, 1H), 7.47-7.45(m, 1H), 4.28-3.92(m, 2H), 2.78(s, 3H), 2.44-2.43(m, 3H), 2.15-2.14(m, 3H) |
| 76 | 2.62 | 2.59 | 9.72(s, 1H), 8.48(s, 1H), 7.65(s, 1H), 7.34(s, 1H), 3.99(q, 2H), 2.40(s, 3H), 2.05(s, 3H) |
| 77 | 2.79 | 2.76 | 9.76(s, 1H), 8.60(s, 1H), 8.11(s, 1H), 8.07(s, 1H), 4.26-4.13(m, 2H) |
| 78 | 2.51 | 2.48 | 9.74(s, 1H), 8.62(s, 1H), 7.90(d, 1H), 7.49(d, 1H), 4.01(q, 2H), 2.46(s, 3H) |

-continued

| Compound | logP[a] | logP[b] | 1H-NMR (D6-DMSO): |
|---|---|---|---|
| 79 | 1.60 | 1.57 | 9.74(s, 1H), 8.67(s, 1H), 8.16(d, 1H), 7.61(d, 1H), 4.29-4.06(m, 2H), 3H under the DMSO peak |
| 80 | 2.01 | 1.98 | 9.75(s, 1H), 8.61(s, 1H), 8.56(s, 1H), 8.32-8.27(m, 2H), 4.54-4.02(m, 2H) |
| 81 | 1.65 | 1.62 | 9.73-9.72(m, 1H), 8.52(s, 1H), 7.91-7.90(m, 1H), 7.48-7.46(m, 1H), 4.31-3.90(m, 2H), 2.45-2.44(m, 3H), 2.16-2.15(m, 3H) |
| 82 | 2.70 | 2.67 | 8.49(s, 1H), 8.27-8.29(m, 2H), 7.76(d, 1H), 7.52(d, 1H), 4.18-4.26(m, 2H) |
| 83 | 3.09 | 3.01 | 8.37(s, 1H), 7.71-7.67(m, 2H), 7.47(d, 1H), 7.42(d, 1H), 7.36-7.33(m, 1H), 4.06(q, 2H), 2.41(s, 3H) |
| 84 | 2.75 | 2.71 | 8.33(s, 1H), 7.67(d, 1H), 7.63(d, 1H), 7.47(d, 1H), 7.43-7.40(m, 1H), 7.19(d, 1H), 4.00(q, 2H), 3.92(s, 3H) |
| 85 | 3.09 | 3.03 | 8.39(s, 1H), 7.88(d, 1H), 7.72-7.69(m, 2H), 7.50-7.45(m, 2H), 4.19(q, 2H) |
| 86 | 1.94 | 1.93 | 8.46(s, 1H), 7.97(d, 1H), 7.71-7.69(m, 2H), 7.55(d, 1H), 7.48(d, 1H), 4.26-4.16(m, 1H), 4.11-4.02(m, 1H), 2.46(s, 3H) |
| 87 | 2.20 | 2.17 | 8.47(s, 1H), 8.06(s, 1H), 7.88(s, 2H), 7.70(d, 1H), 7.49(d, 1H), 4.38-4.27(m, 1H), 4.21-4.12(m, 1H) |
| 88 | 2.07 | 2.00 | 8.53-8.47(m, 3H), 7.76(d, 1H), 7.53(d, 1H), 4.48-4.33(m, 2H) |
| 89 | 1.91 | 1.91 | 8.40(s, 1H), 7.79-7.76(m, 2H), 7.69-7.67(m, 1H), 7.48-7.46(m, 1H), 7.39(d, 1H), 4.24-4.15(m, 1H), 4.06-3.91(m, 1H), 3.97(s, 3H) |
| 90 | 3.51 | 3.42 | 8.41(s, 1H), 8.09(s, 1H), 8.05(s, 1H), 7.75(d, 1H), 7.51(d, 1H), 4.26-4.15(m, 2H) |
| 91 | 3.34 | 3.25 | 8.29(s, 1H), 7.70(d, 1H), 7.61(s, 1H), 7.48(d, 1H), 7.33(s, 1H), 4.00(q, 2H), 2.39(s, 3H), 2.04(s, 3H) |
| 92 | 3.22 | 3.14 | 8.43(s, 1H), 7.87(d, 1H), 7.72(d, 1H), 7.50-7.45(m, 2H), 4.00 (q, 2H), 2.45(s, 3H) |
| 93 | 2.48 | 2.46 | 8.45(1H), 8.09(d, 2H), 7.72-7.69(m, 2H), 7.50(d, 1H), 4.27(q, 2H) |
| 94 | 3.27 | 3.21 | 8.47(s, 1H), 8.16(d, 1H), 7.97(d, 1H), 7.72-7.69(m, 2H),7.51(d, 1H), 4.24(q, 2H) |
| 95 | 1.89 | 1.87 | 8.53(s, 1H), 8.32-8.30(m, 2H), 8.07-8.05(m, 1H), 7.72(d, 1H), 7.51(d, 1H), 4.49-4.28(m, 2H) |
| 96 | 2.10 | 2.09 | 8.49(s, 1H), 8.12(d, 1H), 7.73(d, 1H), 7.59(d, 1H), 7.50(d, 1H), 4.28-4.06(m, 2H), 3H under the DMSO peak |
| 97 | 2.15 | 2.11 | 8.36(s, 1H), 7.86-7.85(m, 1H), 7.72-7.70(m, 1H), 7.50-7.45(m, 2H), 4.30-3.94(m, 2H), 2.44(s, 3H), 2.14(s, 3H) |
| 98 | 2.53 | 2.53 | 8.43 and 8.38(s, 1H), 8.27-8.21(m, 2H), 7.74-7.73(m, 1H), 7.52-7.50(m, 1H), 4.52-4.45 and 4.30-4.12(m, 2H) |
| 99 | 2.54 | 2.51 | 8.56(s, 1H), 8.46(d, 1H), 8.18(d, 1H), 8.11-8.09(m, 1H), 7.73(d, 1H), 7.52(d, 1H), 4.27(q, 2H) |
| 100 | 2.87 | 2.79 | 8.38(s, 1H), 8.27(d, 1H), 7.72(d, 1H), 7.49(d, 1H), 7.43(d, 1H), 7.37-7.35(m, 1H), 4.07(q, 2H), 2.41(s, 3H) |
| 101 | 1.82 | 1.81 | 8.48(s, 1H), 8.28(d, 1H), 7.98(d, 1H), 7.73-7.70(m, 1H), 7.55(d, 1H), 7.50(d, 1H), 4.02-4.26(m, 2H), 2.47(s, 3H) |
| 102 | 2.37 | 2.31 | 8.47(s, 1H), 8.31(d, 1H), 8.12(d, 1H), 8.10(d, 1H), 7.73-7.71(m, 1H), 7.51(d, 1H), 4.28(q, 2H) |
| 103 | 2.90 | 2.84 | 8.40(s, 1H), 8.29(d, 1H), 7.89(d, 1H), 7.71(d, 1H), 7.51-7.47(m, 2H), 4.20(q, 2H) |
| 104 | 3.09 | 3.07 | 8.48(s, 1H), 8.31(d, 1H), 8.17(d, 1H), 7.97(d, 1H), 7.73-7.70(m, 1H), 7.51(d, 1H), 4.25(q, 2H) |
| 105 | 1.79 | 1.75 | 8.55(s, 1H), 8.33-8.30(m, 3H), 8.09-8.07(m, 1H), 7.52(d, 1H), 4.49-4.30(m, 2H) |
| 106 | 2.07 | 2.03 | 8.48(s, 1H), 8.30(d, 1H), 8.07-8.06(m, 1H), 7.91-7.86(m, 2H), 7.51(d, 1H), 4.38-4.26(m, 1H), 4.23-4.11(m, 1H) |

-continued

| Compound | logP[a] | logP[b] | 1H-NMR (D6-DMSO): |
|---|---|---|---|
| 107 | 2.44 | 2.40 | 8.58(s, 1H), 8.47(d, 1H), 8.32(d, 1H), 8.18(d, 1H), 8.13-8.11(m, 1H), 7.53(d, 1H), 4.33-4.22(m, 2H) |
| 108 | 3.01 | 2.90 | 8.43(s, 1H), 8.32(d, 1H), 7.89(d, 1H), 7.51(d, 1H), 7.47(d, 1H), 4.02(q, 2H), 2.45(s, 3H) |
| 109 | 3.50 | 3.42 | 8.45(s, 1H), 7.97(s, 1H), 7.88(d, 1H), 7.47(d, 1H), 4.02(q, 2H), 2.45(s, 3H), 2.37(s, 3H) |
| 110 | 3.56 | 3.41 | 8.56(s, 1H), 8.44(s, 1H), 7.90(d, 1H), 7.49(d, 1H), 4.01(q, 2H), 2.46(s, 3H) |
| 111 | 4.38 | 4.24 | 8.63(s, 1H), 7.89(d, 1H), 7.49(d, 1H), 4.04-3.97(m, 2H), 2.46(s, 3H) |
| 112 | 1.96 | 1.95 | 8.50(s, 1H), 8.32(d, 1H), 8.12(s, 1H), 7.59(d, 1H), 7.52(d, 1H), 4.28-4.07(m, 2H), 3H under the DMSO peak |
| 113 | 2.35 | 2.31 | 8.51(s, 1H), 8.11(d, 1H), 7.98-7.97(m, 1H), 7.60(d, 1H), 4.32-4.01(m, 2H), 2.38(s, 3H), 3H under the DMSO peak |
| 114 | 2.43 | 2.38 | 8.61(s, 1H), 8.43(s, 1H), 8.15(d, 1H), 7.61(d, 1H), 4.29-4.23(m, 1H), 4.11-4.04(m, 1H), 3H under the DMSO peak |
| 115 | 3.20 | 3.13 | 8.67(s, 1H), 8.16(d, 1H), 7.61(d, 1H), 4.29-4.21(m, 1H), 4.09-3.99(m, 1H), 3H under the DMSO peak |
| 116 | 4.05 | 3.96 | 8.33(s, 1H), 7.69(d, 1H), 7.42(d, 1H), 7.35-7.32(m, 1H), 4.06(q, 2H); 2.41(s, 3H), 1.57(s, 9H) |
| 117 | 4.06 | 3.97 | 8.35(s, 1H), 7.86(d, 1H), 7.70(d, 1H), 7.47-7.45(m, 1H), 4.19(q, 2H), 1.57(s, 9H) |
| 118 | 3.14 | 3.08 | 8.41(s, 1H), 8.05(d, 1H), 7.88-7.83(m, 2H), 4.34-4.28(m, 1H), 4.21-4.15(m, 1H), 1.58(s, 9H) |
| 119 | 3.16 | 3.13 | 8.50(s, 1H), 7.90(d, 1H), 7.51(d, 1H), 4.25(s, 3H), 3.97(q, 2H), 3H under the DMSO peak |
| 120 | 2.14 | 2.10 | 8.50(s, 1H), 8.16(d, 1H), 7.63(d, 1H), 4.36-4.25(m, 4H), 4.07-4.01(m, 1H), 3H under the DMSO peak |

NMR Peak List Method

The 1H NMR data of selected examples are stated in the form of 1H NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of:

$$\delta_1(\text{intensity}_1); \delta_2(\text{intensity}_2); \ldots;$$
$$\delta_i(\text{intensity}_i); \ldots; \delta_n(\text{intensity}_n)$$

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Example 122: $^1$H-NMR (400.0 MHz, DMSO):

δ = 8.428(5.6); 8.205(6.1); 8.030(2.1); 8.012(2.1); 7.906(2.6); 7.882(2.6); 4.189(0.7); 4.164(2.0); 4.138(2.0); 4.113(0.7); 3.981(16.0); 3.323(24.8); 2.524(0.5); 2.511(11.9); 2.507(23.7); 2.502(31.6); 2.497(23.4); 2.493(11.5); 0.000(0.5)
Example 123: $^1$H-NMR (400.0 MHz, DMSO):

δ = 8.460(3.9); 8.210(6.4); 8.188(1.8); 8.169(1.8); 8.096(1.8); 8.072(1.8); 5.756(0.5); 3.984(16.0); 3.321(36.7); 2.671(0.3); 2.524(0.9); 2.519(1.5); 2.511(17.9); 2.506(36.2); 2.502(48.1); 2.497(34.7); 2.492(16.3); 0.008(0.6); 0.000(16.2); −0.009(0.5)
Example 124: $^1$H-NMR (400.0 MHz, DMSO):

δ = 8.691(7.7); 8.313(0.4); 8.199(7.6); 7.867(0.3); 7.807(3.0); 7.789(3.0); 7.439(2.6); 7.412(2.6); 4.365(1.5); 4.347(4.7); 4.329(4.8); 4.311(1.5); 4.048(1.2); 4.022(3.7); 3.996(3.8); 3.970(1.3); 3.319(23.1); 2.676(0.3); 2.671(0.4); 2.511(26.2); 2.507(50.6); 2.502(66.8); 2.498(49.6); 2.493(24.4); 2.442(16.0); 2.404(0.5); 2.395(1.2); 2.334(0.3); 2.329(0.4); 2.325(0.3); 1.488(5.7); 1.470(12.3); 1.452(5.6); 1.227(0.5); 0.008(2.5); 0.000(53.8); −0.008(1.9)
Example 125: $^1$H-NMR (400.0 MHz, DMSO):

δ = 8.693(0.4); 8.616(6.5); 8.201(0.4); 7.867(0.3); 7.804(2.4); 7.785(2.4); 7.454(2.1); 7.427(2.1); 4.333(1.2); 4.315(3.8); 4.297(3.8); 4.279(1.2); 4.087(0.5); 4.073(0.4); 4.061(0.6); 4.048(1.2); 4.022(1.4); 3.994(1.2); 3.968(1.2); 3.954(0.5); 3.942(0.6); 3.928(0.6); 3.318(14.4); 2.671(0.4); 2.524(1.0); 2.519(1.6); 2.511(21.7); 2.506(44.4); 2.502(60.0); 2.497(44.2); 2.493(21.1); 2.441(13.7); 2.425(0.4); 2.395(1.2); 2.328(0.4); 2.110(16.0); 1.487(0.3); 1.469(5.1); 1.451(10.7); 1.433(4.6); 1.226(0.6); 0.008(1.9); 0.000(59.9); −0.009(2.0)
Example 126: $^1$H-NMR (400.0 MHz, DMSO):

δ = 8.710(7.8); 8.315(0.4); 8.274(4.4); 8.039(3.0); 8.020(3.1); 7.898(0.4); 7.568(2.2); 7.541(2.1); 4.369(1.5); 4.351(4.6); 4.333(4.7); 4.315(1.6); 4.228(0.4); 4.195(0.4); 4.167(0.4); 4.157(0.4); 4.139(0.5); 4.121(0.5); 3.931(0.3); 3.320(47.2); 2.675(0.6); 2.671(0.8); 2.666(0.6); 2.541(0.5); 2.524(2.3); 2.511(50.1); 2.506(97.9); 2.502(125.3); 2.497(88.3); 2.493(41.1); 2.477(16.0); 2.441(0.4); 2.365(0.4); 2.354(1.1); 2.333(0.7); 2.328(0.9); 2.324(0.7); 1.495(6.0); 1.477(13.2); 1.459(5.8); 1.249(0.4); 1.232(1.1); 1.214(0.4); 0.146(0.6); 0.008(6.1); 0.000(143.8); −0.009(4.7); −0.150(0.6)
Example 127: $^1$H-NMR (400.0 MHz, DMSO):

δ = 8.710(0.7); 8.637(4.6); 8.625(6.4); 8.315(0.5); 8.274(0.4); 8.023(2.6); 8.015(1.9); 8.004(2.5); 7.996(1.8); 7.899(0.5); 7.598(1.9); 7.593(1.5); 7.572(2.0); 7.566(1.6); 4.366(0.8); 4.356(0.4); 4.351(0.5); 4.339(2.1); 4.330(1.3); 4.322(4.2); 4.303(4.9); 4.285(1.4); 4.276(0.9); 4.249(1.8); 4.222(2.0); 4.195(0.8); 4.020(0.8); 3.993(1.0); 3.983(0.8); 3.966(0.4); 3.956(0.9); 3.930(0.6); 3.913(0.3); 3.506(0.4); 3.321(81.1); 2.680(0.3); 2.675(0.7); 2.671(1.0); 2.666(0.7); 2.541(0.7); 2.524(2.5); 2.519(3.9); 2.511(55.7); 2.506(113.6); 2.502(149.4); 2.497(106.3); 2.493(52.8); 2.476(10.3); 2.425(0.4); 2.354(1.3); 2.333(0.8); 2.328(1.0); 2.324(0.8); 2.187(10.5); 2.102(15.2); 1.495(0.6); 1.477(8.1); 1.459(16.0); 1.441(7.0); 1.249(0.5); 1.232(1.3); 1.214(0.5); 1.187(0.5); 1.169(0.3); 0.146(0.7); 0.008(6.1); 0.000(177.1); −0.009(5.9); −0.150(0.8)
Example 128: $^1$H-NMR (601.6 MHz, DMSO):

δ = 8.094(5.4); 7.838(2.0); 7.826(2.0); 7.473(1.7); 7.455(1.7); 5.755(0.7); 4.144(16.0); 4.033(0.7); 4.016(2.3); 3.999(2.4); 3.982(0.9); 3.320(15.3); 2.523(0.3); 2.520(0.4); 2.517(0.4); 2.508(13.0); 2.505(28.0); 2.502(39.0); 2.499(28.5); 2.496(13.8); 2.454(12.1); 2.405(15.1); 0.000(7.8); −0.006(0.3)
Example 129: $^1$H-NMR (400.0 MHz, DMSO):

δ = 8.155(4.6); 8.126(0.4); 8.069(2.3); 8.050(2.3); 7.606(1.5); 7.580(1.5); 5.756(2.2); 4.147(16.0); 3.320(45.9); 2.753(0.9); 2.675(0.6); 2.671(0.8); 2.666(0.6); 2.541(0.5); 2.524(2.1); 2.511(42.5); 2.506(86.4); 2.502(114.4); 2.497(82.7); 2.492(40.5); 2.487(14.9); 2.411(15.0); 2.333(0.6); 2.328(0.7); 2.324(0.6); 1.235(0.4); 0.000(9.0)
Example 130: $^1$H-NMR (400.0 MHz, DMSO):

δ = 8.088(5.8); 7.997(6.3); 7.592(3.9); 7.335(3.1); 4.220(16.0); 4.027(0.6); 4.001(1.9); 3.989(0.6); 3.974(1.9); 3.948(0.7); 3.323(16.6); 2.524(0.7); 2.511(11.5); 2.506(22.7); 2.502(29.6); 2.497(21.4); 2.493(10.3); 2.395(10.5); 2.039(10.8); 0.000(8.1)
Example 131: $^1$H-NMR (400.0 MHz, DMSO):

δ = 7.981(5.5); 7.574(4.0); 7.345(3.3); 7.200(0.4); 4.174(16.0); 4.086(0.5); 4.072(0.3); 4.060(0.6); 4.046(1.0); 4.027(1.2); 4.021(1.1); 3.995(0.5); 3.974(1.0); 3.948(1.0); 3.934(0.5); 3.922(0.4); 3.908(0.5); 3.322(29.7); 2.675(0.3); 2.671(0.5); 2.666(0.3); 2.510(27.5); 2.506(53.1); 2.502(69.0); 2.497(50.7); 2.493(25.2); 2.391(11.2); 2.357(0.8); 2.333(0.4); 2.328(0.5); 2.324(0.4); 2.269(0.7); 2.019(14.7); 1.971(11.5); 0.008(0.7); 0.000(15.6); −0.008(0.6)
Example 132: $^1$H-NMR (400.0 MHz, DMSO):

δ = 8.653(6.2); 7.912(4.1); 7.488(3.1); 4.281(16.0); 4.266(0.5); 4.257(0.5); 4.229(0.4); 3.322(22.5); 2.524(0.8); 2.511(15.8); 2.506(31.3); 2.502(40.8); 2.497(29.3); 2.492(13.8); 2.446(10.2); 2.154(10.6); 2.074(0.3); 0.008(0.8); 0.000(22.1); −0.009(0.7)
Example 133: $^1$H-NMR (400.0 MHz, DMSO):

δ = 8.651(5.9); 7.648(3.6); 7.368(2.7); 4.283(16.0); 3.971(0.7); 3.945(2.3); 3.919(2.4); 3.893(0.8); 3.321(34.2); 2.675(0.6); 2.670(0.7); 2.666(0.5); 2.524(2.2); 2.519(3.2); 2.510(40.4); 2.506(80.9); 2.501(105.6); 2.497(75.1); 2.492(35.1); 2.430(9.7); 2.333(0.5); 2.328(0.7); 2.324(0.5); 2.045(10.1); 0.008(1.7); 0.000(53.2); −0.009(1.7)
Example 134: $^1$H-NMR (400.0 MHz, DMSO):

δ = 8.098(7.1); 8.096(5.2); 8.064(6.5); 8.054(4.6); 7.826(6.2); 7.473(2.1); 7.451(3.0); 4.298(0.4); 4.270(0.5); 4.261(0.6); 4.243(0.4); 4.233(1.2); 4.225(11.8); 4.219(16.0); 4.160(0.7); 4.133(2.4); 4.106(2.5); 4.079(0.9); 3.988(0.5); 3.961(0.6); 3.951(0.5); 3.924(0.5); 3.320(14.2); 2.671(0.4); 2.511(24.5); 2.506(47.9); 2.502(62.1); 2.497(44.2); 2.493(21.0); 2.442(8.1); 2.434(10.8); 2.328(0.4); 2.151(11.7); 2.146(8.8); 0.008(1.8); 0.000(41.5); −0.009(1.4)
Example 135: $^1$H-NMR (400.0 MHz, DMSO):

δ = 7.990(6.7); 7.793(4.6); 7.789(3.6); 7.488(3.0); 7.476(2.3); 5.757(13.9); 4.299(0.6); 4.290(0.3); 4.271(0.7); 4.262(1.0); 4.253(0.3); 4.244(0.4); 4.235(1.3); 4.226(0.9); 4.208(1.2); 4.199(1.1); 4.180(16.0); 4.168(12.2); 4.153(0.4); 4.137(0.5); 3.977(0.8); 3.950(0.9); 3.941(0.7); 3.923(0.3); 3.914(0.7); 3.321(37.6); 2.675(0.5); 2.671(0.7); 2.666(0.5); 2.524(2.0); 2.519(3.0); 2.510(40.0); 2.506(79.7); 2.501(104.4); 2.497(74.6); 2.492(35.2); 2.452(10.2); 2.435(8.0); 2.357(0.3); 2.332(0.7); 2.328(0.9); 2.324(0.6); 2.319(0.4); 2.304(0.4); 2.099(10.5); 2.080(12.7); 2.019(0.4); 2.002(14.0); 1.398(0.4); 1.235(0.3); 0.008(1.5); 0.000(46.9); −0.009(1.4)
Example 136: $^1$H-NMR (400.0 MHz, DMSO):

δ = 8.676(5.2); 8.158(2.2); 8.139(2.2); 7.654(1.8); 7.627(1.7); 5.757(0.8); 4.359(0.6); 4.332(0.7); 4.322(0.9); 4.305(0.4); 4.294(1.3); 4.286(16.0); 4.268(0.4); 4.072(0.8); 4.045(0.8); 4.035(0.7); 4.018(0.3); 4.008(0.6); 3.322(37.0); 2.675(0.5); 2.670(0.6); 2.666(0.5); 2.506(72.9); 2.501(94.0); 2.497(75.2); 2.332(0.5); 2.328(0.6); 2.324(0.5); 0.000(1.8)
Example 137: $^1$H-NMR (400.0 MHz, DMSO):

δ = 8.676(5.5); 7.913(2.0); 7.895(2.0); 7.532(1.8); 7.505(1.8); 4.286(16.0); 4.027(0.4); 4.006(0.9); 3.980(2.7); 3.954(2.8); 3.929(1.0); 3.323(11.0); 2.511(14.1); 2.507(27.0); 2.502(35.2); 2.497(29.8); 2.075(1.0); 1.234(0.4); 0.000(0.9)

Example 138: ¹H-NMR (400.0 MHz, DMSO):

δ = 8.091(5.9); 8.071(5.4); 7.695(2.3); 7.690(2.3); 7.439(1.5); 7.419(2.2); 7.344(1.6); 7.339(1.5); 7.324(1.1); 7.319(1.1); 5.757(2.0); 4.218(16.0); 4.105(1.4); 4.079(2.6); 4.053(2.8); 4.038(0.7); 4.027(0.9); 4.020(0.6); 3.934(0.5); 3.322(19.4); 2.670(0.4); 2.510(22.8); 2.506(43.2); 2.501(55.0); 2.497(39.4); 2.493(18.8); 2.414(10.6); 2.352(0.7); 2.328(0.4); 1.989(2.2); 1.192(0.6); 1.175(1.2); 1.157(0.6); 0.008(1.5); 0.000(32.7); −0.009(1.1)

Example 139: ¹H-NMR (400.0 MHz, DMSO):

δ = 7.960(6.0); 7.647(2.2); 7.642(2.2); 7.442(1.6); 7.421(1.9); 7.235(1.5); 7.230(1.4); 7.215(1.2); 7.210(1.2); 5.757(0.6); 4.164(16.0); 4.146(0.5); 4.121(0.5); 4.107(0.9); 4.082(0.4); 4.056(0.9); 4.016(1.0); 4.003(0.5); 3.990(0.4); 3.977(0.5); 3.322(6.3); 2.524(0.9); 2.519(0.9); 2.511(10.2); 2.506(20.1); 2.502(26.2); 2.497(18.7); 2.493(8.8); 2.410(10.4); 2.074(1.5); 2.060(14.5); 0.000(5.6)

Example 140: ¹H-NMR (400.0 MHz, DMSO):

δ = 8.124(6.8); 8.103(7.0); 8.066(4.2); 8.050(6.3); 5.755(5.5); 4.244(0.4); 4.227(16.0); 4.219(1.4); 4.209(1.1); 4.194(1.2); 4.183(1.1); 4.169(0.5); 4.158(0.4); 4.030(0.4); 3.322(10.5); 2.525(0.4); 2.520(0.6); 2.511(7.8); 2.507(15.9); 2.502(20.8); 2.498(14.5); 2.493(6.7); 2.075(1.3); 0.000(6.9)

Example 141: ¹H-NMR (400.0 MHz, DMSO):

δ = 8.069(5.8); 8.059(4.2); 8.025(5.7); 5.757(0.3); 4.252(0.4); 4.242(0.4); 4.228(1.1); 4.210(1.3); 4.202(1.3); 4.182(16.0); 4.159(0.5); 3.323(27.3); 2.675(0.3); 2.671(0.4); 2.666(0.3); 2.510(28.9); 2.506(53.1); 2.502(66.5); 2.497(48.3); 2.493(24.3); 2.333(0.3); 2.329(0.4); 2.078(14.2); 0.008(2.1); 0.000(41.9); −0.009(2.1)

Example 142: ¹H-NMR (400.0 MHz, DMSO):

δ = 8.182(5.8); 8.081(5.4); 7.955(2.5); 7.949(2.7); 7.695(1.2); 7.689(1.1); 7.675(1.6); 7.669(1.6); 7.564(2.1); 7.544(1.6); 4.252(0.6); 4.242(0.5); 4.225(16.0); 4.188(0.7); 4.097(0.8); 4.070(0.9); 4.061(0.6); 4.043(0.4); 4.034(0.6); 3.321(12.4); 2.671(0.5); 2.506(49.1); 2.501(63.5); 2.497(47.7); 2.463(10.7); 2.328(0.4); 0.000(1.5)

Example 143: ¹H-NMR (601.6 MHz, DMSO):

δ = 8.280(4.2); 8.265(4.8); 8.187(5.5); 8.179(4.9); 8.129(4.9); 8.118(5.2); 8.111(4.6); 8.079(5.5); 4.507(0.5); 4.489(0.6); 4.482(0.6); 4.464(0.6); 4.296(0.4); 4.278(0.5); 4.271(0.8); 4.254(0.9); 4.226(13.9); 4.222(16.0); 4.213(1.3); 4.207(0.6); 4.195(0.4); 4.189(0.4); 4.156(0.6); 4.138(0.6); 4.131(0.5); 4.114(0.5); 3.321(71.6); 2.523(0.4); 2.520(0.6); 2.517(0.5); 2.508(15.0); 2.505(33.0); 2.502(46.3); 2.499(35.1); 2.496(17.9); 2.074(0.4); 0.000(8.9)

Example 144: ¹H-NMR (400.0 MHz, DMSO):

δ = 8.297(4.7); 8.286(5.7); 8.180(9.6); 8.011(8.8); 5.757(0.8); 4.503(0.7); 4.476(0.8); 4.466(0.9); 4.439(0.9); 4.393(0.5); 4.366(1.4); 4.363(1.3); 4.339(1.4); 4.336(1.4); 4.310(0.5); 4.182(16.0); 4.174(13.3); 4.133(0.8); 4.106(0.9); 4.096(0.7); 4.080(0.4); 4.069(0.7); 3.322(42.7); 2.675(0.5); 2.671(0.7); 2.666(0.5); 2.510(43.3); 2.506(82.5); 2.502(105.5); 2.497(76.0); 2.493(36.6); 2.333(0.5); 2.328(0.7); 2.324(0.5); 2.134(11.3); 2.068(14.5); 1.234(0.6); 0.000(1.6)

Example 145: ¹H-NMR (400.0 MHz, DMSO):

δ = 7.967(9.0); 7.869(1.5); 7.863(3.4); 7.858(2.7); 7.617(0.4); 7.612(0.4); 7.605(0.8); 7.597(1.6); 7.592(1.7); 7.584(4.4); 7.580(3.4); 7.573(3.6); 7.564(0.5); 7.552(0.7); 5.756(1.2); 5.264(0.4); 4.319(0.4); 4.309(0.5); 4.282(0.5); 4.248(0.8); 4.221(2.5); 4.194(2.7); 4.171(9.0); 4.160(16.0); 3.970(0.4); 3.958(0.4); 3.942(0.5); 3.932(0.4); 3.906(0.4); 3.321(34.4); 2.675(0.4); 2.670(0.6); 2.666(0.5); 2.510(37.9); 2.506(72.9); 2.501(95.0); 2.497(69.7); 2.492(34.8); 2.478(7.4); 2.465(12.3); 2.328(0.8); 2.324(0.5); 2.129(14.2); 2.044(7.8); 1.233(0.3); 0.008(2.5); 0.000(60.0); −0.009(2.5)

Example 146: ¹H-NMR (400.0 MHz, DMSO):

δ = 8.049(6.1); 7.840(2.0); 7.822(2.0); 7.497(1.8); 7.470(1.8); 5.756(1.3); 4.176(16.0); 4.078(0.4); 4.064(0.4); 4.053(0.5); 4.039(1.1); 4.028(0.5); 4.014(1.1); 4.002(1.1); 3.988(0.5); 3.976(1.1); 3.963(0.4); 3.951(0.4); 3.937(0.4); 3.321(15.9); 2.675(0.3); 2.671(0.5); 2.667(0.3); 2.524(1.9); 2.511(27.8); 2.506(54.0); 2.502(70.1); 2.497(50.8); 2.493(24.8); 2.469(0.6); 2.455(11.7); 2.433(0.9); 2.428(0.5); 2.409(1.1); 2.390(1.1); 2.372(0.4); 2.333(0.3); 2.329(0.5); 2.324(0.3); 2.257(1.0); 2.239(1.0); 2.221(1.1); 2.215(0.7); 2.197(0.7); 1.112(3.6); 1.094(7.6); 1.076(3.4); 0.000(1.9)

Example 147: ¹H-NMR (400.0 MHz, DMSO):

δ = 8.316(0.3); 8.070(2.3); 8.054(8.2); 8.052(8.0); 8.036(1.5); 8.017(1.4); 7.638(2.2); 7.612(2.2); 5.756(5.0); 4.370(0.7); 4.361(0.4); 4.343(0.8); 4.334(0.9); 4.316(0.4); 4.306(0.9); 4.279(0.6); 4.259(1.1); 4.253(1.0); 4.232(1.1); 4.226(1.1); 4.198(0.6); 4.182(16.0); 4.170(11.0); 4.018(0.8); 3.992(1.0); 3.982(0.8); 3.965(0.4); 3.955(0.7); 3.322(36.3); 2.763(0.4); 2.675(0.7); 2.671(0.9); 2.666(0.7); 2.613(0.6); 2.595(0.7); 2.570(0.8); 2.552(0.9); 2.506(109.4); 2.502(139.6); 2.498(100.3); 2.383(0.7); 2.365(0.8); 2.340(1.4); 2.333(0.8); 2.328(1.1); 2.322(1.8); 2.304(0.4); 2.272(0.5); 2.255(1.6); 2.237(1.7); 2.218(0.8); 2.212(1.1); 2.194(1.0); 2.176(0.3); 1.143(2.3); 1.125(4.8); 1.112(4.5); 1.094(7.7); 1.076(3.4); 0.000(58.1); −0.008(3.0)

Example 148: ¹H-NMR (400.0 MHz, DMSO):

δ = 8.164(5.3); 8.116(5.7); 8.056(2.2); 8.045(0.3); 8.037(2.2); 7.927(2.6); 7.903(2.6); 4.224(16.0); 4.195(0.6); 4.169(1.9); 4.160(0.7); 4.144(1.9); 4.118(0.7); 3.978(0.6); 3.323(16.1); 2.524(0.4); 2.511(9.2); 2.507(18.7); 2.502(24.7); 2.498(18.0); 2.493(8.8); 2.075(1.3); 0.008(0.8); 0.000(23.1); −0.008(0.9)

Example 149: ¹H-NMR (400.0 MHz, DMSO):

δ = 8.062(2.0); 8.043(2.0); 8.016(5.5); 7.945(2.5); 7.922(2.5); 5.756(0.7); 4.197(0.4); 4.177(16.0); 4.147(2.1); 4.121(1.4); 4.107(0.4); 4.095(0.4); 4.081(0.4); 3.322(13.4); 2.525(0.6); 2.511(13.7); 2.507(27.1); 2.502(35.4); 2.498(25.7); 2.493(12.5); 2.146(13.3); 0.000(2.9)

Example 150: ¹H-NMR (400.0 MHz, DMSO):

δ = 8.698(5.4); 8.104(2.1); 8.085(2.1); 7.979(2.5); 7.955(2.5); 4.292(16.0); 4.157(0.8); 4.131(2.5); 4.106(2.6); 4.081(0.9); 4.027(0.4); 3.323(14.2); 2.524(0.6); 2.511(13.4); 2.507(26.8); 2.502(35.5); 2.498(26.3); 2.493(13.2); 2.075(0.4); 0.000(2.8)

Example 151: ¹H-NMR (400.0 MHz, DMSO):

δ = 8.109(6.0); 8.058(6.5); 7.879(4.4); 7.669(3.7); 5.756(1.9); 4.223(16.0); 4.121(0.8); 4.095(2.4); 4.069(2.5); 4.044(0.9); 3.322(40.5); 2.671(0.3); 2.524(0.8); 2.511(19.6); 2.506(39.3); 2.502(51.4); 2.497(37.1); 2.493(18.0); 2.418(10.8); 2.329(0.3); 1.283(0.4); 0.876(0.7); 0.863(0.4); 0.857(0.4); 0.008(1.0); 0.000(28.9); −0.008(1.1)

Example 152: ¹H-NMR(400.0 MHz, DMSO):

δ = 8.005(5.9); 7.868(4.3); 7.681(3.7); 4.179(16.0); 4.157(0.4); 4.145(0.5); 4.131(1.0); 4.106(1.1); 4.084(1.1); 4.058(1.1); 4.044(0.4); 4.032(0.4); 4.019(0.4); 3.333(22.2); 2.671(0.3); 2.524(0.9); 2.511(19.8); 2.506(39.7); 2.502(52.2); 2.497(37.5); 2.493(17.9); 2.417(11.2); 2.328(0.3); 2.074(0.9); 2.054(14.6); 0.008(0.5); 0.000(14.2); −0.009(0.5)

Example 153: ¹H-NMR (400.0 MHz, DMSO):

δ = 8.685(4.9); 8.160(3.7); 8.005(0.5); 7.862(6.2); 7.682(0.3); 4.353(0.4); 4.290(16.0); 4.179(1.5); 4.107(0.4); 4.084(0.3); 3.322(61.0); 2.675(0.4); 2.671(0.5); 2.666(0.4); 2.524(1.3); 2.511(30.1); 2.506(60.5); 2.502(79.6); 2.497(57.7); 2.493(29.2); 2.486(16.9); 2.417(1.1); 2.333(0.4); 2.328(0.5); 2.324(0.4); 2.074(1.9); 2.054(1.4); 0.008(0.7); 0.000(19.9); −0.009(0.7)

Example 154: ¹H-NMR(400.0 MHz, DMSO):

δ = 8.695(5.6); 7.928(4.3); 7.707(3.7); 4.295(16.0); 4.083(0.8); 4.057(2.5); 4.031(2.6); 4.006(0.9); 3.322(43.6); 2.671(0.3); 2.524(0.9); 2.510(20.6); 2.506(41.6); 2.502(55.0); 2.497(39.9); 2.493(19.4); 2.453(11.2); 2.328(0.4); 2.074(0.6); 0.000(5.2)

Example 155: ¹H-NMR (400.0 MHz, DMSO):

δ = 8.315(0.4); 8.199(2.4); 8.195(2.0); 8.179(2.5); 8.175(1.9); 8.144(1.8); 8.138(2.4); 8.121(2.4); 8.005(8.7); 5.755(4.1); 4.480(0.6); 4.453(0.7); 4.443(0.8); 4.416(0.8); 4.389(0.4); 4.351(1.0); 4.345(1.0); 4.324(1.0); 4.318(1.0); 4.297(0.4); 4.291(0.4); 4.179(16.0); 4.170(12.3); 4.154(0.6); 4.123(0.8); 4.116(0.6); 4.097(0.9); 4.086(0.7); 4.070(0.4); 4.060(0.7); 3.321(62.9); 2.676(0.5); 2.671(0.7); 2.666(0.5); 2.541(0.4); 2.524(1.6); 2.520(2.4); 2.511(37.6); 2.506(77.9); 2.502(103.8); 2.497(74.2); 2.493(34.9); 2.333(0.5); 2.329(0.7); 2.324(0.5); 2.196(9.1); 2.136(12.7); 1.234(0.7); 0.146(0.4); 0.008(3.1); 0.000(100.6); −0.009(3.3); −0.150(0.4)

Example 156: ¹H-NMR (400.0 MHz, DMSO):

δ = 8.201(5.0); 8.191(2.4); 8.172(2.4); 8.121(2.1); 8.113(5.8); 8.097(1.9); 4.224(16.0); 4.196(0.4); 3.325(33.1); 2.511(15.2); 2.507(29.9); 2.502(39.0); 2.498(28.6); 1.284(0.3); 0.876(0.5); 0.863(0.3); 0.008(2.0); 0.000(45.0); −0.008(2.0)

Example 157: ¹H-NMR (400.0 MHz, DMSO):

δ = 8.082(5.3); 8.064(3.8); 8.004(8.6); 7.859(3.8); 7.853(2.9); 5.756(9.7); 4.397(0.6); 4.370(0.7); 4.360(0.8); 4.333(0.8); 4.301(0.5); 4.273(1.6); 4.246(1.7); 4.219(0.6); 4.182(16.0); 4.171(11.8); 4.020(0.7); 3.993(0.9); 3.983(0.7); 3.966(0.3); 3.956(0.7); 3.322(46.3); 2.676(0.4); 2.671(0.6);

-continued 2.666(0.4); 2.541(0.4); 2.524(1.4); 2.519(2.1); 2.511(30.9); 2.506(63.1); 2.502(83.3); 2.497(59.3); 2.493(28.9); 2.488(13.2); 2.476(8.3); 2.425(0.4); 2.333(0.4); 2.329(0.6); 2.324(0.5); 2.135(10.3); 2.054(0.4); 2.040(14.9); 1.234(0.5); 1.187(0.4); 0.008(1.8); 0.000(59.9); −0.009(2.0)
Example 158: $^1$H-NMR (400.0 MHz, DMSO):

δ = 8.113(9.0); 8.110(5.5); 8.087(13.9); 7.845(2.4); 7.823(3.2); 5.756(3.2); 4.398(0.4); 4.370(0.5); 4.360(0.6); 4.333(0.6); 4.235(0.7); 4.226(12.2); 4.219(16.0); 4.209(0.7); 4.199(1.0); 4.180(0.4); 4.172(1.0); 4.152(0.9); 4.145(0.4); 4.125(1.0); 4.116(0.4); 4.098(0.4); 4.089(0.4); 4.044(0.6); 4.038(0.5); 4.017(0.6); 4.007(0.5); 3.980(0.5); 3.325(89.2); 2.675(0.4); 2.671(0.5); 2.666(0.4); 2.524(1.4); 2.511(29.8); 2.506(60.9); 2.502(80.9); 2.497(58.4); 2.493(27.9); 2.478(15.9); 2.333(0.4); 2.329(0.6); 2.324(0.4); 0.008(1.4); 0.000(43.6); −0.009(1.5)
Example 159: $^1$H-NMR (400.0 MHz, DMSO):

δ = 8.154(7.0); 8.121(7.1); 7.871(2.9); 7.853(2.9); 7.483(2.5); 7.456(2.5); 4.621(1.2); 4.603(3.8); 4.585(3.8); 4.567(1.3); 4.054(1.1); 4.028(3.5); 4.002(3.6); 3.976(1.2); 3.330(21.3); 2.671(0.3); 2.507(43.3); 2.502(53.8); 2.498(38.8); 2.456(16.0); 2.329(0.4); 1.426(5.0); 1.408(10.7); 1.390(4.9); 1.101(0.4); 0.146(0.4); 0.000(75.0); −0.008(3.6); −0.150(0.4)
Example 160: $^1$H-NMR (400.0 MHz, DMSO):

δ = 8.015(7.2); 7.870(2.3); 7.851(2.3); 7.499(2.0); 7.472(2.0); 4.571(0.9); 4.556(2.4); 4.553(2.4); 4.537(2.5); 4.534(2.5); 4.519(0.9); 4.092(0.6); 4.078(0.4); 4.067(0.7); 4.053(1.2); 4.042(0.3); 4.027(1.3); 3.999(1.3); 3.973(1.3); 3.959(0.6); 3.947(0.5); 3.933(0.6); 3.323(38.3); 2.676(0.4); 2.671(0.6); 2.667(0.4); 2.524(1.5); 2.511(34.9); 2.506(69.6); 2.502(90.8); 2.497(64.6); 2.493(30.9); 2.456(13.2); 2.333(0.5); 2.329(0.6); 2.324(0.5); 2.121(16.0); 2.111(0.9); 1.401(4.5); 1.383(10.0); 1.365(4.4); 1.353(0.3); 1.336(0.8); 1.234(0.5); 1.192(0.5); 1.174(0.4); 0.146(0.8); 0.008(8.5); 0.000(190.8); −0.009(6.9); −0.150(0.9)
Example 161: $^1$H-NMR (400.0 MHz, DMSO):

δ = 8.152(6.9); 8.131(6.9); 7.872(2.8); 7.854(2.8); 7.482(2.3); 7.455(2.3); 5.407(0.5); 5.391(1.2); 5.374(1.7); 5.357(1.2); 5.341(0.5); 4.053(1.0); 4.027(3.1); 4.001(3.2); 3.975(1.1); 3.327(27.6); 2.525(0.6); 2.512(12.0); 2.508(23.9); 2.503(31.0); 2.499(22.0); 2.494(10.3); 2.457(14.8); 2.416(0.4); 1.491(16.0); 1.474(15.7); 1.453(0.7); 1.437(0.7); 0.008(0.6); 0.000(16.1); −0.009(0.5)
Example 162: $^1$H-NMR (400.0 MHz, DMSO):

δ = 8.024(6.6); 7.873(2.4); 7.854(2.4); 7.498(2.1); 7.472(2.1); 5.340(0.4); 5.323(1.1); 5.307(1.5); 5.290(1.1); 5.273(0.4); 4.094(0.5); 4.080(0.4); 4.069(0.6); 4.055(1.2); 4.030(1.3); 4.004(0.6); 3.998(1.2); 3.972(1.3); 3.959(0.6); 3.946(0.5); 3.933(0.6); 3.326(55.6); 2.525(0.7); 2.512(16.6); 2.507(33.2); 2.503(43.2); 2.498(30.4); 2.494(14.3); 2.456(13.5); 2.118(16.0); 2.075(0.5); 1.476(7.9); 1.462(10.9); 1.446(7.9); 0.008(0.6); 0.000(17.5); −0.009(0.6)
Example 163: $^1$H-NMR (400.0 MHz, DMSO):

δ = 8.316(0.5); 8.212(6.7); 8.125(12.8); 8.117(0.3); 8.101(4.3); 8.083(4.3); 7.608(2.8); 7.581(2.7); 5.756(1.3); 4.622(1.6); 4.604(5.0); 4.586(5.0); 4.569(1.6); 4.240(0.5); 4.147(0.4); 4.110(0.5); 3.323(99.9); 2.675(0.8); 2.671(1.1); 2.666(0.8); 2.541(0.6); 2.511(65.1); 2.506(126.8); 2.502(164.5); 2.497(118.1); 2.492(63.8); 2.333(0.8); 2.328(1.2); 2.324(0.8); 1.429(7.2); 1.411(16.0); 1.393(7.1); 1.233(0.4); 0.008(2.7); 0.000(65.1); −0.009(2.3)
Example 164: $^1$H-NMR (400.0 MHz, DMSO):

δ = 8.096(2.7); 8.085(2.2); 8.077(2.8); 8.067(1.9); 8.017(8.9); 7.642(2.5); 7.636(1.9); 7.616(2.5); 7.609(1.8); 4.580(1.0); 4.563(2.9); 4.559(2.7); 4.546(3.6); 4.541(2.9); 4.529(2.4); 4.513(0.8); 4.371(0.8); 4.362(0.4); 4.344(1.0); 4.334(1.1); 4.317(0.7); 4.307(1.1); 4.283(0.8); 4.257(2.1); 4.230(2.1); 4.203(0.7); 4.025(1.0); 4.015(0.4); 3.998(1.1); 3.988(0.9); 3.972(0.4); 3.962(0.8); 3.325(132.0); 2.671(0.8); 2.506(104.9); 2.502(133.4); 2.408(0.4); 2.397(0.3); 2.333(0.7); 2.329(0.9); 2.196(10.6); 2.110(16.0); 1.413(4.5); 1.404(3.9); 1.395(9.7); 1.386(7.1); 1.377(4.8); 1.368(3.2); 0.000(43.7)
Example 165: $^1$H-NMR (400.0 MHz, DMSO):

δ = 8.316(0.4); 8.210(7.4); 8.136(11.7); 8.100(4.7); 8.082(4.8); 7.607(3.1); 7.581(3.0); 5.407(0.8); 5.390(2.0); 5.373(2.8); 5.357(2.0); 5.340(0.8); 4.241(0.6); 4.216(0.7); 4.209(1.2); 4.132(0.6); 4.126(0.6); 3.326(210.4); 2.676(0.8); 2.671(1.1); 2.667(0.8); 2.541(0.7); 2.524(3.0); 2.511(67.2); 2.506(132.3); 2.502(172.2); 2.497(124.9); 2.493(68.2); 2.367(0.7); 2.358(0.3); 2.333(0.8); 2.329(1.2); 2.324(0.9); 1.496(15.8); 1.491(13.8); 1.480(16.0); 1.475(13.4); 1.459(1.3); 1.443(1.0); 1.008(0.4); 0.007(2.8); 0.000(67.8); −0.008(2.3)

Example 166: $^1$H-NMR (400.0 MHz, DMSO):

δ = 8.316(0.3); 8.094(2.7); 8.087(2.1); 8.075(2.8); 8.068(2.0); 8.026(7.8); 7.641(2.2); 7.634(1.8); 7.615(2.3); 7.608(1.7); 5.348(0.5); 5.332(1.4); 5.315(2.3); 5.299(2.2); 5.282(1.2); 5.266(0.4); 4.373(0.8); 4.363(0.4); 4.345(0.9); 4.336(1.0); 4.318(0.4); 4.309(1.0); 4.283(0.8); 4.257(2.0); 4.230(2.1); 4.203(0.7); 4.029(0.9); 4.020(0.3); 4.003(1.1); 3.993(0.8); 3.976(0.4); 3.966(0.8); 3.325(139.4); 2.763(0.4); 2.675(0.7); 2.671(1.0); 2.667(0.7); 2.541(0.5); 2.511(59.8); 2.506(120.2); 2.502(164.1); 2.498(116.3); 2.493(61.4); 2.333(0.8); 2.329(1.1); 2.324(0.9); 2.193(10.8); 2.107(16.0); 1.481(9.0); 1.475(9.2); 1.472(11.1); 1.462(12.8); 1.455(11.0); 1.445(6.2); 1.245(0.4); 1.234(0.7); 0.146(0.6); 0.008(6.1); 0.000(136.7); −0.008(6.1); −0.150(0.6)
Example 167: $^1$H-NMR (400.0 MHz, DMSO):

δ = 8.168(7.4); 8.140(8.2); 7.880(2.9); 7.862(2.9); 7.480(2.5); 7.453(2.5); 4.441(2.2); 4.424(2.2); 4.057(1.1); 4.031(3.4); 4.005(3.5); 3.979(1.2); 3.324(66.6); 2.676(0.4); 2.671(0.5); 2.667(0.4); 2.524(1.5); 2.511(32.4); 2.506(64.4); 2.502(84.2); 2.498(61.5); 2.454(16.0); 2.333(0.4); 2.329(0.6); 2.324(0.4); 1.333(0.4); 1.321(0.7); 1.313(0.7); 1.302(1.1); 1.290(0.7); 1.282(0.8); 1.271(0.4); 0.503(0.7); 0.488(2.6); 0.478(1.8); 0.468(2.4); 0.458(1.4); 0.444(0.6); 0.422(1.3); 0.411(3.2); 0.401(2.9); 0.385(0.6); 0.146(0.5); 0.008(5.0); 0.000(119.5); −0.008(5.1); −0.150(0.6)
Example 168: $^1$H-NMR (400.0 MHz, DMSO):

δ = 8.034(5.6); 7.881(2.7); 7.863(2.6); 7.497(2.5); 7.471(2.4); 4.438(0.6); 4.420(0.8); 4.403(2.4); 4.385(4.3); 4.367(2.4); 4.350(0.8); 4.332(0.6); 4.093(0.7); 4.078(0.7); 4.067(0.9); 4.053(1.5); 4.028(1.8); 4.002(1.8); 3.977(1.5); 3.963(0.8); 3.950(0.7); 3.937(0.6); 3.325(55.5); 2.672(0.7); 2.502(104.6); 2.453(16.0); 2.329(0.8); 2.131(15.9); 1.398(1.6); 1.276(1.4); 1.265(1.1); 1.258(1.0); 0.471(3.5); 0.451(3.3); 0.380(4.5); 0.371(4.1); 0.146(0.4); 0.000(86.0); −0.150(0.5)
Example 169: $^1$H-NMR (400.0 MHz, DMSO):

δ = 8.316(0.5); 8.274(0.4); 8.256(0.5); 8.232(7.8); 8.187(0.9); 8.147(16.0); 8.138(1.4); 8.112(5.8); 8.093(5.8); 7.606(4.1); 7.579(4.0); 5.757(1.2); 4.987(0.4); 4.962(0.4); 4.446(5.4); 4.428(5.4); 4.240(0.9); 4.179(0.7); 4.134(0.9); 4.121(0.8); 3.327(286.2); 2.755(1.9); 2.675(1.2); 2.671(1.6); 2.667(1.2); 2.541(2.1); 2.506(191.7); 2.502(242.7); 2.498(179.4); 2.367(0.4); 2.333(1.2); 2.329(1.7); 1.341(0.8); 1.329(1.5); 1.323(1.5); 1.310(2.4); 1.299(1.6); 1.291(1.7); 1.280(1.0); 1.261(0.4); 1.245(0.4); 1.234(0.7); 0.506(1.4); 0.490(5.9); 0.481(4.0); 0.471(5.3); 0.461(3.1); 0.447(1.3); 0.426(3.0); 0.414(7.1); 0.405(6.4); 0.388(1.4); 0.000(62.9); −0.008(3.6)
Example 170: $^1$H-NMR (400.0 MHz, DMSO):

δ = 8.316(0.5); 8.103(2.8); 8.098(2.4); 8.085(2.9); 8.079(2.2); 8.035(11.5); 7.640(2.4); 7.635(2.1); 7.613(2.5); 4.454(0.8); 4.436(0.9); 4.419(1.9); 4.401(2.3); 4.378(4.3); 4.369(1.3); 4.360(3.6); 4.342(1.9); 4.332(1.2); 4.325(1.3); 4.314(0.5); 4.305(1.1); 4.282(0.7); 4.256(1.7); 4.229(1.8); 4.201(0.7); 4.049(0.3); 4.022(1.0); 4.012(0.4); 3.996(1.1); 3.986(0.9); 3.969(0.4); 3.959(0.9); 3.326(247.6); 2.762(0.7); 2.675(0.9); 2.671(1.2); 2.667(1.0); 2.541(1.0); 2.506(147.5); 2.502(201.7); 2.498(145.0); 2.333(0.9); 2.329(1.3); 2.324(1.0); 2.204(11.5); 2.118(16.0); 1.317(0.6); 1.304(1.1); 1.299(1.4); 1.291(1.4); 1.287(1.4); 1.280(1.1); 1.274(1.2); 1.261(0.9); 1.235(0.7); 0.494(1.8); 0.486(1.5); 0.474(3.6); 0.467(2.6); 0.458(3.0); 0.452(2.5); 0.431(0.6); 0.413(0.6); 0.386(3.8); 0.380(4.1); 0.374(3.8); 0.367(2.5); 0.353(0.7); 0.007(1.9); 0.000(45.0)
Example 171: $^1$H-NMR (601.6 MHz, DMSO):

δ = 8.314(0.6); 8.122(5.4); 7.789(2.1); 7.777(2.1); 7.427(1.8); 7.410(1.7); 4.038(0.8); 4.021(2.4); 4.003(2.4); 3.986(0.9); 3.907(13.9); 3.717(1.2); 3.319(167.4); 2.610(16.0); 2.541(0.4); 2.522(1.9); 2.519(2.4); 2.516(2.4); 2.507(75.8); 2.504(165.3); 2.501(230.6); 2.498(169.0); 2.495(81.9); 2.440(12.7); 2.399(0.5); 2.389(1.2); 2.385(1.6); 2.383(1.2); 0.005(1.1); 0.000(42.2); −0.006(1.8)
Example 172: $^1$H-NMR (400.0 MHz, DMSO):

δ = 8.315(0.6); 8.197(4.2); 8.013(2.4); 7.994(2.4); 7.563(1.8); 7.536(1.7); 5.756(0.5); 4.222(0.4); 4.196(0.4); 4.144(0.4); 4.116(0.4); 4.032(0.4); 3.913(14.4); 3.726(1.2); 3.320(106.0); 2.675(1.1); 2.670(1.5); 2.666(1.1); 2.661(0.6); 2.615(16.0); 2.541(0.9); 2.524(3.8); 2.510(83.2); 2.506(167.9); 2.501(222.6); 2.497(161.7); 2.492(78.5); 2.475(13.6); 2.454(1.5); 2.355(0.4); 2.337(0.6); 2.333(1.2); 2.328(1.6); 2.324(1.2); 2.242(0.8); 1.235(0.8); 0.008(0.5); 0.000(16.2); −0.009(0.6)
Example 173: $^1$H-NMR (400.0 MHz, DMSO):

δ = 8.635(5.6); 8.199(6.6); 7.818(2.6); 7.799(2.6); 7.441(2.2); 7.415(2.2); 4.048(16.0); 4.030(3.4); 4.004(3.4); 3.978(1.2); 3.325(30.4); 2.525(0.8);

2.511(16.0); 2.507(31.8); 2.502(41.6); 2.498(30.2); 2.493(14.6); 2.440(13.9); 0.008(0.4); 0.000(11.1); −0.009(0.4)
Example 174: ¹H-NMR (400.0 MHz, DMSO):

δ = 8.560(5.4); 7.812(2.4); 7.793(2.4); 7.455(2.1); 7.428(2.1); 4.095(0.5); 4.082(0.4); 4.070(0.6); 4.056(1.2); 4.048(0.6); 4.030(1.6); 4.018(15.0); 4.005(0.8); 3.997(1.2); 3.971(1.2); 3.957(0.6); 3.945(0.5); 3.931(0.6); 3.654(0.7); 3.324(39.8); 2.675(0.3); 2.671(0.5); 2.666(0.3); 2.511(29.0); 2.506(56.4); 2.502(72.5); 2.497(51.3); 2.493(24.2); 2.441(13.5); 2.394(0.8); 2.333(0.4); 2.329(0.5); 2.324(0.4); 2.111(16.0); 0.008(0.6); 0.000(16.1); −0.009(0.6)
Example 175: ¹H-NMR (400.0 MHz, DMSO):

δ = 8.578(3.2); 8.568(4.2); 8.315(0.4); 8.025(2.1); 8.018(1.6); 8.006(2.1); 7.999(1.4); 7.599(1.7); 7.593(1.3); 7.573(1.7); 7.567(1.2); 5.756(1.3); 4.366(0.6); 4.339(0.7); 4.330(0.7); 4.302(0.7); 4.277(0.6); 4.250(1.5); 4.223(1.6); 4.196(0.6); 4.052(0.6); 4.023(16.0); 3.998(0.8); 3.988(0.7); 3.971(0.3); 3.961(0.6); 3.323(93.5); 3.301(0.4); 2.675(0.6); 2.671(0.8); 2.666(0.6); 2.541(0.7); 2.506(99.4); 2.502(124.5); 2.497(87.9); 2.476(8.0); 2.333(0.6); 2.328(0.8); 2.324(0.6); 2.188(8.1); 2.102(11.7); 0.008(1.3); 0.000(26.8); −0.008(0.9)
Example 176: ¹H-NMR (400.0 MHz, DMSO):

δ = 8.400(8.9); 8.314(0.4); 8.192(10.9); 7.842(3.0); 7.824(3.1); 7.461(2.5); 7.433(2.5); 4.405(1.3); 4.386(4.0); 4.368(4.1); 4.350(1.3); 4.046(1.2); 4.020(4.0); 3.994(4.2); 3.969(1.4); 3.318(28.2); 2.675(0.4); 2.671(0.6); 2.666(0.4); 2.541(0.4); 2.524(1.7); 2.519(2.6); 2.511(32.7); 2.506(66.8); 2.502(90.5); 2.497(65.9); 2.492(31.0); 2.445(16.0); 2.333(0.4); 2.328(0.6); 2.324(0.4); 1.446(5.9); 1.427(13.6); 1.409(5.8); 0.146(0.4); 0.008(3.2); 0.000(91.6); −0.009(2.8); −0.150(0.3)
Example 177: ¹H-NMR (400.0 MHz, DMSO):

δ = 8.652(5.7); 8.269(4.6); 8.042(2.8); 8.024(2.7); 7.569(2.0); 7.543(2.0); 5.757(0.4); 4.227(0.5); 4.200(0.4); 4.145(0.4); 4.136(0.4); 4.119(0.8); 4.053(16.0); 3.356(0.3); 3.327(113.2); 2.675(0.4); 2.671(0.5); 2.667(0.4); 2.511(32.7); 2.506(63.3); 2.502(82.6); 2.498(61.5); 2.476(14.6); 2.416(0.3); 2.333(0.4); 2.329(0.6); 2.325(0.4); 0.000(6.5)
Example 178: ¹H-NMR (400.0 MHz, DMSO):

δ = 8.319(4.6); 8.284(5.0); 8.252(0.4); 8.048(2.5); 8.030(2.5); 7.755(0.4); 7.598(1.7); 7.572(1.7); 6.772(0.4); 4.237(0.4); 4.210(0.4); 4.174(0.4); 4.162(0.4); 4.147(0.5); 4.112(0.5); 4.098(0.4); 3.987(16.0); 3.804(1.0); 3.784(1.1); 3.506(0.9); 3.332(106.6); 2.676(0.4); 2.672(0.5); 2.667(0.4); 2.542(0.5); 2.507(58.6); 2.502(75.2); 2.498(55.5); 2.488(15.5); 2.452(0.7); 2.364(1.2); 2.345(1.0); 2.333(0.5); 2.329(0.6); 2.325(0.5); 1.234(1.3); 0.008(3.2); 0.000(60.0); −0.008(2.7)
Example 179: ¹H-NMR(601. MHz, CD3CN):

δ = 8.110(2.4); 8.029(1.9); 8.017(1.9); 7.847(3.5); 7.360(1.4); 7.343(1.4); 7.108(0.4); 7.088(0.4); 3.788(16.0); 3.744(2.3); 3.650(0.5); 3.633(0.6); 3.626(0.4); 3.608(0.4); 3.535(0.9); 3.519(0.9); 3.502(0.3); 2.471(10.8); 2.418(0.6); 2.409(2.8); 2.132(54.2); 2.050(0.4); 1.963(3.5); 1.955(5.2); 1.951(5.8); 1.947(29.7); 1.943(49.6); 1.939(71.0); 1.935(49.6); 1.931(25.2); 1.922(0.3); 1.824(0.4); 1.372(0.8); 1.285(0.4); 1.277(1.0); 0.000(5.6)
Example 180: ¹H-NMR (400.0 MHz, DMSO):

δ = 8.566(5.0); 7.916(1.9); 7.898(1.9); 7.514(1.6); 7.487(1.6); 4.045(0.8); 4.019(2.6); 3.994(2.7); 3.968(0.9); 3.322(19.4); 2.669(16.0); 2.524(0.5); 2.520(0.8); 2.511(14.0); 2.506(29.4); 2.502(39.2); 2.497(28.2); 2.493(13.6); 2.462(10.6); 1.128(1.0); 1.111(0.6); 1.093(0.3); 0.000(8.5)
Example 181: ¹H-NMR (601.6 MHz, DMSO):

δ = 8.604(5.3); 8.177(1.5); 8.165(1.5); 7.628(0.9); 7.610(0.9); 3.319(61.9); 2.672(16.0); 2.616(0.4); 2.613(0.6); 2.610(0.4); 2.522(0.9); 2.519(1.2); 2.516(1.1); 2.507(28.8); 2.504(64.3); 2.501(91.7); 2.498(65.5); 2.495(31.2); 2.493(12.8); 2.389(0.5); 2.385(0.7); 2.382(0.5); 1.988(0.5); 1.398(1.3); 0.005(0.6); 0.000(23.2); −0.006(0.8)
Example 182: ¹H-NMR(400.0 MHz, DMSO):

δ = 8.315(0.6); 8.232(0.8); 8.214(0.8); 7.951(1.3); 7.933(1.3); 7.683(0.6); 7.657(0.7); 7.568(1.2); 7.541(1.2); 4.344(0.3); 4.022(0.3); 3.999(0.6); 3.985(0.4); 3.973(1.8); 3.948(1.9); 3.922(0.6); 3.321(174.4); 2.873(16.0); 2.675(1.5); 2.670(2.0); 2.666(1.5); 2.541(1.3); 2.506(228.8); 2.501(300.6); 2.497(225.8); 2.333(1.4); 2.328(1.9); 2.324(1.4); 0.008(2.9); 0.000(68.7); −0.008(3.3)

Example 183: ¹H-NMR(400.0 MHz, DMSO):

δ = 8.232(2.1); 8.214(2.1); 7.684(1.7); 7.657(1.6); 4.381(0.6); 4.354(0.7); 4.344(0.8); 4.317(0.8); 4.050(0.7); 4.023(0.8); 4.012(0.7); 3.986(0.7); 3.339(0.3); 3.321(102.8); 2.873(16.0); 2.675(0.6); 2.671(0.9); 2.666(0.6); 2.541(0.5); 2.524(2.1); 2.519(3.2); 2.510(47.6); 2.506(97.3); 2.502(130.2); 2.497(100.3); 2.493(44.6); 2.333(0.6); 2.328(0.8); 2.324(0.6); 0.008(1.0); 0.000(31.6); −0.009(1.0)
Example 184: ¹H-NMR(400.0 MHz, DMSO):

δ = 8.316(0.3); 7.876(2.1); 7.858(2.1); 7.512(1.8); 7.486(1.9); 5.756(0.3); 4.074(0.4); 4.060(0.4); 4.048(0.5); 4.034(1.1); 4.023(0.5); 4.009(1.2); 3.998(1.1); 3.984(0.5); 3.972(1.2); 3.959(0.4); 3.946(0.4); 3.933(0.4); 3.321(108.1); 2.753(16.0); 2.679(0.4); 2.675(0.9); 2.670(1.3); 2.666(0.9); 2.661(0.4); 2.524(3.5); 2.519(5.5); 2.510(70.1); 2.506(142.1); 2.501(189.6); 2.497(137.8); 2.492(65.4); 2.455(12.1); 2.393(0.9); 2.337(0.5); 2.333(1.0); 2.328(1.3); 2.324(0.9); 2.319(0.4); 2.210(1.1); 2.195(14.9); 0.008(2.5); 0.000(78.7); −0.009(2.4); −0.150(0.3)
Example 185: ¹H-NMR(400.0 MHz, DMSO):

δ = 8.315(0.5); 8.139(1.8); 8.133(1.2); 8.120(1.9); 8.114(1.1); 7.903(0.3); 7.648(1.3); 7.641(0.9); 7.622(1.3); 7.615(0.8); 7.547(0.3); 5.755(1.6); 4.396(0.5); 4.368(0.6); 4.359(0.6); 4.331(0.6); 4.249(0.6); 4.231(0.6); 4.221(0.6); 4.204(0.6); 4.194(0.3); 3.993(0.6); 3.966(0.7); 3.956(0.6); 3.930(0.6); 3.323(236.8); 2.756(16.0); 2.680(0.4); 2.675(0.9); 2.671(1.2); 2.666(0.4); 2.662(0.4); 2.524(3.3); 2.519(5.1); 2.511(63.0); 2.506(127.3); 2.502(169.6); 2.497(128.6); 2.493(59.1); 2.338(0.5); 2.333(0.9); 2.328(1.2); 2.324(0.9); 2.319(0.4); 2.267(6.5); 2.181(11.0); 1.234(0.6); 0.000(4.6)
Example 186: ¹H-NMR(400.0 MHz, DMSO):

δ = 7.854(1.7); 7.848(2.8); 7.492(1.8); 7.481(1.2); 5.756(6.2); 4.319(0.4); 4.291(0.4); 4.282(0.5); 4.255(0.5); 4.228(0.4); 4.202(0.9); 4.175(0.9); 4.147(0.3); 3.953(0.4); 3.926(0.5); 3.916(0.4); 3.889(0.4); 3.322(77.2); 2.751(12.8); 2.675(0.5); 2.671(0.8); 2.666(0.5); 2.524(1.5); 2.519(2.3); 2.511(34.5); 2.506(70.7); 2.502(94.9); 2.497(69.2); 2.492(33.2); 2.449(6.1); 2.435(4.1); 2.333(0.5); 2.328(0.7); 2.324(0.5); 2.171(5.2); 2.077(16.0); 1.234(0.4); 0.000(2.4)
Example 187: ¹H-NMR(400.0 MHz, DMSO):

δ = 9.702(6.7); 8.316(0.4); 7.909(2.3); 7.890(2.3); 7.522(2.1); 7.496(2.1); 5.756(0.7); 4.071(0.4); 4.057(0.4); 4.046(0.5); 4.032(1.3); 4.024(0.7); 4.007(1.4); 3.981(0.6); 3.972(1.4); 3.959(0.5); 3.946(0.5); 3.933(0.4); 3.321(60.1); 2.675(0.8); 2.671(1.1); 2.666(0.9); 2.510(66.7); 2.506(131.9); 2.502(173.7); 2.497(129.5); 2.458(13.8); 2.369(0.4); 2.333(0.8); 2.328(1.1); 2.324(0.8); 2.251(16.0); 0.000(2.9)
Example 188: ¹H-NMR(400.0 MHz, DMSO):

δ = 9.702(4.7); 9.697(3.2); 8.170(1.9); 8.156(1.4); 8.151(2.1); 8.138(1.2); 7.661(1.5); 7.652(1.0); 7.634(1.5); 7.625(1.0); 4.394(0.5); 4.367(0.6); 4.357(0.7); 4.330(0.6); 4.257(0.7); 4.248(0.7); 4.230(0.7); 4.221(0.7); 3.979(0.6); 3.952(0.7); 3.942(0.6); 3.915(0.6); 3.325(34.2); 2.671(0.4); 2.541(0.3); 2.511(26.6); 2.507(51.4); 2.502(70.2); 2.498(52.2); 2.326(7.6); 2.242(11.4); 2.086(16.0); 0.008(1.7); 0.000(38.9); −0.007(1.3); −0.009(1.3)
Example 189: ¹H-NMR(400.0 MHz, DMSO):

δ = 8.712(0.5); 8.559(6.1); 7.901(2.3); 7.883(2.3); 7.491(2.1); 7.464(1.9); 5.756(0.4); 4.051(1.0); 4.025(3.2); 4.020(2.0); 3.999(3.2); 3.973(1.1); 3.321(27.9); 2.871(16.0); 2.675(0.4); 2.671(0.6); 2.666(0.4); 2.541(0.4); 2.510(33.1); 2.506(66.0); 2.501(87.3); 2.497(63.5); 2.493(31.4); 2.478(2.1); 2.463(1.8); 2.454(12.4); 2.328(1.1); 1.398(1.1); 0.146(0.3); 0.008(2.8); 0.000(71.8); −0.009(3.0)
Example 190: ¹H-NMR(400.0 MHz, DMSO):

δ = 8.749(0.5); 8.607(6.1); 8.315(0.5); 8.152(2.6); 8.133(2.5); 7.613(2.0); 7.587(1.9); 5.756(2.0); 4.284(0.4); 4.256(0.6); 4.252(0.6); 4.226(0.5); 4.110(0.4); 4.083(0.6); 4.074(0.4); 4.056(0.4); 4.020(1.4); 3.320(115.7); 3.294(0.4); 2.874(16.0); 2.743(0.4); 2.671(1.7); 2.567(0.6); 2.540(1.9); 2.506(212.4); 2.501(260.9); 2.497(189.5); 2.449(0.4); 2.328(1.7); 2.324(1.3); 1.236(0.6); 0.146(1.5); 0.008(22.8); 0.000(322.8); −0.008(13.8); −0.022(0.8); −0.025(0.8); −0.149(1.4)
Example 191: ¹H-NMR(400.0 MHz, DMSO):

δ = 8.402(3.0); 7.879(1.0); 7.860(1.0); 7.471(0.9); 7.444(0.9); 4.050(0.4); 4.024(1.2); 3.998(1.2); 3.972(0.4); 3.322(51.4); 2.675(0.4); 2.670(0.6); 2.666(0.4); 2.524(2.2); 2.510(35.8); 2.506(70.0); 2.502(91.0); 2.497(65.3); 2.492(31.3); 2.454(5.7); 2.333(0.4); 2.328(0.6); 2.324(0.4); 1.567(16.0); 1.398(5.6); 0.000(2.5)

-continued

Example 192: ¹H-NMR(400.0 MHz, DMSO):

δ = 8.453(1.0); 8.136(1.0); 8.118(1.0); 7.590(0.6); 7.563(0.6); 3.323(20.7); 2.524(0.8); 2.511(16.5); 2.506(32.8); 2.502(42.8); 2.497(30.9); 2.493(15.4); 2.488(7.3); 2.391(0.4); 1.572(16.0); 0.000(1.0)

Example 193: ¹H-NMR(400.0 MHz, DMSO):

δ = 9.842(0.4); 8.757(5.8); 7.886(2.2); 7.868(2.2); 7.497(2.0); 7.470(2.0); 7.104(0.5); 4.033(0.9); 4.008(2.9); 3.982(3.0); 3.956(1.1); 3.798(0.4); 3.772(0.4); 3.324(83.1); 3.308(1.5); 3.290(1.6); 3.273(1.2); 3.256(0.5); 2.675(0.5); 2.671(0.7); 2.666(0.5); 2.541(0.4); 2.506(86.7); 2.502(111.3); 2.497(81.1); 2.460(12.6); 2.445(0.8); 2.421(0.4); 2.403(0.4); 2.392(0.5); 2.333(0.7); 2.329(0.8); 2.324(0.6); 2.281(1.5); 1.398(1.1); 1.359(16.0); 1.342(15.8); 0.146(0.8); 0.008(9.0); 0.000(159.3); −0.008(7.4); −0.024(0.4); −0.150(0.8)

Example 194: ¹H-NMR(400.0 MHz, DMSO):

δ = 8.734(7.8); 8.315(0.6); 7.875(2.9); 7.857(2.9); 7.497(2.4); 7.470(2.4); 4.028(1.2); 4.002(3.8); 3.977(4.0); 3.951(1.3); 3.319(25.6); 2.679(0.4); 2.675(0.8); 2.671(1.2); 2.666(0.8); 2.662(0.4); 2.541(0.7); 2.524(3.1); 2.510(88.5); 2.506(135.2); 2.501(173.9); 2.497(123.1); 2.492(57.5); 2.459(16.0); 2.391(0.4); 2.337(0.4); 2.333(0.9); 2.328(1.2); 2.324(0.8); 2.319(0.4); 1.989(0.5); 1.398(2.2); 0.146(0.5); 0.008(3.9); 0.000(113.1); −0.009(3.7); −0.150(0.5)

Example 195: ¹H-NMR(400.0 MHz, DMSO):

δ = 8.746(7.4); 8.315(0.4); 7.880(2.8); 7.862(2.8); 7.497(2.4); 7.470(2.3); 4.030(1.2); 4.004(3.6); 3.979(3.7); 3.953(1.3); 3.501(0.3); 3.321(85.7); 2.931(1.7); 2.912(5.5); 2.893(5.6); 2.874(1.8); 2.675(0.9); 2.670(1.2); 2.666(0.8); 2.541(0.5); 2.524(2.6); 2.519(4.1); 2.510(64.9); 2.506(134.2); 2.501(177.9); 2.497(126.5); 2.492(59.6); 2.459(16.0); 2.435(0.5); 2.428(0.4); 2.414(0.6); 2.337(0.5); 2.333(0.9); 2.328(1.2); 2.324(0.9); 2.319(0.4); 1.398(1.8); 1.321(6.3); 1.303(13.9); 1.284(6.5); 1.272(0.4); 1.266(0.6); 1.249(0.4); 1.232(0.4); 1.219(0.5); 1.214(0.8); 1.197(0.8); 1.185(0.6); 1.180(0.6); 1.170(0.8); 1.151(0.7); 1.139(0.6); 1.132(1.1); 1.114(1.3); 1.109(0.8); 1.097(1.0); 1.091(0.7); 1.080(0.6); 1.073(0.5); 1.062(0.5); 1.055(0.4); 1.046(0.4); 0.008(1.5); 0.000(50.5); −0.009(1.7)

Example 196: ¹H-NMR(400.0 MHz, DMSO):

δ = 8.768(16.0); 8.316(1.0); 8.149(6.4); 8.131(6.4); 7.614(3.5); 7.588(3.5); 5.756(1.6); 4.323(0.4); 4.317(0.4); 4.303(0.5); 4.278(0.7); 4.252(0.8); 4.242(0.8); 4.230(0.8); 4.206(0.6); 4.193(0.5); 4.169(0.3); 4.152(0.8); 4.147(0.3); 4.051(0.8); 4.036(0.8); 3.362(0.3); 3.320(108.7); 2.755(0.3); 2.675(2.2); 2.671(3.0); 2.666(2.2); 2.645(0.4); 2.604(0.5); 2.583(0.4); 2.540(2.1); 2.510(220.5); 2.506(349.3); 2.501(448.5); 2.497(322.3); 2.493(159.0); 2.486(45.3); 2.459(1.2); 2.429(0.4); 2.414(0.5); 2.332(2.2); 2.328(3.1); 2.324(2.2); 1.233(0.5); 1.204(0.5); 1.186(0.6); 1.166(0.5); 1.146(0.5); 1.127(0.4); 1.099(0.4); 1.085(0.4); 0.146(1.3); 0.021(0.6); 0.008(11.4); 0.000(294.3); −0.008(11.3); −0.150(1.4)

Example 197: ¹H-NMR(400.0 MHz, DMSO):

δ = 8.947(8.2); 7.867(2.9); 7.849(2.9); 7.528(2.4); 7.501(2.3); 4.025(1.2); 4.000(3.7); 3.974(3.9); 3.948(1.3); 3.321(60.3); 2.675(0.4); 2.671(0.6); 2.666(0.4); 2.541(0.4); 2.524(1.5); 2.519(2.5); 2.511(34.5); 2.506(70.6); 2.502(93.0); 2.497(64.9); 2.492(29.6); 2.473(16.0); 2.449(0.4); 2.333(0.5); 2.328(0.4); 2.324(0.4); 1.398(9.9); 1.210(0.4); 1.201(0.5); 1.157(0.5); 1.147(0.4); 1.139(0.8); 1.130(0.5); 1.121(0.5); 1.114(0.4); 1.073(0.3); 1.055(0.5); 0.008(0.5); 0.000(16.3); −0.009(0.5)

Example 198: ¹H-NMR(400.0 MHz, DMSO):

δ = 8.777(10.1); 8.157(4.2); 8.139(4.2); 7.613(2.5); 7.587(2.4); 5.756(0.7); 4.249(0.7); 4.241(0.7); 4.233(0.7); 4.222(0.7); 4.214(0.6); 4.136(0.4); 4.118(0.6); 4.102(0.6); 4.090(0.7); 4.072(0.7); 3.568(0.6); 3.321(40.1); 2.930(2.3); 2.911(7.0); 2.893(7.2); 2.874(2.4); 2.675(0.8); 2.670(0.8); 2.505(99.2); 2.501(122.1); 2.497(91.3); 2.487(28.5); 2.416(0.4); 2.398(0.7); 2.387(0.6); 2.328(1.0); 1.325(7.9); 1.306(16.0); 1.287(7.8); 1.272(0.7); 1.266(0.9); 1.249(0.7); 1.232(0.9); 1.214(2.0); 1.197(1.3); 1.188(1.8); 1.183(1.8); 1.173(1.5); 1.165(1.1); 1.151(1.0); 1.147(1.0); 1.139(0.9); 1.129(0.9); 1.115(0.9); 1.097(1.0); 1.087(0.6); 1.080(0.6); 0.000(32.6); −0.001 (31.9); −0.008(1.6)

Example 199: ¹H-NMR(400.0 MHz, DMSO):

δ = 8.971(16.0); 8.316(0.5); 8.189(0.3); 8.167(6.9); 8.149(6.8); 7.639(2.8); 7.613(2.8); 5.756(6.9); 4.358(0.3); 4.345(0.5); 4.333(0.5); 4.253(0.8); 4.227(0.7); 4.201(0.5); 4.191(0.5); 4.158(0.4); 4.140(0.6); 4.122(0.7); 4.105(0.7); 4.090(0.7); 4.056(0.8); 4.038(0.8); 3.958(0.4); 3.568(0.7); 3.321(119.3); 2.675(1.2); 2.670(1.7); 2.666(1.2); 2.648(0.4); 2.541(1.4); 2.524(4.7); 2.510(92.1); 2.506(185.7); 2.501(244.7); 2.497(175.9); 2.492(95.3); 2.410(0.6); 2.337(0.6); 2.332(1.1); 2.328(1.7); 2.324(1.3); 1.306(0.3); 1.287(0.3); 1.270(0.4); 1.235(0.6); 1.227(0.7); 1.214(1.6); 1.209(1.0); 1.200(0.4); 1.191(0.8); 1.188(1.3); 1.183(1.8); 1.174(1.3); 1.167(0.9); 1.161(0.9); 1.143(0.8); 1.125(0.4); 1.073(0.6); 1.055(0.9); 1.038(0.5); 0.855(0.4); 0.146(0.3); 0.008(2.6); 0.000(79.6); −0.009(2.8); −0.150(0.3)

Example 200: ¹H-NMR(400.0 MHz, DMSO):

δ = 8.787(6.5); 8.167(2.2); 8.148(2.2); 7.612(1.1); 7.586(1.1); 5.755(0.7); 3.325(12.2); 3.308(1.4); 3.291(1.6); 3.274(1.2); 3.256(0.5); 2.525(0.9); 2.511(17.2); 2.507(34.1); 2.502(44.2); 2.498(31.6); 2.493(17.2); 2.489(14.2); 2.461(0.5); 2.456(0.4); 2.439(0.4); 2.329(0.4); 1.480(0.3); 1.462(0.3); 1.364(16.0); 1.347(15.7); 0.008(1.1); 0.000(30.6); −0.009(1.1)

Example 201: ¹H-NMR(400.0 MHz, DMSO):

δ = 8.620(7.6); 8.611(0.3); 8.316(0.4); 7.904(2.8); 7.886(2.8); 7.496(2.4); 7.469(2.4); 4.041(1.1); 4.015(3.6); 3.989(3.8); 3.963(1.3); 3.322(113.2); 3.133(1.7); 3.115(5.4); 3.096(5.5); 3.077(1.8); 2.675(0.9); 2.671(1.2); 2.666(0.9); 2.662(0.4); 2.541(0.8); 2.524(3.4); 2.510(73.8); 2.506(145.3); 2.502(187.5); 2.497(132.0); 2.493(61.8); 2.461(16.0); 2.395(0.6); 2.333(0.9); 2.328(1.2); 2.324(0.9); 2.074(2.0); 1.288(6.3); 1.269(13.2); 1.250(6.1); 0.146(0.6); 0.007(5.2); 0.000(127.1); −0.009(4.4); −0.150(0.6)

Example 202: ¹H-NMR(400.0 MHz, DMSO):

δ = 8.612(5.2); 7.901(1.9); 7.883(2.0); 7.497(1.6); 7.470(1.6); 4.038(0.9); 4.013(2.5); 3.987(2.6); 3.961(0.9); 3.322(62.4); 2.702(16.0); 2.675(0.4); 2.671(0.5); 2.666(0.4); 2.530(0.6); 2.524(1.2); 2.519(1.8); 2.511(28.9); 2.506(59.7); 2.502(79.2); 2.497(56.2); 2.493(26.3); 2.461(10.9); 2.333(0.4); 2.328(0.5); 2.324(0.4); 1.989(0.8); 1.398(1.4); 1.175(0.5); 0.008(0.6); 0.000(19.4); −0.009(0.6)

Example 203: ¹H-NMR(400.0 MHz, DMSO):
δ = 8.672(0.4); 8.658(9.3); 8.316(1.2); 8.169(4.0); 8.151(4.0); 7.799(0.4); 7.615(2.8); 7.588(2.7); 4.305(0.4); 4.281(0.6); 4.272(0.6); 4.256(0.8); 4.250(0.7); 4.227(0.6); 4.219(0.7); 4.203(0.5); 4.156(0.5); 4.124(0.5); 4.096(0.5); 4.044(1.1); 4.040(1.1); 3.991(0.6); 3.968(0.4); 3.598(0.5); 3.568(2.6); 3.540(0.3); 3.403(0.3); 3.321(133.1); 3.279(0.3); 3.136(2.3); 3.117(7.0); 3.099(7.2); 3.080(2.4); 2.890(0.5); 2.803(0.4); 2.796(0.4); 2.789(0.4); 2.774(0.5); 2.758(0.4); 2.731(0.5); 2.670(3.8); 2.637(0.6); 2.616(0.6); 2.505(449.0); 2.501(556.3); 2.497(407.6); 2.461(1.5); 2.425(0.7); 2.391(0.7); 2.382(0.7); 2.328(3.6); 2.311(0.4); 2.288(0.3); 2.194(0.3); 2.179(0.3); 1.587(0.4); 1.575(0.3); 1.564(0.4); 1.551(0.3); 1.349(0.3); 1.291(7.8); 1.272(16.0); 1.254(7.7); 1.234(2.0); 1.215(3.1); 1.183(4.3); 1.174(3.0); 1.166(2.3); 1.151(1.1); 0.868(0.4); 0.850(0.4); 0.146(1.2); 0.000(268.8); −0.035(0.4); −0.150(1.3)

Example 204: ¹H-NMR(400.0 MHz, DMSO):

δ = 8.652(5.2); 8.165(2.3); 8.146(2.3); 7.618(1.5); 7.591(1.5); 5.756(4.4); 4.253(0.4); 4.068(0.4); 3.324(25.9); 2.705(16.0); 2.671(0.3); 2.666(0.3); 2.541(0.4); 2.506(36.2); 2.502(44.2); 2.497(33.3); 2.493(25.4); 2.409(0.3); 2.329(0.4); 1.215(0.3); 1.184(0.4); 0.008(1.1); 0.000(12.4); −0.009(0.5)

Example 205: ¹H-NMR(400.0 MHz, DMSO):

δ = 7.951(1.9); 7.933(1.9); 7.564(1.6); 7.537(1.6); 3.998(0.8); 3.972(2.6); 3.947(2.7); 3.921(0.9); 3.324(21.4); 2.796(16.0); 2.541(0.4); 2.536(0.3); 2.524(0.8); 2.507(37.0); 2.502(37.1); 2.498(25.8); 2.493(12.2); 0.008(2.6); 0.000(66.8); −0.009(2.5)

Example 206: ¹H-NMR(400.0 MHz, DMSO):

δ = 8.316(0.5); 8.223(2.1); 8.204(2.1); 7.682(1.7); 7.655(1.6); 4.373(0.6); 4.346(0.7); 4.336(0.8); 4.309(0.8); 4.058(0.7); 4.031(0.8); 4.021(0.7); 4.004(0.3); 3.994(0.7); 3.325(181.5); 2.796(16.0); 2.675(1.0); 2.671(1.4); 2.666(1.0); 2.662(0.5); 2.541(0.7); 2.524(3.6); 2.511(74.3); 2.506(151.0); 2.502(207.3); 2.497(150.3); 2.493(72.4); 2.338(0.5); 2.333(1.0); 2.328(1.3); 2.324(0.9); 2.075(1.0); 0.008(0.5); 0.000(16.0); −0.009(0.6)

Example 207: ¹H-NMR(400.0 MHz, DMSO):

δ = 8.654(2.9); 7.921(1.0); 7.903(1.0); 7.491(0.9); 7.464(0.8); 4.050(0.4); 4.024(1.2); 3.998(1.3); 3.973(0.5); 3.324(10.7); 2.525(0.6); 2.511(12.3); 2.507(24.0); 2.502(30.7); 2.498(21.5); 2.493(10.0); 2.462(5.4); 2.281(0.4); 1.445(16.0); 1.232(0.4); 0.008(1.0); 0.000(23.5); −0.009(0.8)

Example 208: ¹H-NMR(400.0 MHz, DMSO):

δ = 8.691(1.4); 8.187(0.7); 8.169(0.7); 7.609(0.4); 7.583(0.4); 5.757(1.7); 3.324(39.3); 2.675(0.4); 2.671(0.6); 2.666(0.4); 2.541(0.4); 2.524(1.4); 2.511(32.5); 2.506(64.7); 2.502(84.1); 2.497(61.5); 2.493(29.7); 2.333(0.5); 2.329(0.6); 2.324(0.4); 1.450(16.0); 1.234(0.5); 0.070(0.7); 0.068(0.5); 0.008(1.1); 0.000(32.4); −0.009(1.1)

-continued

Example 209: ¹H-NMR(400.0 MHz, DMSO):

δ = 7.887(2.0); 7.868(2.0); 7.523(1.8); 7.496(1.8); 5.756(0.8); 4.062(0.4); 4.049(0.4); 4.037(0.5); 4.023(1.1); 3.998(1.3); 3.991(1.2); 3.972(0.5); 3.965(1.2); 3.952(0.4); 3.939(0.4); 3.926(0.4); 3.327(39.8); 2.658(16.0); 2.554(0.5); 2.511(11.8); 2.507(23.1); 2.503(29.8); 2.498(21.5); 2.463(11.6); 2.254(0.4); 2.234(14.0); 1.139(1.5); 0.008(1.4); 0.000(32.8); −0.008(1.3)

Example 210: ¹H-NMR(400.0 MHz, DMSO):

δ = 8.161(2.3); 8.143(3.2); 8.125(1.3); 7.660(2.1); 7.651(1.4); 7.634(2.1); 7.625(1.3); 5.757(2.1); 4.380(0.7); 4.353(0.9); 4.343(0.9); 4.325(0.4); 4.316(0.9); 4.289(0.5); 4.261(0.5); 4.251(0.8); 4.236(0.9); 4.225(0.9); 4.209(0.8); 4.199(0.4); 3.991(0.9); 3.963(1.0); 3.954(0.8); 3.936(0.5); 3.927(0.7); 3.327(110.3); 3.291(0.4); 2.662(16.0); 2.653(9.8); 2.553(0.5); 2.502(150.5); 2.450(0.6); 2.444(0.4); 2.329(1.2); 2.308(8.1); 2.218(13.8); 1.235(0.5); 1.215(1.7); 1.184(2.0); 1.175(1.1); 1.138(1.2); 0.000(53.1)

Example 211: ¹H-NMR(400.0 MHz, DMSO):

δ = 9.614(8.2); 8.275(7.2); 7.887(2.9); 7.869(2.9); 7.490(2.5); 7.463(2.5); 4.039(1.3); 4.014(3.9); 4.002(0.4); 3.988(4.0);3.962(1.4); 3.322(46.0); 2.787(0.4); 2.675(0.4); 2.671(0.5); 2.667(0.4); 2.524(1.4); 2.511(31.3); 2.506(61.3); 2.502(78.8);2.497(55.1); 2.493(25.3); 2.459(16.0); 2.333(0.4); 2.329(0.5); 2.324(0.4); 1.989(1.2); 1.398(1.3); 1.193(0.4); 1.175(0.7); 1.157(0.4); 0.008(1.6); 0.000(38.2); −0.009(1.2)

Example 212: ¹H-NMR(400.0 MHz, DMSO):

δ = 9.610(16.0); 8.326(11.0); 8.315(0.8); 8.149(6.5); 8.131(6.6); 7.606(4.6); 7.580(4.6); 5.756(6.9); 4.498(1.3); 4.249(0.9); 4.086(0.8); 4.056(0.6); 4.038(0.5); 4.020(0.4); 3.568(0.3); 3.323(228.0); 2.790(1.0); 2.675(1.0); 2.671(1.3); 2.667(1.0); 2.553(2.6); 2.541(0.9); 2.506(156.6); 2.502(204.3); 2.497(148.2); 2.487(40.6); 2.333(1.0); 2.328(1.4); 2.324(1.1); 1.989(0.6); 1.235(0.6); 1.215(2.5); 1.206(0.5); 1.188(1.6); 1.183(2.5); 1.175(1.7); 1.139(7.6); 1.115(0.4); 0.008(1.6); 0.000(44.0); −0.008(1.7)

Example 213: ¹H-NMR(601.6 MHz, DMSO):

δ = 7.979(5.3); 7.808(2.0); 7.796(2.0); 7.445(1.7); 7.427(1.6); 5.755(5.2); 4.041(0.7); 4.027(16.0); 4.007(2.3); 3.990(0.8); 3.321(13.8); 2.508(8.0); 2.502(29.8); 2.499(18.9); 2.496(9.3); 2.448(11.8); 0.000(5.4)

Example 214: ¹H-NMR(400.0 MHz, DMSO):

δ = 8.054(3.2); 8.037(2.3); 8.018(2.3); 7.577(1.7); 7.551(1.7); 5.756(2.7); 4.207(0.3); 4.131(0.3); 4.032(16.0); 3.321(9.7); 2.745(0.8); 2.512(27.0); 2.506(30.6); 2.502(38.3); 2.497(27.4); 2.493(13.2); 2.480(12.2); 0.008(1.4); 0.000(37.4); −0.009(1.3)

Example 215: ¹H-NMR(400.0 MHz, DMSO):

δ = 8.445(6.1); 8.038(6.0); 7.836(2.3); 7.818(2.3); 7.455(2.0); 7.428(2.0); 4.122(16.0); 4.060(0.9); 4.035(2.9); 4.009(3.0); 3.983(1.0); 3.327(31.8); 2.690(0.4); 2.525(0.6); 2.511(14.0); 2.507(28.1); 2.502(36.7); 2.498(26.4); 2.493(12.7); 2.481(0.6); 2.447(12.8); 2.086(0.5); 1.397(6.1); 0.008(0.5); 0.000(14.6); −0.009(0.6)

Example 216: ¹H-NMR(400.0 MHz, DMSO):

δ = 8.456(5.7); 8.111(2.9); 8.072(0.5); 8.060(2.3); 8.041(2.3); 7.581(1.8); 7.555(1.8); 5.757(2.2); 4.232(0.4); 4.199(0.4); 4.126(16.0); 3.325(152.3); 2.745(0.9); 2.675(0.7); 2.671(0.9); 2.666(0.7); 2.506(111.3); 2.502(142.1); 2.498(106.7); 2.482(15.6); 2.435(0.4); 2.333(0.8); 2.329(1.0); 2.324(0.7); 0.008(2.7); 0.000(51.9)

Example 217: ¹H-NMR(400.0 MHz, DMSO):

δ = 10.302(0.6); 9.770(0.4); 8.323(0.6); 8.316(1.6); 7.935(4.9); 7.822(2.2); 7.803(2.2); 7.614(4.6); 7.442(1.9); 7.414(1.9); 5.025(0.5); 4.051(1.0); 4.024(2.8); 3.998(2.9); 3.973(1.1); 3.322(494.3); 2.967(1.6); 2.868(16.0); 2.721(1.1); 2.703(0.3); 2.675(4.4); 2.671(5.7); 2.666(4.2); 2.510(385.4); 2.506(699.4); 2.502(872.9); 2.497(637.5); 2.493(328.0); 2.442(13.6); 2.416(1.5); 2.333(4.4); 2.328(5.6); 2.324(4.3); 1.235(0.4); 1.209(0.5); 0.146(3.7); 0.008(47.7); 0.000(828.8); −0.008(50.0); −0.150(3.8)

Example 218: ¹H-NMR(400.0 MHz, DMSO):

δ = 8.315(2.3); 8.177(0.4); 8.046(2.2); 8.027(2.1); 8.007(3.2); 7.969(0.5); 7.856(0.3); 7.835(0.3); 7.630(4.9); 7.611(0.5); 7.568(1.5); 7.541(1.7); 4.259(0.5); 4.232(0.5); 4.199(0.5); 4.173(0.5); 4.145(0.6); 4.114(0.5); 3.361(0.5); 3.344(1.0); 3.319(468.0); 3.185(1.1); 2.969(0.4); 2.891(0.7); 2.873(16.0); 2.739(1.1); 2.732(0.5); 2.675(3.9); 2.670(5.4); 2.666(3.9); 2.610(0.3); 2.596(0.4); 2.540(3.4); 2.524(14.1); 2.510(326.5); 2.506(642.0); 2.501(824.8); 2.497(577.3); 2.492(267.0); 2.477(14.7); 2.440(0.6); 2.405(1.6); 2.394(0.8); 2.337(2.0); 2.333(3.8); 2.328(5.3);

2.323(3.7); 2.136(0.4); 1.351(0.4); 1.335(0.4); 1.297(0.6); 1.259(1.1); 1.235(3.4); 1.171(0.3); 1.046(0.4); 1.019(0.3); 0.884(0.6); 0.868(0.7); 0.854(0.7); 0.838(0.5); 0.146(3.5); 0.053(0.3); 0.036(0.4); 0.028(0.9); 0.025(1.1); 0.008(32.4); 0.000(837.4); −0.009(28.2); −0.015(2.9); −0.022(1.9); −0.027(0.4); −0.032(0.5); −0.082(0.4); −0.088(0.3); −0.142(0.4); −0.150(3.4)

Example 219: ¹H-NMR(601.6 MHz, DMSO):

δ = 8.380(4.6); 7.992(5.0); 7.823(2.1); 7.811(2.1); 7.446(1.8); 7.428(1.8); 4.036(0.8); 4.020(2.5); 4.002(2.7); 3.985(0.9); 3.320(31.3); 2.891(0.6); 2.869(0.6); 2.732(0.4); 2.690(0.6); 2.648(16.0); 2.616(0.4); 2.613(0.5); 2.610(0.4); 2.520(0.4); 2.508(21.8); 2.505(51.1); 2.502(74.0); 2.499(56.3); 2.496(28.8); 2.474(0.8); 2.457(0.5); 2.442(12.9); 2.418(0.4); 2.403(0.6); 2.389(0.6); 2.386(0.8); 2.383(0.7); 2.379(0.7); 2.362(0.5); 2.323(0.3); 2.086(0.4); 1.235(0.5); 0.000(16.5); −0.006(0.9)

Example 220: ¹H-NMR(400.0 MHz, DMSO):

δ = 8.397(5.2); 8.315(0.6); 8.062(5.2); 8.041(2.4); 7.578(1.8); 7.551(1.8); 5.756(0.4); 4.238(0.5); 4.210(0.4); 4.136(0.4); 4.109(0.5); 3.685(0.4); 3.321(111.9); 2.869(0.4); 2.819(0.4); 2.689(0.7); 2.679(0.8); 2.675(1.4); 2.670(1.9); 2.666(1.7); 2.656(16.0); 2.624(0.3); 2.602(0.4); 2.592(0.4); 2.578(0.4); 2.564(0.6); 2.541(1.4); 2.524(5.0); 2.519(7.5); 2.510(89.4); 2.506(180.5); 2.501(238.9); 2.497(172.4); 2.492(82.3); 2.477(13.0); 2.362(0.4); 2.337(0.6); 2.333(1.3); 2.328(2.0); 2.324(1.5); 1.234(0.8); 0.008(0.6); 0.000(18.9); −0.009(0.7)

Example 221: ¹H-NMR(400.0 MHz, DMSO):

δ = 10.083(0.4); 9.794(0.4); 8.352(0.4); 8.331(7.0); 8.316(2.4); 8.290(0.9); 8.269(0.4); 7.848(2.8); 7.830(2.7); 7.816(0.4); 7.469(2.4); 7.443(2.4); 7.282(0.5); 7.250(0.5); 7.051(0.5); 6.762(4.5); 6.760(4.1); 4.055(1.2); 4.029(3.6); 4.003(3.7); 3.978(1.3); 3.856(0.5); 3.829(0.7); 3.808(2.0); 3.777(0.6); 3.719(0.4); 3.399(0.3); 3.324(849.0); 3.138(0.4); 2.969(1.4); 2.944(0.5); 2.921(1.6); 2.909(0.9); 2.899(0.4); 2.868(1.7); 2.675(4.5); 2.671(5.9); 2.666(4.3); 2.541(3.0); 2.524(14.9); 2.506(733.0); 2.502(944.5); 2.497(675.0); 2.447(16.0); 2.402(2.5); 2.378(4.5); 2.333(4.7); 2.328(6.2); 2.324(5.0); 2.283(0.4); 2.225(0.4); 1.398(1.0); 1.351(0.4); 1.299(0.5); 1.259(0.8); 1.234(2.5); 1.139(0.4); 0.854(0.4); 0.146(1.4); 0.008(12.4); 0.000(335.2); −0.008(14.0); −0.150(1.6)

Example 222: ¹H-NMR(400.0 MHz, DMSO):

δ = 19.995(0.7); 8.612(0.6); 8.394(5.8); 8.354(0.8); 8.316(4.0); 8.080(3.3); 8.061(3.0); 7.594(2.4); 7.567(2.4); 6.771(4.7); 4.221(0.7); 4.104(1.0); 3.935(0.6); 3.324(1574.7); 3.235(1.0); 3.185(0.7); 2.927(0.9); 2.737(0.9); 2.671(14.0); 2.506(1640.8); 2.502(2080.7); 2.497(1632.9); 2.328(16.0); 1.350(0.6); 1.297(0.7); 1.234(4.7); 0.854(0.8); 0.146(3.3); 0.008(53.0); 0.000(734.3); −0.150(3.4)

Use Examples

1. *Myzus persicae* Spray Test (MYZUPE)

Solvents: 78 parts by weight of acetone
  1.5 part by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% here means that all of the aphids have been killed; 0% means that no aphids have been killed.

In this test, for example, the following compounds of the Preparation Examples show, at an application rate of 500 g/ha, an efficacy of 100%: 125, 175

In this test, for example, the following compounds of the Preparation Examples show, at an application rate of 500 g/ha, an efficacy of 90%: 53, 172

2. *Phaedon cochleariae* Spray Test (PHAECO)

Solvents: 78.0 parts by weight of acetone
1.5 part by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all of the beetle larvae have been killed; 0% means that none of the beetle larvae have been killed.

In this test, for example, the following compounds of the Preparation Examples show, at an application rate of 500 g/ha, an efficacy of 100%: 1, 2, 33, 34, 36, 46, 51, 60, 61, 82, 88, 89, 95, 96, 105, 112, 165, 183, 191, 201, 205, 206

In this test, for example, the following compounds of the Preparation Examples show, at an application rate of 500 g/ha, an efficacy of 83%: 106, 120, 136, 161, 204, 208

3. *Spodoptera frugiperda* Spray Test (SPODFR)

Solvents: 78.0 parts by weight of acetone
1.5 part by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all of the caterpillars have been killed; 0% means that none of the caterpillars have been killed.

In this test, for example, the following compounds of the Preparation Examples show an efficacy of 100% at an application rate of 500 g/ha: 33, 46, 205, 206

In this test, for example, the following compounds of the Preparation Examples show, at an application rate of 500 g/ha, an efficacy of 83%: 36

4. *Tetranychus urticae* Spray Test, OP-Resistant (TETRUR)

Solvents: 78.0 parts by weight of acetone
1.5 part by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After 6 days, the efficacy in % is determined. 100% means that all of the spider mites have been killed; 0% means that none of the spider mites have been killed.

In this test, for example, the following compounds of the Preparation Examples show, at an application rate of 500 g/ha, an efficacy of 100%: 2, 41, 54, 73, 79, 91, 92, 96, 125, 127, 128, 130, 132, 134, 136, 137, 138, 139, 140, 142, 143, 145, 147, 148, 149, 150, 151, 156, 157, 158, 159, 160, 161, 162, 163, 164, 165, 166, 167, 169, 170, 175, 178, 179, 181, 188, 191, 193, 197, 200, 203, 205, 206, 208, 210, 213, 216, 219, 222

In this test, for example, the following compounds of the Preparation Examples show, at an application rate of 500 g/ha, an efficacy of 90%: 1, 15, 20, 26, 27, 33, 37, 38, 39, 40, 47, 52, 53, 61, 66, 68, 72, 75, 76, 78, 86, 116, 117, 118, 119, 120, 126, 129, 131, 133, 135, 144, 152, 153, 154, 155, 172, 173, 176, 180, 183, 185, 186, 189, 190, 192, 194, 195, 198, 199, 201, 202, 204, 209, 212, 214, 217, 218, 220

In this test, for example, the following compounds of the Preparation Examples show, at an application rate of 100 g/ha, an efficacy of 90%: 112, 174, 196

5. *Meloidogyne incognita* Test (MELGIN)

Solvent: 125.0 parts by weight of acetone

To prepare a suitable active compound preparation, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. On the roots, galls are formed.

After 14 days, the nematicidal effect in % is determined by the formation of galls. 100% means that no galls have been found; 0% means that the number of galls on the treated plants corresponds to the untreated control.

In this test, for example, the following compounds of the Preparation Examples show, at an application rate of 20 ppm, an efficacy of 100%: 40, 53, 87, 134, 142, 147, 148, 149, 153, 155, 159, 160, 161, 164, 165, 167, 169, 170, 194, 196, 198, 199, 200, 204, 206, 208, 209, 210, 212

In this test, for example, the following compounds of the Preparation Examples show, at an application rate of 20 ppm, an efficacy of 90%: 15, 18, 19, 32, 41, 43, 46, 49, 61, 63, 64, 70, 72, 73, 78, 79, 86, 89, 96, 97, 108, 112, 113, 114, 118, 129, 136, 146, 157, 162, 163, 168, 181, 188, 195, 202

In this test, for example, the following compounds of the Preparation Examples show, at an application rate of 20 ppm, an efficacy of 80%: 37, 45, 47, 75

6. *Boophilus microplus* Injection Test (BOOPMI Inj)

Solvent: dimethyl sulphoxide

To produce a suitable preparation of active compound, 10 mg of active compound are mixed with 0.5 ml of solvent, and the concentrate is diluted with solvent to the desired concentration.

1 µl of the active compound solution is injected into the abdomen of 5 fed adult female cattle ticks (*Boophilus microplus*). The animals are transferred into dishes and kept in a climate-controlled room.

The activity is assessed after 7 days by laying of fertile eggs. Eggs whose fertility is not visible from the outside are stored in a climate-controlled cabinet until the larvae hatch after about 42 days. An efficacy of 100% means that none of the ticks has laid any fertile eggs; 0% means that all eggs are fertile.

In this test, for example, the following compounds of the Preparation Examples show, at an application rate of 20 μg/animal, an efficacy of 100%: 2, 15, 27, 40, 41, 61, 73, 79, 89, 129, 134, 172, 204

The invention claimed is:

1. A compound of formula (I)

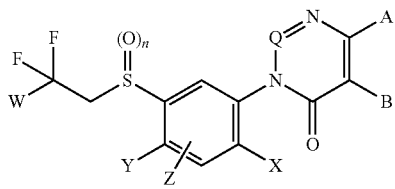

(I)

wherein

A and B together with the carbon atoms to which they are attached represent a substructure selected from the group consisting of

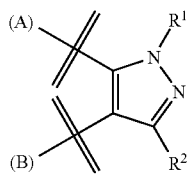

I-1

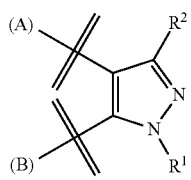

I-2

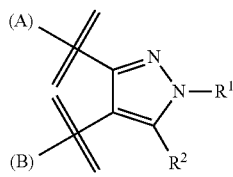

I-3

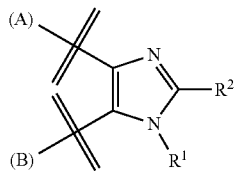

I-8

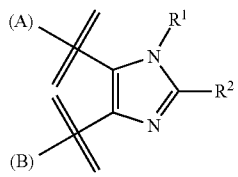

I-9

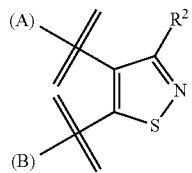

I-11

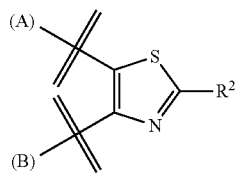

I-12

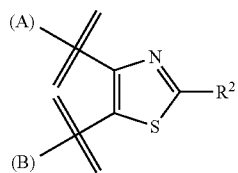

I-13

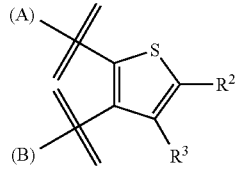

I-16

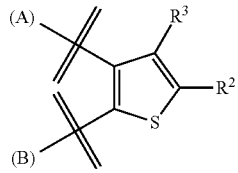

I-17

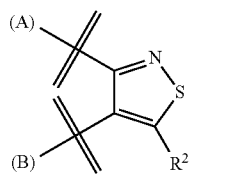

I-18

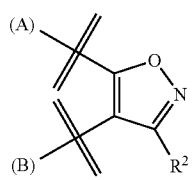

I-20

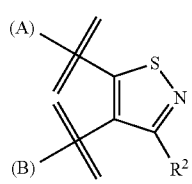

I-21

-continued

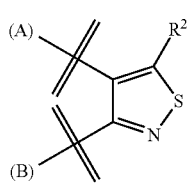
I-22

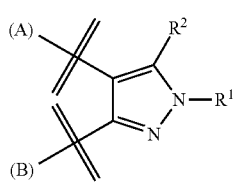
I-24

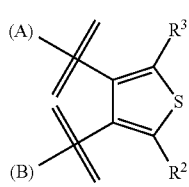
I-25

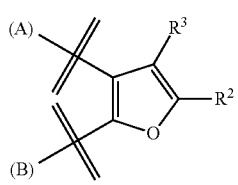
I-26 in which the labels (A) and (B) define the respective points of attachment of the radicals A and B of the general formula (I) and $R^1$, $R^2$ and $R^3$ have the following meanings:

$R^1$ represents hydrogen, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methoxycarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represent cyclopropyl, cyclobutyl, cyclopentyl or cyclohexyl which are mono- or polysubstituted by identical or different substituents from the group consisting of fluorine, chlorine, bromine, cyano, nitro, methyl, ethyl, methoxy, ethoxy, trifluoromethyl and cyclopropyl;

or represents cyclopropylmethyl or cyclobutylmethyl which are mono- or polysubstituted by identical or different substituents from the group consisting of fluorine, chlorine, bromine, cyano, nitro, methyl, ethyl, trifluoromethyl and cyclopropyl;

$R^2$ and $R^3$ independently of one another represent hydrogen, fluorine, chlorine, bromine, iodine, hydroxy, amino, cyano, nitro, OCN, SCN, $SF_5$, trimethylsilyl, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl, trichloromethyl, (2,2,2)-trichloroethyl, vinyl, ethynyl, allyl, butenyl, propynyl, methylcarbonyl, ethylcarbonyl, propylcarbonyl, methoxycarbonyl, ethoxycarbonyl, methylsulphonylamino, ethylsulphonylamino, propylsulphonylamino, aminosulphonyl, methylaminosulphonyl, ethylaminosulphonyl, propylaminosulphonyl, dimethylaminosulphonyl, diethylaminosulphonyl, aminothiocarbonyl, methylaminothiocarbonyl, ethylaminothiocarbonyl, dimethylaminothiocarbonyl or diethylaminothiocarbonyl;

or represent cyclopropyl, cyclobutyl, cyclopentyl or cyclohexyl which are mono- or polysubstituted by identical or different substituents from the group consisting of fluorine, chlorine, bromine, cyano, nitro, methyl, ethyl, methoxy, ethoxy, trifluoromethyl and cyclopropyl;

or represent cyclopropylmethyl or cyclobutylmethyl which are mono- or polysubstituted by identical or different substituents from the group consisting of fluorine, chlorine, bromine, cyano, nitro, methyl, ethyl, methoxy, ethoxy, trifluoromethyl and cyclopropyl;

Q represents C—V; where
  V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl, (2,2)-difluoroethyl;
W represents hydrogen or fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

2. A compound according to claim 1, wherein in formula (I)
A and B together with the carbon atoms to which they are attached represent the radical

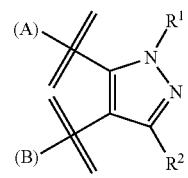
I-1 in which,
Q represents C—V; where
  V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl or (2,2)-difluoroethyl;
W represents hydrogen or fluorine
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

3. A compound according to claim 1, wherein in formula (I)
A and B together with the carbon atoms to which they are attached represent the radical

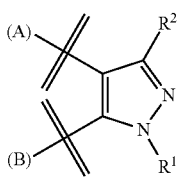

in which,
Q represents C—V; where
V represents hydrogen, fluorine, chlorine, bromine, methyl, ethyl, propyl, isobutyl, butyl, sec-butyl, isopropyl, tert-butyl, trifluoromethyl, (2,2,2)-trifluoroethyl, difluoromethyl or (2,2)-difluoroethyl;
W represents hydrogen or fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

4. A compound according to claim 1, wherein in formula (I)
A and B together with the carbon atoms to which they are attached represent the radical

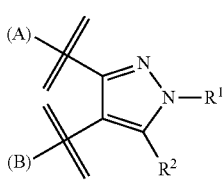

in which,
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

5. A compound according to claim 1, wherein in formula (I)
A and B together with the carbon atoms to which they are attached represent the radical

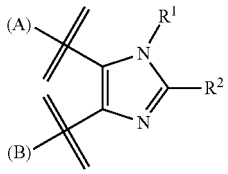

in which,
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

6. A compound according to claim 1, wherein in formula (I)
A and B together with the carbon atoms to which they are attached represent the radical

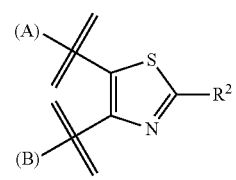

in which
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

7. A compound according to claim 1, wherein in formula (I)
A and B together with the carbon atoms to which they are attached represent the radical

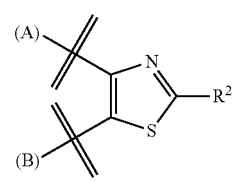

in which
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

8. A compound according to claim 1, wherein in formula (I)
A and B together with the carbon atoms to which they are attached represent the radical

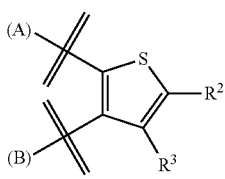

I-16

Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

9. A compound according to claim 1, wherein in formula (I)
A and B together with the carbon atoms to which they are attached represent the radical

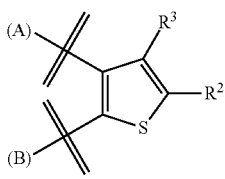

I-17 in which
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

10. A compound according to claim 1, wherein in formula (I)
A and B together with the carbon atoms to which they are attached represent the radical

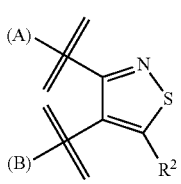

I-18

Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

11. A compound according to claim 1, wherein in formula (I)
A and B together with the carbon atoms to which they are attached represent the radical

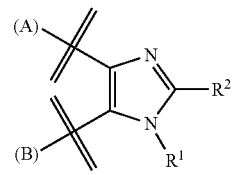

I-8 in which
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

12. A compound according to claim 1, wherein in formula (I)
A and B together with the carbon atoms to which they are attached represent the radical

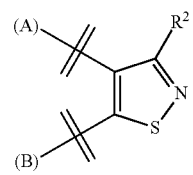

I-11 in which
Q represents C—V; where
V represents hydrogen, methyl, ethyl or trifluoromethyl;
W represents fluorine;
X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;
Z represents hydrogen;
n represents the number 0 or 1.

13. A compound according to claim 1, wherein in formula (I)
A and B together with the carbon atoms to which they are attached represent the radical

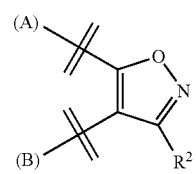

I-20 in which
Q represents C—V; where
V represents hydrogen, methyl, ethyl or trifluoromethyl;
W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

14. A compound according to claim 1, wherein in formula (I)

A and B together with the carbon atoms to which they are attached represent the radical

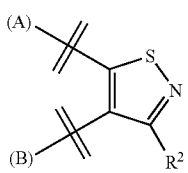

I-21 in which

Q represents C—V; where

V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

15. A compound according to claim 1, wherein in formula (I)

A and B together with the carbon atoms to which they are attached represent the radical

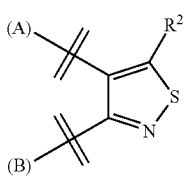

I-22 in which

Q represents C—V; where

V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

16. A compound according to claim 1, wherein in formula (I)

A and B together with the carbon atoms to which they are attached represent the radical

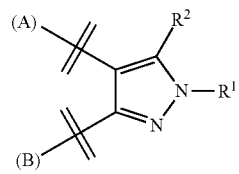

I-24 in which

Q represents C—V; where

V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

17. A compound according to claim 1, wherein in formula (I)

A and B together with the carbon atoms to which they are attached represent the radical

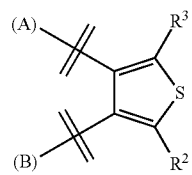

I-25 in

Q represents C—V; where

V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

18. A compound according to claim 1, wherein in formula (I)

A and B together with the carbon atoms to which they are attached represent the radical

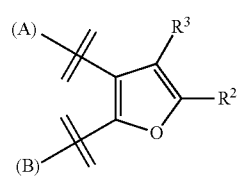

I-26 in which

Q represents C—V; where

V represents hydrogen, methyl, ethyl or trifluoromethyl;

W represents fluorine;

X and Y independently of one another represent hydrogen, fluorine, chlorine, bromine, methyl, ethyl, trifluoromethyl, difluoromethyl, difluoromethoxy, trifluoromethoxy, cyclopropyl, cyano or nitro;

Z represents hydrogen;

n represents the number 0 or 1.

19. An agrochemical composition, comprising one or more compounds of formula (I) according to claim 1 and one or more extenders and/or surfactants.

20. A process for preparing an agrochemical composition, comprising mixing a compound of formula (I) according to claim 1 with one or more extenders and/or surfactants.

21. A method for controlling one or more animal pests, comprising allowing an effective amount of one or more compounds of formula (I) according to claim 1 to act on said one or more animal pests and/or a habitat thereof.

22. A method according to claim 21 comprising controlling one or more animal pests in crop protection, and/or in protection of one or more materials and/or in a veterinary sector.

23. A compound according to claim 1, wherein Q is C—V.

24. A compound according to claim 1, wherein where X and Y represent one of the the following combinations (Y,X): (Me,F), (Me,Cl), (Me,Me), (Me,H), (Et,Et), (Cl,Fl), (Cl,Cl), (Cl,H), (MeO,F), (MeO,H), (Br,F), (Br,Cl), (Br,H), (F,F), ($CF_3$,F), ($CF_3$,H), (CN,F), or (CN,H).

* * * * *